US008586607B2

(12) United States Patent
Ulven et al.

(10) Patent No.: US 8,586,607 B2
(45) Date of Patent: Nov. 19, 2013

(54) COMPOUNDS FOR THE TREATMENT OF METABOLIC DISEASES

(75) Inventors: Trond Ulven, Odense M (DK); Elisabeth Christiansen, Odense M (DK)

(73) Assignee: Syddansk Universitet, Odense M (DK)

( * ) Notice: Subject to any disclaimer, the term of this patent is extended or adjusted under 35 U.S.C. 154(b) by 128 days.

(21) Appl. No.: 13/056,484

(22) PCT Filed: Jul. 23, 2009

(86) PCT No.: PCT/EP2009/059527
§ 371 (c)(1),
(2), (4) Date: Mar. 7, 2011

(87) PCT Pub. No.: WO2010/012650
PCT Pub. Date: Feb. 4, 2010

(65) Prior Publication Data
US 2011/0152315 A1    Jun. 23, 2011

Related U.S. Application Data

(60) Provisional application No. 61/084,098, filed on Jul. 28, 2008.

(51) Int. Cl.
| | | |
|---|---|---|
| *A61K 31/47* | (2006.01) | |
| *A61K 31/4418* | (2006.01) | |
| *A61K 31/4192* | (2006.01) | |
| *A61K 31/426* | (2006.01) | |
| *A61K 31/381* | (2006.01) | |
| *A61K 31/255* | (2006.01) | |
| *A61K 31/275* | (2006.01) | |
| *A61K 31/216* | (2006.01) | |
| *A61K 31/192* | (2006.01) | |
| *C07D 215/14* | (2006.01) | |
| *C07D 213/76* | (2006.01) | |
| *A61P 3/00* | (2006.01) | |

(52) U.S. Cl.
USPC ........... 514/311; 514/277; 514/352; 514/359; 514/365; 514/369; 514/438; 514/518; 514/521; 514/532; 514/570; 546/174; 546/312; 546/342; 548/204; 548/255; 549/79; 558/58; 558/406; 560/60; 560/61; 560/104; 562/470; 562/495; 435/375

(58) Field of Classification Search
USPC .......................................... 514/311
See application file for complete search history.

(56) References Cited

U.S. PATENT DOCUMENTS

| | | | |
|---|---|---|---|
| 6,284,796 B1 | 9/2001 | Geyer et al. | |
| 6,313,107 B1 | 11/2001 | Vasudevan et al. | |
| 6,492,421 B1 | 12/2002 | Thorsett et al. | |
| 6,518,283 B1 | 2/2003 | Langham et al. | |

| | | | |
|---|---|---|---|
| 2004/0192743 A1 | 9/2004 | Mjalli et al. | |
| 2005/0131014 A1* | 6/2005 | Collini et al. | 514/311 |
| 2007/0066647 A1* | 3/2007 | Akerman et al. | 514/310 |
| 2008/0021069 A1 | 1/2008 | Itoh et al. | |

FOREIGN PATENT DOCUMENTS

| | | | |
|---|---|---|---|
| EP | 0 915 086 A1 | 5/1999 | |
| EP | 1 325 903 A1 | 7/2003 | |
| WO | WO 98/57634 | * 12/1998 | |
| WO | WO 99/29640 | 6/1999 | |
| WO | WO-99-29640 | * 6/1999 | |
| WO | WO 2004/071447 A2 | 8/2004 | |
| WO | WO 2005/051890 A1 | 6/2005 | |
| WO | WO 2005/086661 A2 | 9/2005 | |
| WO | WO 2006/022442 A1 | 3/2006 | |
| WO | WO 2007/049050 A2 | 5/2007 | |
| WO | WO 2007/093364 A1 | 8/2007 | |
| WO | WO 2008/001931 A2 | 1/2008 | |
| WO | WO 2008/030618 A1 | 3/2008 | |
| WO | WO 2008/054675 A2 | 5/2008 | |
| WO | WO 2008/071453 A1 | 6/2008 | |

OTHER PUBLICATIONS

Chen et al., "N-Benzylpyroglutamyl-L-phenylalanine derivatives as VCAM/VLA-4 antagonists," *Bioorganic & Medicinal Chemistry Letters* (2000) 10: 729-7333.

Christiansen et al., "Discovery of potent and selective agonists for the free fatty acid receptor (FFA$_1$/GPR40), a potential target for the treatment of Type II diabetes," *J. Med. Chem.* (2008) 51: 7061-7064.

Kayser et al., "Alkyne bridged α-amino acids by palladium mediated coupling of alkynes with N-t-Boc-4-iodo-phenylalanine methyl ester," *Tetrahedron* (1997) 53 (7): 2475-2484.

Marquez et al. ,"Conformationally constrained analogues of Diacylglycerol (DAG). 31. Modulation of the biological properties of diacylglycerol lactones (DAG-lactones) containing rigid-rod acyl groups separated from the core lactone by spacer units of different lengths," *J. Med. Chem.* (2009) 52: 3274-3283.

McKeown et al., "Solid phase synthesis and SAR of small molecule agonists for the GPR40 receptor," *Bioorganic & Medicinal Chemistry Letters* (2007) 1584-1589.

Raimundo et al., "Integrating fragment assembly and biophysical methods in the chemical advancement of small-molecule antagonists of IL-2: An approach for inhibiting protein-protein interactions," *J. Med. Chem.* (2004) 47: 3111-3130.

(Continued)

*Primary Examiner* — Ernst Arnold
*Assistant Examiner* — Jianfeng Song
(74) *Attorney, Agent, or Firm* — Merchant & Gould P.C.

(57) ABSTRACT

There is provided novel compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

15 Claims, No Drawings

(56) References Cited

OTHER PUBLICATIONS

Waldmann et al., "Identification of potent Ras signaling inhibitors by pathway-selective phenotype-based screening," *Agnew. Chem. Int. Ed.* (2004) 43: 450-454.

Winzell et al., "G-protein-coupled receptors and islet function—Implications for treatment of type 2 diabetes," *Pharmacology & Therapeutics* (2007) 116: 437-448.

Zhang et al., "Synthesis and SAR of α-sulfonylcarboxylic acids as potent matrix metalloproteinase inhibitors," *Bioorganic & Medicinal Chemistry Letters* (2006) 16: 3096-3100.

\* cited by examiner ic acid receptor 1 (FFA$_1$/FFAR1), was recently found to be
COMPOUNDS FOR THE TREATMENT OF METABOLIC DISEASES This application is a National Stage Application of PCT/EP2009/059527, filed 23 Jul. 2009, which claims benefit of U.S. Ser. No. 61/084,098, filed 28 Jul. 2008 and which applications are incorporated herein by reference. To the extent appropriate, a claim of priority is made to each of the above disclosed applications.

FIELD OF THE INVENTION

The present invention relates to novel compounds capable of modulating the G-protein-coupled receptor GPR40, compositions comprising the compounds, and methods for their use for controlling insulin levels in vivo and for the treatment of conditions such as type II diabetes, hypertension, ketoacidosis, obesity, glucose intolerance, and hypercholesterolemia and related disorders associated with abnormally high or low plasma lipoprotein, triglyceride or glucose levels.

BACKGROUND OF THE INVENTION

The production of insulin is central to the regulation of carbohydrate and lipid metabolism. Insulin imbalances lead to conditions such as type II diabetes mellitus, a serious metabolic disease that currently afflicts approximately 246 million people worldwide, and is expected to affect 380 million by 2025. Insulin is secreted from pancreatic beta-cells in response to elevated plasma glucose which is augmented by the presence of fatty acids. The recent recognition of the function of the G-protein coupled receptor GPR40 in modulating insulin secretion has provided insight into regulation of carbohydrate and lipid metabolism in vertebrates, and further provided targets for the development of therapeutic agents for disorders such as obesity, diabetes, cardiovascular disease and dyslipidemia.

GPR40 is a member of the gene superfamily of G-protein coupled receptors (GPCRs) or 7-transmembrane receptors (7TM receptors). These receptors are membrane proteins characterized as having seven transmembrane domains, and respond to a variety of molecules by activating intra-cellular signalling pathways critical to a diversity of physiological functions.

At present there is no cure for diabetes, but the disease can often be managed satisfactory, and various treatments are used to ameliorate the disease. For example, dietetic measures have been employed to balance the relative amounts of proteins, fats, and carbohydrates in a patient. Diabetes education and awareness programmes have also been implemented in several countries. In addition, diabetic conditions of moderate or severe intensity are treated by the administration of insulin. Also, prescription drugs such as thiazolinediones have been employed to rejuvenate impaired insulin production in adult onset diabetics. Other drugs are used to modulate the effectiveness of insulin. In any case, treatment of either juvenile or adult onset diabetes, has achieved only partial success. This is due to most agents targeting either improved beta-cell function or reducing insulin resistance, with the effect attenuating as the disease progressively worsens. Thus patients require the use (often daily) of a combination of agents to control the disease.

Biguanides, such as metformin, became available for treatment of type 2 diabetes in the late 1950s, and have been effective hypoglycaemic agents ever since (Vigneri and Goldfine (1987) Diabetes Care 10, 118-122). Little is known about the exact molecular mechanism of these agents. As an insulin sensitizer, metformin acts predominantly on the liver, where it suppresses glucose release (Goldfine (2001) Hospital Practice 36, 26-36). Metformin has also been shown to inhibit the enzymatic activity of complex I of the respiratory chain and thereby impairs both mitochondrial function and cell respiration, and in so doing decreasing the ATP/ADP ratio which activates AMP-activated protein kinase (AMPK), causing catabolic responses on the short term and insulin sensitization on the long term (Brunmair et al. (2004) Diabetes 53, 1052-1059; Tiikkainen et al. (2004) Diabetes 53, 2169-2176). This drug has been proven effective in both monotherapy and in combination with sulfonylureas or insulin (Davidson and Peters (1997) American Journal of Medicin 102, 99-110). Diabetes in the young is a global phenomenon that is increasing in incidence. Some key transcription factors, important for beta-cell development, differentiation and function, are implicated in diabetes in the young. Some of these are direct targets of current therapeutic agents. The cost of current diabetic drugs is very high and the development of more affordable alternative therapies would be an advantage. The global burden of type 2 diabetes is huge, and action is required to endure affordable diabetes treatment to improve the quality of life of those individuals affected.

As a result of its adipogenic effect, insulin has the undesirable effect of promoting obesity in patients with type 2 diabetes. (Moller, D. E. (2001) Nature 414:821-827). Unfortunately, other anti-diabetic drugs, including metformin, which are currently being used to stimulate glucose transport in patients with type 2 diabetes also possess adipogenic activity. Thus while current drug therapy may provide reduction in blood sugar, it often promotes obesity. Accordingly, new compositions and methods for treating hyperglycemia are desirable. Compositions that stimulate glucose uptake without generating concomitant adipogenic side effects and with no risk of causing excess insulin secretion and concequential hypoglycaemia are especially desirable.

The seven-transmembrane receptor GPR40, or free fatty acid receptor 1 (FFA$_1$/FFAR1), was recently found to be highly expressed on pancreatic beta-cells, and activated by physiological concentrations of free fatty acids. Activation of GPR40 enhanced glucose-stimulated insulin secretion (GSIS), but did not affect insulin secretion at low glucose concentrations. The enhancement of GSIS by GPR40 has been confirmed in vivo. Furthermore, two single nucleotide polymorphisms of GPR40 significantly correlating to obesity and impaired insulin secretion, further validating the link between the receptor and the disease.

WO08030618A1 (BENZO-FUSED COMPOUNDS FOR USE IN TREATING METABOLIC DISORDERS) discloses compositions for treating metabolic disorders such as type II diabetes. This document specifically relates to compounds capable of modulating GPR40.

WO05086661A2 (COMPOUNDS, PHARMACEUTICAL COMPOSITIONS AND METHODS FOR USE IN TREATING METABOLIC DISORDERS) describes alkynyl containing compounds capable of modulating the G-protein-coupled receptor GPR40, compositions comprising the compounds, and methods for their use for controlling insulin levels in viva and for the treatment of conditions such as type II diabetes.

WO08001931A2 (FUSED CYCLIC COMPOUNDS) describes novel fused cyclic compounds having a GPR40 receptor function modulating action, and which are useful as insulin secretagogues or agents for the prophylaxis or treatment of diabetes and the like.

US20080021069A1 (Receptor Function Regulating Agent) also relates to a GPR40 receptor function regulator comprising a fused imidazole compound. According to the specification the GPR40 receptor function regulator is useful as an agent for the prophylaxis or treatment of obesity, hyperinsulinemia, type 2 diabetes and the like.

WO08054675A2 (ANTIDIABETIC BICYCLIC COMPOUNDS) focuses on a new class of GPR40 agonists. The compounds are useful in the treatment of diseases that are modulated by GPR40 agonists, including type 2 diabetes and hyperglycemia that may be associated with type 2 diabetes or pre-diabetic insulin resistance.

WO05051890A1 (AMINOPHENYLCYCLOPROPYL CARBOXYLIC ACIDS AND DERIVATIVES AS AGONISTS TO GPR40) discloses novel therapeutic compounds for use as GPR40 agonists.

Winzell and Ahrén (G-protein-coupled receptors and islet function—Implications for treatment of type 2 diabetes—Pharmacology & Therapeutics 116 (2007) 437-448) confirm that many efforts have been made to produce small molecule GPR40 receptor agonists and antagonists to investigate their potential as drugs for type 2 diabetes. It is mentioned that in clonal β cells, insulin secretion could be potentiated by addition of a GPR40 agonist, suggesting that acute activation of GPR40 may be useful to stimulate insulin secretion. However, since the mouse model with transgenic over-expression of GPR40 exhibited impaired β-cell function and type 2 diabetes chronic activation of the receptor may cause deleterious effects. Therefore, the authors suggest that a GPR40 antagonist may be a more efficient concept because patients with type 2 diabetes usually have elevated circulating free fatty acids.

Briscoe et al (Pharmacological regulation of insulin secretion in MIN6 cells through the fatty acid receptor GPR40: identification of agonist and antagonist small molecules—British Journal of Pharmacology (2006) 148, 619-628) disclose the pharmacology of a novel small-molecule agonist of GPR40 together with a selective antagonist of GPR40. Using these compounds, the authors verify that the potentiation of insulin secretion by fatty acids appears to be mediated at least partially through GPR40, and that GPR40 agonists can function as glucose-sensitive secretagogues in vitro.

Garrido et al. (Synthesis and activity of small molecule GPR40 agonists—Bioorganic & Medicinal Chemistry Letters (2006) 16, 1840-1845) and McKeown et al (Solid phase synthesis and SAR of small molecule agonists for the GPR40 receptor—Bioorganic & Medicinal Chemistry Letters (2007) 17, 1584-1589) focus on small molecule GPR40 receptor agonists and antagonists to investigate their potential as drugs for type 2 diabetes. The data gathered in the present work suggest that a small molecule GPR40 ligand could help regulate insulin secretion and as such present GPR40 as a potential target for Type II Diabetes.

Tan et al. (Selective small-molecule agonists of G protein-coupled receptor 40 promote glucose-dependent insulin secretion and reduce blood glucose in mice—Diabetes (2008) 57, 2211-2219) studied three new selective GPR40 agonists in wild-type and GPR40 knock-out mice in acute and chronic studies, and concluded that GPR40 does not mediate the chronic toxic effect of free fatty acids on pancreatic islet function, but potentiate GSIS after both acute and chronic administration, and may therefore be of potential benefit for control of type 2 diabetes also in humans.

However, none of the documents disclose the compounds of the present invention.

SUMMARY OF THE INVENTION

Provided herein are compounds, pharmaceutical compositions and methods useful for treating or preventing a condition or disorder such as type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer or edema.

In one aspect the present invention provides a compound of the formula (I)

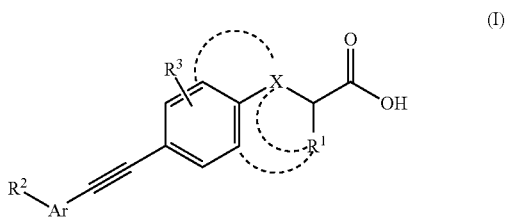

or a salt thereof
wherein
Ar is an optionally substituted monocyclic or fused aromatic or heteroaromatic ring system;
X is —C(R$^4$R$^5$)—, —N(R$^4$)—, —O—, or —S(O)$_n$—;
n is an integer of 0-2;
R$^1$, R$^2$, R$^3$, R$^4$, and R$^6$ are independently selected from the group consisting of hydrogen, (C$_1$-C$_{10}$)alkyl, (C$_2$-C$_{10}$)alkenyl, (C$_2$-C$_{10}$)alkynyl, (C$_1$-C$_{10}$)alkylene, (C$_1$-C$_{10}$)alkoxy, (C$_2$-C$_{10}$)dialkylamino, (C$_1$-C$_{10}$)alkylthio, (C$_2$-C$_{10}$)heteroalkyl, (C$_2$-C$_{10}$)heteroalkylene, (C$_3$-C$_{10}$)cycloalkyl, (C$_3$-C$_{10}$)heterocycloalkyl, (C$_3$-C$_{10}$)cycloalkylene, (C$_3$-C$_{10}$)heterocycloalkylene, halo, (C$_1$-C$_{10}$)haloalkyl, (C$_1$-C$_{10}$)perhaloalkyl, optionally substituted aryl, optionally substituted heteroaryl, and optionally substituted arylalkyl;
R$^2$ may be further substituted by R$^6$;
R$^5$ is selected from hydrogen and optionally substituted (C$_1$-C$_3$)alkyl;
- - - - - define that R$^1$ and R$^4$, when not selected from halo, may optionally be connected to the benzene ring in ortho position relative to X, to R$^3$, to X or to each other by a covalent bond, —O—, or —S(O)$_n$—.
Preferably X is —C(R$^4$R$^5$)—. It is also preferred that R$^1$, R$^4$ and R$^5$ are independently selected from hydrogen and (C$_1$-C$_3$)alkyl. In another preferred embodiment of the invention R$^1$ is hydrogen. Compounds, wherein R$^4$ and R$^5$ are hydrogen, are also preferred. Preferably R$^3$ is selected from hydrogen and halogen.

Concerning Ar this is preferably selected from the group consisting of an optionally substituted benzene, pyridine, thiophene, thiazole, furan, oxazole, pyrrole, pyrrazole, pyrimidine, triazole, tetrazole, naphthalene, quinoline, and indole. In a particularly preferred embodiment Ar is benzene or pyridine.

Preferably R$^2$ is substituted in the ortho or meta position relative to the alkyne. In a particularly preferred embodiment R$^2$ is selected from hydrogen and (C$_1$-C$_6$)alkyl.

Due to prior art the following compounds are excluded from protection:
2-[4-[2-(4-methylphenyl)ethynyl]phenoxy]-acetic acid,
4-[2-(1-pyrenyl)ethynyl]-benzenepropanoic acid,
4-[2-[4-(carboxymethoxy)phenyl]ethynyl]-2,6-Pyridinedicarboxylic acid, N,N'-[[4-[[4-(carboxymethoxy)phenyl]ethynyl]-2,6-pyridinediyl]bis(methylene)]bis[N-[2-(1,1-dimethylethoxy)-2-oxoethyl]-glycine,
N,N'-[[4-[[4-(carboxymethoxy)phenyl]ethynyl]-2,6-pyridinediyl]bis(methylene)]bis[N-[2-(1,1-dimethylethoxy)-2-oxoethyl]-glycine 1,1'-bis(1,1-dimethylethyl) ester,
2-[4-(2-phenylethynyl)phenoxy]-acetic acid,
N-[4-[[5-[(2,4-diamino-5-pyrimidinyl)methyl]-2,3-dimethoxyphenyl]ethynyl]phenyl]-N-[(trifluoromethyl)sulfonyl]-glycine,
4-[[6-amino-9-(N-ethyl-β-D-ribofuranuronamidosyl)-9H-purin-2-yl]ethynyl]-benzenepropanoic acid,
4-[2-[4-amino-7-[2-deoxy-5-O-[hydroxy[[hydroxy(phosphonooxy)phosphinyl]oxy]-phosphinyl]-β-D-erythro-pentofuranosyl]-7H-pyrrolo[2,3-d]pyrimidin-5-yl]ethynyl]-L-phenylalanine,
4-[2-[6-amino-9-[2-deoxy-5-O-[hydroxy[[hydroxy(phosphonooxy)phosphinyl]oxy]-phosphinyl]-β-D-erythro-pentofuranosyl]-9H-purin-8-yl]ethynyl]-L-phenylalanine,
4-[2-[4-amino-7-(2-deoxy-β-D-erythro-pentofuranosyl)-7H-pyrrolo[2,3-d]pyrimidin-6-yl]ethynyl]-L-phenylalanine,
[2-[6-amino-9-(2-deoxy-β-D-erythro-pentofuranosyl)-9H-purin-8-yl]ethynyl]-L-phenylalanine, and
2-[4-[2-(4-cyclobutyl-2-thiazolyl)ethynyl]-2-(2H-tetrazol-5-yl)phenoxy]-acetic acid.

Preferred compounds of the present invention are:
2-(4-(Phenylethynyl)phenoxy)acetic acid,
2-(4-(o-Tolylethynyl)phenoxy)acetic acid,
2-(4-(m-Tolylethynyl)phenoxy)acetic acid,
3-(4-(Phenylethynyl)phenyl)propanoic acid,
3-(4-(1-Naphthylethynyl)phenyl)propanoic acid,
3-(4-(m-Tolylethynyl)phenyl)propanoic acid,
3-(4-((3-(Hydroxymethyl)phenyl)ethynyl)phenyl)propanoic acid,
3-(4-(o-Tolylethynyl)phenyl)propanoic acid,
3-(4-(m-Tolylethynyl)phenyl)propanoic acid,
3-(4-((3-Cyanophenyl)ethynyl)phenyl)propanoic acid,
3-(4-((3-Nitrophenyl)ethynyl)phenyl)propanoic acid,
3-(4-((3-formylphenyl)ethynyl)phenyl)propanoic acid,
3-(4-((3-(Trifluoromethyl)phenyl)ethynyl)phenyl)propanoic acid,
3-(4-((3,5-Dimethylphenyl)ethynyl)phenyl)propanoic acid,
3-(4-((2,3-Dimethylphenyl)ethynyl)phenyl)propanoic acid,
3-(4-((3-Aminophenyl)ethynyl)phenyl)propanoic acid,
3-(4-((3-Ethynylphenyl)ethynyl)phenyl)propanoic acid,
3-(4-((3-(1-Benzyl-1H-1,2,3-triazol-4-yl)phenyl)ethynyl)phenyl)propanoic acid,
3-(4-(Pyridin-2-ylethynyl)phenyl)propanoic acid,
3-(4-(Pyridin-3-ylethynyl)phenyl)propanoic acid,
3-(4-((2-Chloropyridin-4-yl)ethynyl)phenyl)propanoic acid,
3-(4-((6-Methylpyridin-2-yl)ethynyl)phenyl)propanoic acid,
2-(4-((3-Hydroxyphenyl)ethynyl)phenoxy)ethanoic acid,
2-(4-((4-Hydroxyphenyl)ethynyl)phenoxy)ethanoic acid,
2-(4-((4-(Hydroxymethyl)phenyl)ethynyl)phenoxy)ethanoic acid,
3-(4-((7-chloroquinolin-4-yl)ethynyl)phenyl)propanoic acid,
3-(4-((2-(cyanomethyl)phenyl)ethynyl)phenyl)propanoic acid,
trans-2-(4-(phenylethynyl)phenyl)cyclopropanecarboxylic acid,
3-(4-((2-ethylphenyl)ethynyl)phenyl)propanoic acid,
3-(4-((2,5-dimethylphenyl)ethynyl)phenyl)propanoic acid,
3-(4-((2-methylpyridin-4-yl)ethynyl)phenyl)propanoic acid,
3-(4-((2,6-dichloropyridin-4-yl)ethynyl)phenyl)propanoic acid,
3-(4-((3-nitropyridin-2-yl)ethynyl)phenyl)propanoic acid,
2-(4-((2,6-dichloropyridin-4-yl)ethynyl)phenyl)cyclopropanecarboxylic acid,
2-(4-(o-tolylethynyl)phenyl)cyclopropanecarboxylic acid,
2-(4-(m-tolylethynyl)phenyl)cyclopropanecarboxylic acid,
2-(4-(p-tolylethynyl)phenyl)cyclopropanecarboxylic acid,
3-(4-((2-bromophenyl)ethynyl)phenyl)propanoic acid,
3-(4-(biphenyl-2-ylethynyl)phenyl)propanoic acid,
3-(4-((1-oxo-2,3-dihydro-1H-inden-4-yl)ethynyl)phenyl)propanoic acid,
3-(4-((3-(isocyanomethyl)phenyl)ethynyl)phenyl)propanoic acid,
3-(4-(pyridin-4-ylethynyl)phenyl)propanoic acid,
3-(4-((2-phenylpyridin-4-yl)ethynyl)phenyl)propanoic acid,
3-(4-((2-o-tolylpyridin-4-yl)ethynyl)phenyl)propanoic acid,
3-(4-(thiazol-5-ylethynyl)phenyl)propanoic acid,
3-(4-(thiophen-2-ylethynyl)phenyl)propanoic acid,
3-(4-((3-methylthiophen-2-yl)ethynyl)phenyl)propanoic acid,
3-(4-((2-chlorophenyl)etnynyl)phenyl)propanoic acid,
3-(4-((2,6-dimethylphenyl)etnynyl)phenyl)propanoic acid,
3-(4-((2-methoxyphenyl)ethynyl)phenyl)acid,
3-(4-((3-hydroxyphenyl)ethynyl)phenyl)propanoic acid,
3-(4-((2-acetylphenyl)ethynyl)phenyl)propanoic acid,
3-(4-((3-methoxyphenyl)ethynyl)phenyl)propanoic acid,
3-(4-((3-(benzyloxy)phenyl)ethynyl)phenyl)propanoic acid,
3-(4-((3-(prop-2-ynyloxy)phenyl)ethynyl)phenyl)propanoic acid,
3-(4-((3-(allyloxy)phenyl)ethynyl)phenyl)propanoic acid,
3-(4-((2-hydroxyphenyl)ethynyl)phenyl)propanoic acid,
3-(4-((2-hydroxymethyl)phenyl)ethynyl)phenyl)propanoic acid, and
3-(4-((2-(2-hydroxyethyl)phenyl)ethynyl)phenyl)propanoic acid, In some embodiments, a compound of the present invention comprise a stereomerically pure S-enantiomer. In other embodiments, the compound comprises a stereomerically pure R-enantiomer. In yet other embodiments, the compound comprises a mixture of S- and R-enantiomers.

In another aspect, the invention provides pharmaceutical compositions comprising a pharmaceutically acceptable carrier, diluent, or excipient, and a compound of any of the embodiments of the invention. According to a preferred embodiment there is provided compounds of the present invention for use as medicaments.

In another aspect, the invention provides methods for treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, hypertension, cancer, and edema. Such methods include administering to a subject in need thereof, a therapeutically effective amount of a compound of any of the embodiments. In some such embodiments, the disease or condition is type II diabetes.

In some embodiments, a compound of any of the embodiments is administered with combination with a second therapeutic agent. In some such embodiments, the second therapeutic agent is metformin or is a thiazolidinedione. The second therapeutic agent may be administered before, during, or after administration of the compound of any of the embodiments.

In another aspect, the invention provides methods for treating or preventing a disease or condition responsive to the modulation of GPR40. Such methods include administering to a subject in need thereof, a therapeutically effective amount of a compound of any of the embodiments.

In another aspect, the invention provides methods for treating or preventing a disease or condition mediated, regulated, or influenced by pancreatic beta-cells. Such methods include administering to a subject in need thereof, a therapeutically effective amount of a compound of any of the embodiments.

In another aspect, the invention provides methods for modulating GPR40 function in a cell. Such methods include contacting a cell with a compound of formula any of the embodiments.

In another aspect, the invention provides methods for modulating GPR40 function. Such methods include contacting GPR40 with a compound of any of the embodiments.

In another aspect, the invention provides methods for modulating circulating insulin concentration in a subject. Such methods include administering a compound of any of the embodiments to the subject. In some such embodiments, the circulating insulin concentration is increased in the subject after administration whereas in other such embodiments, the circulating insulin concentration is decreased in the subject after administration.

In another aspect, the invention provides the use of a compound of any of the embodiments for treating a disease or condition or for preparing a medicament for treating a disease or condition where the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer, and edema. In some such embodiments, the disease or condition is type II diabetes. The compounds of the invention may also be used to prepare medicaments that include a second therapeutic agent such as metformin or a thiazolidinedione.

In another aspect, the invention provides the use of a compound of any of the embodiments for modulating GPR40 or for use in the preparation of a medicament for modulating GPR40.

In another aspect, the invention provides a therapeutic composition that includes a compound of any of the embodiments and a second therapeutic agent such as those described herein, for example, metformin or a thiazolidinedione, as a combined preparation for simultaneous, separate, or sequential use in the treatment of a disease or condition mediated by GPR40. In some such embodiments, the disease or condition is type II diabetes. In some embodiments, the compound of any of the embodiments and the second therapeutic agent are provided as a single composition, whereas in other embodiments they are provided separately as parts of a kit.

DETAILED DESCRIPTION OF THE INVENTION

The terms "treat", "treating" and "treatment", as used herein, are meant to include alleviating or abrogating a condition or disease and/or its attendant symptoms. The terms "prevent", "preventing" and "prevention", as used herein, refer to a method of delaying or precluding the onset of a condition or disease and/or its attendant symptoms, barring a subject from acquiring a condition or disease, or reducing a subject's risk of acquiring a condition or disease.

The term "therapeutically effective amount" refers to that amount of the compound that will elicit the biological or medical response of a tissue, system, or subject that is being sought. The term "therapeutically effective amount" includes that amount of a compound that, when administered, is sufficient to prevent development of, or alleviate to some extent, one or more of the symptoms of the condition or disorder being treated in a subject. The therapeutically effective amount in a subject will vary depending on the compound, the disease and its severity, and the age, weight, etc., of the subject to be treated.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "modulate", "modulation" and the like refer to the ability of a compound to increase or decrease the function or activity of GPR40 either directly or indirectly. Inhibitors are compounds that, for example, bind to, partially or totally block stimulation, decrease, prevent, delay activation, inactivate, desensitize, or down regulate signal transduction, such as, for instance, antagonists. Activators are compounds that, for example, bind to, stimulate, increase, activate, facilitate, enhance activation, sensitize or up regulate signal transduction, such as agonists for instance. Modulation may occur in vitro or in vivo.

As used herein, the phrases "GPR40-mediated condition or disorder", "disease or condition mediated by GPR40", and the like refer to a condition or disorder characterized by inappropriate, for example, less than or greater than normal, GPR40 activity. A GPR40-mediated condition or disorder may be completely or partially mediated by inappropriate GPR40 activity.

However, a GPR40-mediated condition or disorder is one in which modulation of GPR40 results in some effect on the underlying condition or disease (e.g., a GPR40 modulator results in some improvement in patient well-being in at least some patients). Exemplary GPR40-mediated conditions and disorders include cancer and metabolic disorders, e.g., diabetes, type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, ketoacidosis, hypoglycemia, thrombotic disorders, metabolic syndrome, syndrome X and related disorders, e.g., cardiovascular disease, atherosclerosis, kidney disease, nephropathy, diabetic neuropathy, diabetic retinopathy, sexual dysfunction, dermatopathy, dyspepsia, and edema.

The term "alkyl", by itself or as part of another substituent, means, unless otherwise stated, a straight or branched chain, or cyclic hydrocarbon radical, or combination thereof, which is fully saturated, having the number of carbon atoms designated (e.g., C1-C10 means one to ten carbons). Examples of alkyl groups include methyl, ethyl, n-propyl, isopropyl, n-butyl, t-butyl, isobutyl, sec-butyl, cyclohexyl, (cyclohexyl)methyl, cyclopropyl, cyclopropylmethyl, and homologs and isomers of, for example, n-pentyl, n-hexyl, n-heptyl, n-octyl, and the like.

The term "alkenyl", by itself or as part of another substituent, means a straight or branched chain, or cyclic hydrocarbon radical, or combination thereof, which may be mono- or polyunsaturated, having the number of carbon atoms designated (i.e., $C_2$-$C_8$ means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl), and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e., $C_2$-$C_8$ means two to eight carbons) and one or more triple bonds. Examples of alkynyl groups include ethynyl, 1- and 3-propynyl, 3-butynyl, and higher homologs and isomers thereof.

The term "alkylene" by itself or as part of another substituent means a divalent radical derived from alkyl, as exemplified by —$CH_2CH_2CH_2CH_2$—. The two valences may be on any carbon atom of the chain, including on the same carbon, resulting in an alkyl connected by a double bond. Typically, an alkyl (or alkylene) group will have from 1 to 24 carbon atoms, with those groups having 12 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Similarly, the term dialkylamino refers to an amino group having two attached alkyl groups. The alkyl groups of a dialkylamino may be the same or different.

The term "heteroalkyl," by itself or in combination with another term, means, unless otherwise stated, a stable straight or branched chain, or cyclic hydrocarbon radical, or combinations thereof, consisting of carbon atoms and from one to three heteroatoms selected from the group consisting of O, N, and S, and wherein the nitrogen and sulfur atoms may optionally be oxidized, and the nitrogen heteroatom may optionally be quaternized. The heteroatom(s) O, N, and S may be placed at any position of the heteroalkyl group. Examples include —$CH_2CH_2OCH_3$, —$CH_2CH_2NHCH_3$, —$CH_2CH_2N(CH_3)CH_3$, —$CH_2SCH_2CH_3$, —$CH_2CH_2S(O)CH_3$, —$CH_2CH_2S(O)_2CH_3$, and —$CH_2CH=N$—$OCH_3$. Up to two heteroatoms may be consecutive, such as, for example, —$CH_2NH$—$OCH_3$. When a prefix such as ($C_2$-$C_8$) is used to refer to a heteroalkyl group, the number of carbons (2 to 8, in this example) is meant to include the heteroatoms as well. For example, a $C_2$-heteroalkyl group is meant to include, for example, —$CH_2OH$ (one carbon atom and one heteroatom replacing a carbon atom) and —$CH_2SH$.

To further illustrate the definition of a heteroalkyl group, where the heteroatom is oxygen, a heteroalkyl group is an, oxyalkyl group. For instance, ($C_2$-$C_8$)oxyalkyl is meant to include, for example —$CH_2O$—$CH_3$ (a $C_2$-oxyalkyl group with two carbon atoms and one oxygen replacing a carbon atom), —$CH_2CH_2CH_2CH_2OH$, and the like.

The term "heteroalkylene" by itself or as part of another substituent means a divalent radical derived from heteroalkyl, as exemplified by —$CH_2CH_2SCH_2CH_2$— and —$CH_2SCH_2$—$CH_2NHCH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied. Heteroalkylene groups such as oxymethyl groups (—$CH_2O$—) may be substituted or unsubstituted. In some embodiments, heteroalkylene groups may be substituted with an alkyl group. For example, the carbon atom of an oxymethylene group may be substituted with a methyl group in a group of formula —$CH(CH_3)O$—.

The terms "cycloalkyl" and "heterocycloalkyl" by themselves or in combination with other terms, represent, unless otherwise stated, cyclic versions of "alkyl" and "heteroalkyl" respectively. Thus, the terms "cycloalkyl" and "heterocycloalkyl" are meant to be included in the terms "alkyl" and "heteroalkyl," respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, 4,5-dihydroisoxazol-3-yl, and the like. The term "heterocycloalkyl" includes fully saturated compounds such as piperidine and compounds with partial saturation that are not aromatic. Examples of such groups include, but are not limited to, an imidazole, oxazole, or isoxazole which has been partially hydrogenated so that it only contains one double bond.

The term "cycloalkylene" and "heterocycloalkylene," by themselves or in combination with other terms, represent, unless otherwise stated, cyclic versions of "alkylene" and "heteroalkylene," respectively. Thus, the terms "cycloalkylene" and "heterocycloalkylene" are meant to be included in the terms "alkylene" and "heteroalkylene," respectively. Additionally, for heterocycloalkylene, one or more heteroatoms can occupy positions at which the heterocycle is attached to the remainder of the molecule. Typically, a cycloalkylene or heterocycloalkylene will have from 3 to 9 atoms forming the ring, more typically, 4 to 7 atoms forming the ring, and even more typically, 5 or 6 atoms will form the cycloalkylene or heterocycloalkylene ring.

The terms "halo" or "halogen," by themselves or as part of another substituent, mean, unless otherwise stated, a fluorine, chlorine, bromine, or iodine atom. Additionally, terms such as "haloalkyl", are meant to include alkyl substituted with halogen atoms which can be the same or different, in a number ranging from one to (2m+1), where m is the total number of carbon atoms in the alkyl group. For example, the term "halo ($C_1$-$C_4$)alkyl" is meant to include trifluoromethyl, 2,2,2-trifluoroethyl, 4-chlorobutyl, 3-bromopropyl, and the like.

Thus, the term "haloalkyl" includes monohaloalkyl (alkyl substituted with one halogen atom) and polyhaloalkyl (alkyl substituted with halogen atoms in a number ranging from two to (2m+1) halogen atoms). The term "perhaloalkyl" means, unless otherwise stated, alkyl substituted with (2m+1) halogen atoms, where m is the total number of carbon atoms in the alkyl group. For example, the term "perhalo(C1-C4)alkyl", is meant to include trifluoromethyl, pentachloroethyl, 1,1,1-trifluoro-2-bromo-2-chloroethyl, and the like.

The term "aryl" means, unless otherwise stated, a polyunsaturated, typically aromatic, hydrocarbon ring. The term "heteroaryl" refers to aryl groups (or rings) that contain from one to four heteroatoms selected from the group consisting of N, O and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl and 4-pyridazinyl.

The term "fused aryl" means, unless otherwise stated, an aryl which is fused with another cyclic aromatic or non-aromatic ring. The term "fused heteroaryl" means, unless otherwise stated, a heteroaryl which is fused with another cyclic aromatic or non-aromatic ring. Examples of fused aryl and fused heteroaryl groups include 1-naphthyl, 2-naphthyl, 4-biphenyl, dibenzofuryl, 5-benzothiazolyl, 2-benzoxazolyl, 5-benzoxazolyl, benzooxadiazolyl, purinyl, 2-benzimidazolyl, 5-indolyl, 1H-indazolyl, carbazolyl, carbolinyl, 1-isoquinolyl, 5-isoquinolyl, 2-quinoxalinyl, 5-quinoxalinyl, 2-quinolyl, 3-quinolyl, 4-quinolyl, 5-quinolyl, 6-quinolyl, 7-quinolyl, and 8-quinolyl.

Preferably, the term "aryl" refers to a phenyl group which is unsubstituted or substituted. Preferably, the term "heteroaryl" refers to a pyrrolyl, pyrazolyl, imidazolyl, pyrazinyl, oxazolyl, oxadiazolyl, isoxazolyl, thiazolyl, furyl, thienyl (thiophenyl), pyridyl, or pyrimidyl which is substituted or unsubstituted. Preferably, the term "fused aryl refers to naphthyl, indanyl, indenyl, or quinolyl. Preferably, the term "fused heteroaryl" refers to quinolyl, benzothiazolyl, purinyl, benzimidazolyl, indolyl, isoquinolyl, triazolyl, tetrazolyl, or quinoxalinyl group which is unsubstituted or substituted.

Each of the above terms (e.g., "alkyl," "heteroalkyl," "aryl" and "heteroaryl") is meant to include both substituted and unsubstituted forms of the indicated radical, unless otherwise indicated. Preferred substituents for each type of radical are provided below.

The term "substituent", which may be present on alkyl or heteroalkyl radicals, as well as those groups referred to as alkylene, alkenyl, heteroalkylene, heteroalkenyl, alkynyl, cycloalkyl, heterocycloalkyl, cycloalkenyl and heterocycloalkenyl, or on other groups indicated as "optionally substituted", can be a variety of groups selected from: —OR', =O, =NR', =N—OR', —NR'R", —SR', halogen, —OC(O)R', —C(O)R', —CONR'R", —OC(O)NR'R", —NR"C(O)R', —NR'—C(O)NR"R''', —NR'—SO$_2$NR"R''', —NR"CO$_2$R', —NH—C(NH$_2$)=NH, —NR'C(NH$_2$)=NH, —NH—C(NH$_2$)=NR', —S(O)R', —SO$_2$R', —SO$_2$NR"R", —NR"SO$_2$R, —CN, —(C$_2$-C$_5$)alkynyl, —(C$_2$-C$_5$)alkenyl, and —NO$_2$, in a number ranging from zero to three, with those groups having zero, one or two substituents being particularly preferred. Other suitable substituents include aryl and heteroaryl groups. R', R" and R''' each independently refer to hydrogen, unsubstituted (C$_1$-C$_6$)alkyl and (C$_2$-C$_6$) heteroalkyl, unsubstituted aryl, aryl substituted with one to three halogens, unsubstituted (C$_1$-C$_4$)alkyl, (C$_1$-C$_4$)-alkoxy or (C$_1$-C$_4$)-thioalkoxy groups, halo(C$_1$-C$_4$)alkyl, or aryl-(C$_1$-C$_4$)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl.

Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF$_3$ and —CH$_2$CF$_3$).

Preferred substituents for the alkyl and heteroalkyl radicals are selected from: —OR', =O, —NR'R", —SR', halogen, —OC(O)R', —C(O)R', —CO$_2$R', —CONR'R", —OC(O)NR'R", —NR"C(O)R', —NR"CO$_2$R', —NR'SO$_2$NR"R''', —S(O)R', —SO$_2$R', —SO$_2$NR'R", —NR"SO$_2$R, —CN, —(C$_2$-C$_5$)alkynyl, —(C$_2$-C$_5$)alkenyl and —NO$_2$, where R' and R" are as defined above. Further preferred substituents are selected from: —OR', =O, —NR'R", halogen, —OC(O)R', —CO$_2$R', —CONR'R", —OC(O)NR'R", —NR"C(O)R', —NR'CO$_2$R', —NR'—SO$_2$NR"R''', —SO$_2$R', —SO$_2$NR'R", —NR"SO$_2$R, —CN, —(C$_2$-C$_5$)alkynyl, —(C$_2$-C$_5$)alkenyl, and —NO$_2$.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NHC(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R''' are independently selected from hydrogen, (C$_1$-C$_4$)alkyl and heteroalkyl, unsubstituted aryl and heteroaryl, (unsubstituted aryl)-(C$_1$-C$_4$)alkyl, (unsubstituted aryl)oxy-(C$_1$-C$_4$)alkyl, —C$_2$-C$_5$) alkynyl, and —(C$_2$-C$_5$)alkenyl.

As used herein, the term "benzo-fused cycloalkane ring" is meant to include bicyclic structures in which benzene is fused with a cycloalkane (or cycloheteroalkane).

As used herein, the term "heterobenzo-fused (C$_5$-C$_8$)cycloalkane ring" has the same meaning as "benzo-fused (C$_5$-C$_8$)cycloalkane ring" except the benzene of the benzo-fused (C$_5$-C$_8$)cycloalkane ring is replaced with a six-membered heteroaryl ring comprising 1 or 2 nitrogen (N) atoms. The (C$_5$-C$_8$)cycloalkane of benzo-fused (C$_5$-C8)cycloalkane rings and heterobenzo-fused (C$_5$-C$_8$)cycloalkane ring may include only carbon atoms, but may also include one or more heteroatoms. Such heteroatoms typically are selected from O, N, or S.

As used herein, the term "heteroatom" is meant to include oxygen (O), nitrogen (N), and sulfur (S).

The term "pharmaceutically acceptable salt" is meant to include a salt of the active compound which is prepared with relatively nontoxic acids or bases, depending on the particular substituents found on the compound described herein. When a compound of the invention contains relatively acidic functionalities, a base addition salt can be obtained by contacting the neutral form of such compound with a sufficient amount of the desired base, either neat or in a suitable inert solvent. Examples of pharmaceutically acceptable base addition salts include sodium, potassium, calcium, ammonium, organic amino, or magnesium salt, or a similar salt. When a compound of the invention contains relatively basic functionalities, an acid addition salt can be obtained by contacting the neutral form of such compound with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginine and the like, and salts of organic acids like glucuronic or galacturonic acids and the like (see, for example, Berge et al. (1977) J. Pharm. Sci. 66:1-19). Certain specific compounds of the invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that readily undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not.

The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. Additional examples include peptidyl derivatives of a compound.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed.

Various compounds of the invention contain one or more chiral centers, and can exist as racemic mixtures of enantiomers, mixtures of diastereomers or enantiomerically or optically pure compounds. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (EX. Eliel, Ed., Univ. of Notre Dame Press, Notre Dame, Ind., 1972).

In one aspect, a class of compounds that modulates GPR40 is described herein. Depending on the biological environment (e.g., cell type, pathological condition of the subject, etc.), these compounds can modulate, e.g., activate or inhibit, the actions of GPR40. By modulating GPR40, the compounds find use as therapeutic agents capable of regulating insulin levels in a subject.

The compounds find use as therapeutic agents for modulating diseases and conditions responsive to modulation of GPR40 and/or mediated by GPR40 and/or mediated by pancreatic beta-cells. As noted above, examples of such diseases and conditions include diabetes, obesity, hyperglycemia, glucose intolerance, insulin resistance, cancer, hyperinsulinemia, hypercholesterolemia, hypertension, hyperlipoproteinemia, hyperlipidemia, hypertriglylceridemia, dyslipidemia, ketoacidosis, hypoglycemia, metabolic syndrome, syndrome X, cardiovascular disease, atherosclerosis, kidney disease, nephropathy, thrombotic disorders, diabetic neuropathy, diabetic retinopathy, dermatopathy, dyspepsia and edema.

Additionally, the compounds are useful for the treatment and/or prevention of complications of these diseases and disorders (e.g., type II diabetes, sexual dysfunction, dyspepsia and so forth).

While the compounds of the invention are believed to exert their effects by interacting with GPR40, the mechanism of action by which the compounds act is not a limiting embodiment of the invention.

Compounds contemplated by the invention include, but are not limited to, the exemplary compounds provided herein.

In another aspect, the invention provides pharmaceutical compositions suitable for pharmaceutical use comprising one or more compounds of the invention and a pharmaceutically acceptable carrier, excipient, or diluent.

The term "composition" as used herein is intended to encompass a product comprising the specified ingredients (and in the specified amounts, if indicated), as well as any product which results, directly or indirectly, from combination of the specified ingredients in the specified amounts.

By "pharmaceutically acceptable" it is meant that the carrier, excipient, or diluent is compatible with the other ingredients of the formulation and is not deleterious to the recipient thereof.

Composition formulation may improve one or more pharmacokinetic properties (e.g., oral bioavailability, membrane permeability) of a compound of the invention (herein referred to as the active ingredient).

The pharmaceutical compositions for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations.

Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The pharmaceutical compositions and methods of the invention may further comprise other therapeutically active compounds, as noted herein, useful in the treatment of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In another aspect, the invention provides methods of treating or preventing a disease or condition selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema, comprising administering to a subject in need thereof a therapeutically effective amount of a compound or composition of the invention.

In one embodiment, the disease or condition is type II diabetes.

In another aspect, the present invention provides a method for treating a disease or condition responsive to the modulation of GPR40 comprising administering to a subject in need thereof a therapeutically effective amount of a compound or composition of the invention.

In some embodiments, the disease or condition is selected from the group consisting of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema.

In certain embodiments, a cell to be contacted can be made to express or overexpress GPR40, for example, by expressing GPR40 from heterologous nucleic acid introduced into the cell or, as another example, by upregulating the expression of GPR40 from nucleic acid endogenous to the cell.

Depending on the disease to be treated and the subject's condition, the compounds of the invention may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration and may be formulated, alone or together, in suitable dosage unit formulations containing conventional non-toxic pharmaceutically acceptable carriers, adjuvants and vehicles appropriate for each route of administration.

The invention also contemplates administration of the compounds of the invention in a depot formulation, in which the active ingredient is released over a defined time period.

In the treatment or prevention of type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema or other conditions or disorders associated with GPR40, an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range, the dosage may be 0.005 to 0.05, 0.05 to 0.5 or 0.5 to 5.0 mg/kg per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention can be combined or used in combination with other agents useful in the treatment, prevention, suppression or amelioration of the diseases or conditions for which compounds of the invention are useful, including type II diabetes, obesity, hyperglycemia, glucose intolerance, insulin resistance, hyperinsulinemia, hypercholesterolemia, hypertension, hyperlipoproteinemia, hyperlipidemia, hypertriglylceridemia, dyslipidemia, metabolic syndrome, syndrome X, cardiovascular disease, atherosclerosis, kidney disease, ketoacidosis, thrombotic disorders, nephropathy, diabetic neuropathy, diabetic retinopathy, sexual dysfunction, dermatopathy, dyspepsia, hypoglycemia, cancer and edema. Such other agents, or drugs, may be administered, by a route and in an amount commonly used therefore, simultaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients or therapeutic agents, in addition to a compound of the invention.

The compounds of the invention may be used in combination with a second therapeutic agent such as those described herein. Thus, in some embodiments, therapeutic compositions are provided that include a compound of the invention and a second therapeutic agent as a combined preparation for simultaneous, separate or sequential use in the treatment of a subject with a disease or condition mediated by GPR40. in some embodiments, therapeutic compositions are provided that include a compound of the invention and a second therapeutic agent as a combined preparation for simultaneous, separate or sequential use in the prophylactic treatment of a subject at risk for a disease or condition mediated by GPR40. In some such embodiments, the components are provided as a single composition. In other embodiments, the compound and the second therapeutic agent are provided separately as parts of a kit.

Examples of other therapeutic agents that may be combined with a compound of the invention, either administered separately or in the same pharmaceutical compositions, include, but are not limited to: (a) cholesterol lowering agents such as HMG-CoA reductase inhibitors (e.g., lovastatin, simvastatin, pravastatin, fluvastatin, atorvastatin and other statins), bile acid sequestrants (e.g., cholestyramine and colestipol), vitamin $B_3$ (also known as nicotinic acid, or niacin), vitamin $B_6$ (pyridoxine), vitamin $B_{12}$ (cyanocobalamin), fibric acid derivatives (e.g., gemfibrozil, clofibrate, fenofibrate and benzafibrate), probucol, nitroglycerin, and inhibitors of cholesterol absorption (e.g., beta-sitosterol and acyl-CoA-cholesterol acyltransferase (ACAT) inhibitors such as melinamide), HMG-CoA synthase inhibitors, squalene epoxidase inhibitors and squalene synthetase inhibitors; (b) antithrombotic agents, such as thrombolytic agents (e.g., streptokinase, alteplase, anistreplase and reteplase), heparin, hirudin and warfarin derivatives, beta-blockers (e.g., atenolol), beta-adrenergic agonists (e.g., isoproterenol), ACE inhibitors and vasodilators (e.g., sodium nitroprusside, nicardipine hydrochloride, nitroglycerin and enalopritat); and (c) anti-diabetic agents such as insulin and insulin mimetics, sulfonylureas (e.g., glyburide, meglinatide), biguanides, e.g., metformin (GLUCOPHAGE®), glucosidase inhibitors (acarbose), insulin sensitizers, e.g., thiazolidinone compounds, rosiglitazone (Avandia), troglitazone (Rezulin), ciglitazone, pioglitazone (ACTOS®) and englitazone, DPP-IV inhibitors, e.g., vildagliptin (Galvus®), sitagliptin (Januvia), and GLP-I analogs, e.g. exenatide (Byetta). In some embodiments, a compound of the invention may be administered along with a DPP-IV inhibitor or a GLP-I analog.

The weight ratio of the compound of the invention to the second active ingredient may be varied and will depend upon the effective dose of each ingredient. Generally, an effective dose of each will be used. Combinations of a compound of the invention and other active ingredients will generally also be within the aforementioned range, but in each case, an effective dose of each active ingredient should be used.

In another aspect, the present invention provides a method for modulating circulating insulin concentration in a subject, comprising administering a compound or composition of the invention.

EXAMPLES

There are multiple synthetic strategies for the synthesis of compounds (I), which all are known to persons skilled in the art of organic synthesis. Some useful general methods are outlined In the general synthetic methods outlined below, $R^1$, $R^2$, $R^3$ and - - - -, are as defined above, $R^7$ is typically methyl, ethyl, tert-butyl or hydrogen, and Y is typically iodo, bromo, chloro or triflate.

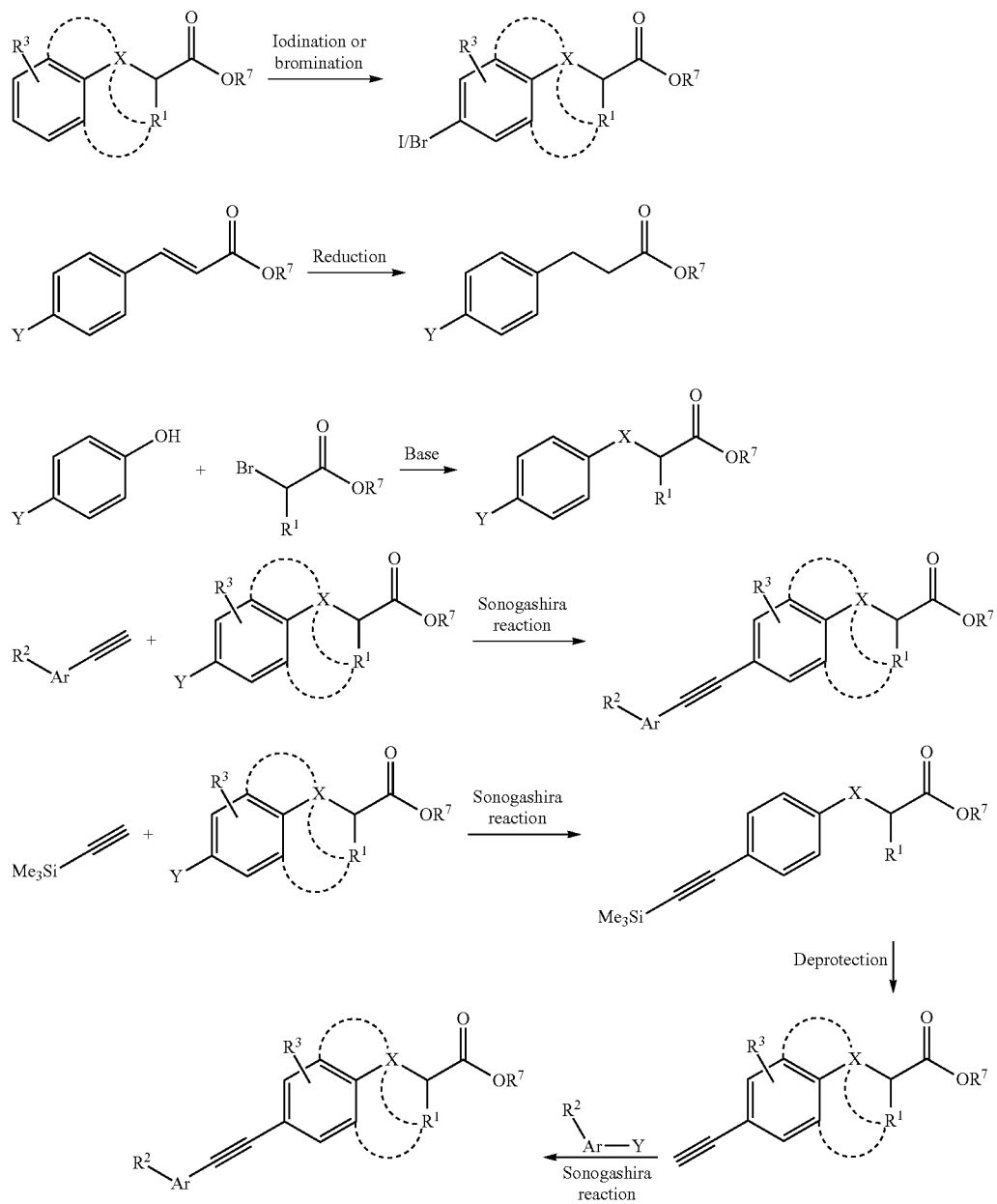

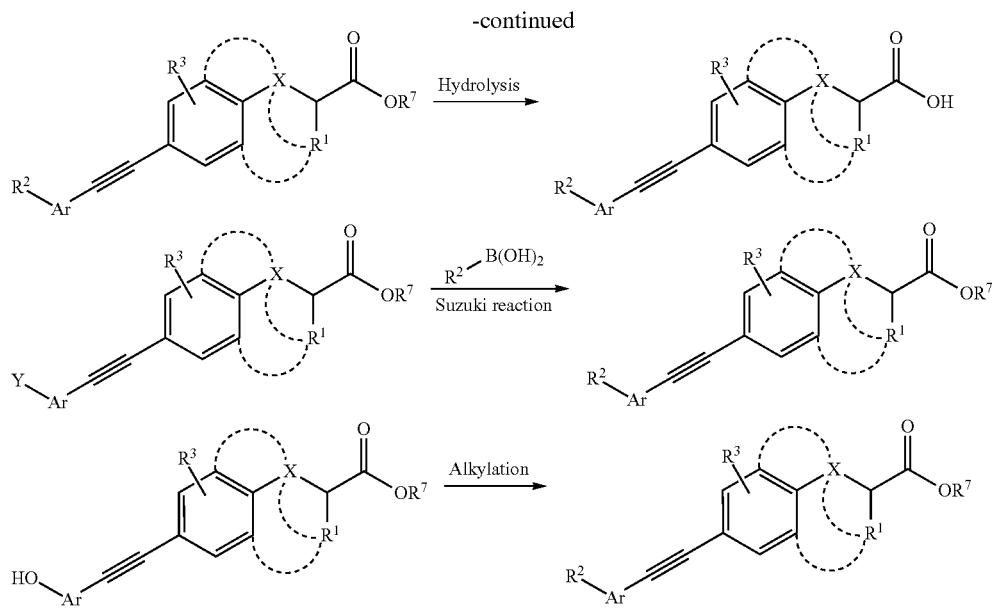

General Procedure IA for the Sonogashira Reaction

A dry Schlenk flask charged with aryl halide (1 equiv), CuI (0.02 equiv) and $Et_3N$ (3 equiv) dissolved in DMF (~10 mL/g aryl halide) under inert atmosphere added $Pd(PPh_3)_2Cl_2$ (0.01 equiv). The reaction was heated to 70° C. and the alkyne (1.1-2 equiv) was added before the temperature was elevated to 90° C. After consumption of the starting material, the reaction was cooled to room temperature added water and extracted with EtOAc. The organic phases were combined, washed with brine, dried over $MgSO_4$ and concentrated under vacuum and, if necessary, purification by flash chromatography.

General Procedure IB for the Sonogashira Reaction

A dry Schlenk flask charged with 3-(4-ethynylphenyl)propanoate (1 equiv), aryl halide (1.1 equiv), CuI (0.02 equiv) and $Et_3N$ (3 equiv) in DMF (~10 mL/g aryl halide) under inert atmosphere was added $Pd(PPh_3)_2Cl_2$ (0.01 equiv). The reaction was heated to 90° C. and stirred until consumption of the starting material as indicated by TLC. The reaction mixture was cooled to room temperature, added water, and extracted with EtOAc. The organic phases were combined, washed with brine, dried over $MgSO_4$ and concentrated under vacuum before purification by flash chromatography.

General Procedure IC for the Sonogashira Reaction

A dry Schlenk flask charged with phenyl acetylene (1 equiv), aryl halide (1.1 equiv), CuI (0.02 equiv) and $Et_3N$ (2.4 equiv) in DMF (~10 mL/g aryl halide) under inert atmosphere was added $Pd(PPh_3)_2Cl_2$ (0.01 equiv). The reaction was heated to 50° C. and stirred until consumption of the starting material indicated by TLC the reaction was cooled to room temperature, added water and extracted with EtOAc. The organic phases were combined, washed with brine and dried over $MgSO_4$ and concentrated under vacuum before purification by flash chromatography.

General Procedure ID for the Sonogashira Reaction

A dry Schlenk flask charged with phenyl acetylene (1 equiv) aryl iodide (1.5 equiv) and $Et_3N$ (3 equiv) in DMF (~10 mL/g aryl halide) under inert atmosphere was added CuI (0.5 equiv) and $Pd(PPh_3)_4$ (0.05 equiv). The flask was evacuated and filled with nitrogen, and the reaction mixture was stirred at room temperature until consumption of the starting material indicated by TLC. The reaction was neutralised with saturated ammonium chloride, added water and extracted with EtOAc. The organic phases were combined, washed with brine, dried over $MgSO_4$ and concentrated under vacuum before purification by flash chromatography.

General Procedure IE for the Sonogashira Reaction

A dry Schlenk flask charged with phenyl acetylene (1 equiv) aryl iodide (1 equiv) and DIPEA (2 equiv) in DMF (~10 mL/g aryl halide) under inert atmosphere was added CuI (0.25 equiv) and $Pd(PPh_3)_4$ (0.05 equiv). The flask was evacuated and filled with nitrogen, and the reaction mixture was stirred at room temperature until consumption of the starting material indicated by TLC. The reaction was neutralised with saturated ammonium chloride, added water and extracted with EtOAc. The organic phases were combined, washed with brine, dried over $MgSO_4$ and concentrated under vacuum before purification by flash chromatography.

General Procedure IF for the Sonogashira Reaction

A dry Schlenk flask was charged with $Na_2[PdCl_4]$ (1 mol %), 2-(di-tert-butylphosphino)-1-phenylindole (2 mol %), CuI (2 mol %), methyl 3-(4-ethynylphenyl)propanoate (1 equiv), tetramethylethylenediamine (2 mL/mmol) and aryl halide (1.1-1.5 equiv). The mixture was evacuated and back-filled with Ar (3×), and heated to 80° C. After consumption of the starting material, the reaction mixture was cooled to room temperature, quenched with water and extracted with EtOAc (3×). The combined extracts were washed with brine, dried over $MgSO_4$ and concentrated under vacuum and the residue was purified by flash chromatography.

General Procedure II: Ester Hydrolysis

A solution of the ester (1 equiv) in dioxane or THF (4 mL) was added a solution of $LiOH \cdot xH_2O$ (2-3 equiv) in $H_2O$ (2 mL). The reaction was stirred at room temperature until complete consumption of the starting material indicated by TLC, typically after 1-12 hours. The reaction was added water, acidified with 3% HCl until pH<1 and extracted with EtOAc. The organic phases were combined, washed with brine and dried over $MgSO_4$ before concentration to the corresponding acetylene propanoic acid.

General Procedure III for the Suzuki Reaction

A dry Schlenk flask charged with toluene (2 mL) and methyl 3-(4-((2-bromophenyl)ethynyl)phenyl)propanoate or (1 equiv, 0.20-0.27 mmol) was evacuated and backfilled with argon before addition of Pd(OAc)$_2$ (1 mol %), SPhos (2 mol %), K$_3$PO$_4$ (2 equiv) and phenylboronic acid (1.5 equiv). The reaction was evacuated and backfilled with argon and heated to 100° C. and stirred until consumption of the starting material indicated by TLC the reaction was cooled to room temperature before addition of H$_2$O and extracted with EtOAc. The organic phases were combined, washed with brine and dried over MgSO$_4$ and concentrated under vacuum before purification by flash chromatography.

General Procedure IV for Ether Synthesis

The phenol (1 equiv.) in acetone (~1 mL/10 mg) was added aryl halide (~1 equiv.) and K$_2$CO$_3$ (2 equiv.) and the reaction was stirred at room temperature until consumption of the starting materials monitored by TLC. The reaction was added H$_2$O and extracted with EtOAc before the organic phases were combined, washed with brine, dried over MgSO$_4$ and concentrated under vacuum to give the pure compound or subsequently purified by flash chromatography.

HPLC Method I

Dionex UltiMate 3000 system with Dionex Accalim 120 C18 column (5μ, 4.6×150 mm); flow: 1 mL/min; 10% acetonitrile in water (0-1 min), 10-100% acetonitrile in water (1-10 min), 100% acetonitrle (11-15 min), with both solvents containing 0.05% TFA as modifier; UV detection at 256 nm.

Example E1

Example A1

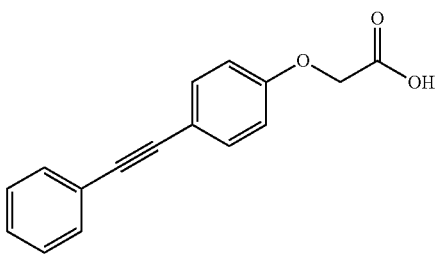

2-(4-(Phenylethynyl)phenoxy)acetic acid. The title compound was prepared from ethyl 2-(4-(phenylethynyl)phenoxy)acetate (54 mg, 0.19 mmol) according to the general procedure II to give 42 mg (87%) of the pure title compound as an yellow solid. R$_f$: 0.14 ([EtOAc with 5% AcOH]:hexanes, 1:1); $^1$HNMR (DMSO-d$_6$) δ 7.50-7.39 (m, 5H), 6.97-6.94 (m, 2H), 4.73 (s, 2H); $^{13}$CNMR (DMSO-d$_6$) δ 169.8, 158.3, 132.8, 131.1, 128.6, 128.3, 114.8, 114.6, 89.2, 88.0, 64.4; MALDI-HRMS calcd for C$_{16}$H$_{12}$O$_3$ (MNa$^+$): 275.0679. found: 275.0684.

Example E2

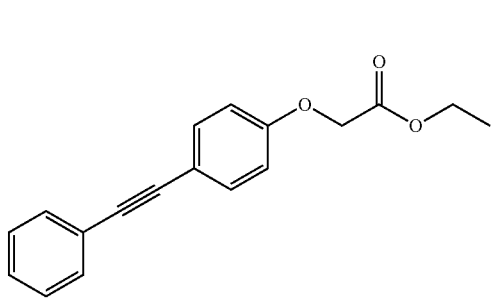 [SMILES: CCOC(=O)COc1ccc(C#Cc2ccccc2)cc1]

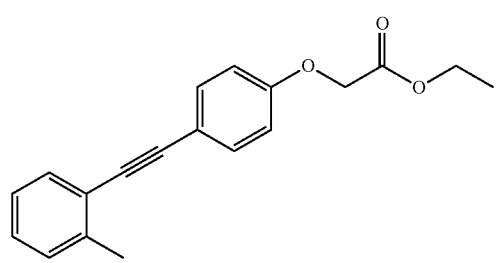 [SMILES: CCOC(=O)COc1ccc(C#Cc2ccccc2C)cc1]

Ethyl 2-(4-(phenylethynyl)phenoxy)acetate. The title compound was prepared from ethyl 2-(4-iodophenoxy)acetate (550 mg, 1.80 mmol) and phenylacetylene (0.17 mL, 1.80 mmol) according to the general procedure IE to give 390 mg (78%) of an orange solid after purification by flash chromatography (SiO$_2$, EtOAc/hexanes, 1:5). R$_f$: 0.26 (EtOAc: hexanes, 1:5); $^1$HNMR (CDCl$_3$) δ 7.53-7.45 (m, 4H), 7.36-7.25 (m, 3H), 6.90-6.87 (m, 2H), 4.63 (s, 2H), 4.32-4.23 (dq, 2H, J=7.2 Hz, 2.1 Hz), 1.35-1.24 (tt, 3H, J=7.2 Hz, 1.5 Hz); $^{13}$CNMR (CDCl$_3$) δ 168.6, 157.8, 133.1, 131.5, 128.3, 128.0, 123.4, 116.6, 114.7, 89.0, 88.4, 65.4, 61.5, 14.1; EI-MS m/z 280 (M$^+$).

Ethyl 2-(4-(o-tolylethynyl)phenoxy)acetate. The title compound was prepared from ethyl (4-ethynylphenoxy)acetate (42 mg, 0.21 mmol) and iodo-3-methylbenzene (0.03 mL, 0.20 mmol) according to the general procedure ID to give 43 mg (72%) of an orange oil after purification by flash chromatography (SiO$_2$, EtOAc/hexanes, 1:10). R$_f$: 0.22 (EtOAc:hexanes, 1:10); $^1$HNMR (CDCl$_3$) δ 7.49-7.46 (m, 3H), 7.26-7.12 (m, 3H), 6.90-6.87 (m, 2H), 4.64 (s, 2H), 4.30-4.27 (dq, 2H, J=7.2 Hz, 2.1 Hz), 2.50 (s, 3H), 1.33-1.28 (tt, 3H, J=7.2 Hz, 1.5 Hz); $^{13}$CNMR (CDCl$_3$) δ 168.6, 157.7, 140.0, 133.0, 131.7, 129.4, 128.1, 125.5, 123.2, 116.9, 114.7, 93.0, 87.4, 65.4, 61.5, 20.7, 14.1; EI-MS m/z 294 (M$^+$).

Example A2

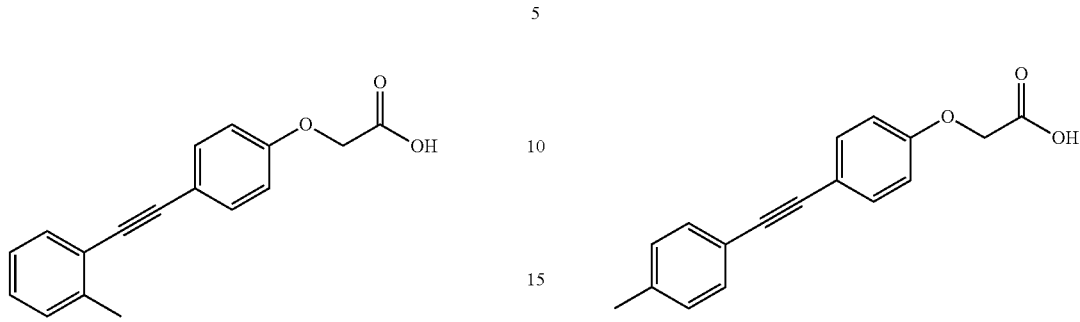

2-(4-(o-Tolylethynyl)phenoxy)acetic acid. The title compound was prepared from ethyl 2-(4-(o-tolylethynyl)phenoxy)acetate (40 mg, 0.14 mmol) according to the general procedure II to give 22 mg (60%) of the pure title compound as an white solid. $R_f$: 0.13 ([EtOAc with 1.25% AcOH]: hexanes, 1:1); $^1$HNMR (DMSO-$d_6$) δ 7.50-7.45 (m, 3H), 7.30-7.28 (m, 2H), 7.24-7.21 (m, 1H), 6.98-6.95 (m, 2H), 4.73 (s, 2H), 2.45 (s, 3H); $^{13}$CNMR (DMSO-$d_6$) δ 169.9, 158.0, 139.4, 132.8, 131.3, 129.6, 128.4, 125.9, 122.4, 114.9, 93.3, 86.9, 64.5, 20.3; MALDI-HRMS calcd for $C_{17}H_{14}O_3$ ($M^+$): 266.0938. found: 266.0939.

Example A3

2-(4-(p-Tolylethynyl)phenoxy)acetic acid. The title compound was prepared from ethyl 2-(4-(p-tolylethynyl)phenoxy)acetate (44 mg, 0.15 mmol) according to the general procedure II to give 25 mg (63%) of the pure title compound as an white solid. $R_f$: 0.14 ([EtOAc with 1.25% AcOH]: hexanes, 1:1); $^1$HNMR (DMSO-$d_6$) δ 7.48-7.40 (m, 4H), 7.23-7.21 (m, 2H), 6.96-6.93 (m, 2H), 4.72 (s, 2H), 2.50 (s, 3H); $^{13}$CNMR (DMSO-$d_6$) δ 169.9, 157.9, 138.2, 132.8, 131.1, 129.3, 119.6, 144.9, 88.7, 88.2, 64.5, 21.0; MALDI-HRMS ($M^+$) calcd for $C_{17}H_{14}O_3$ ($M^+$): 266.0938. found: 266.0936.

Example E3

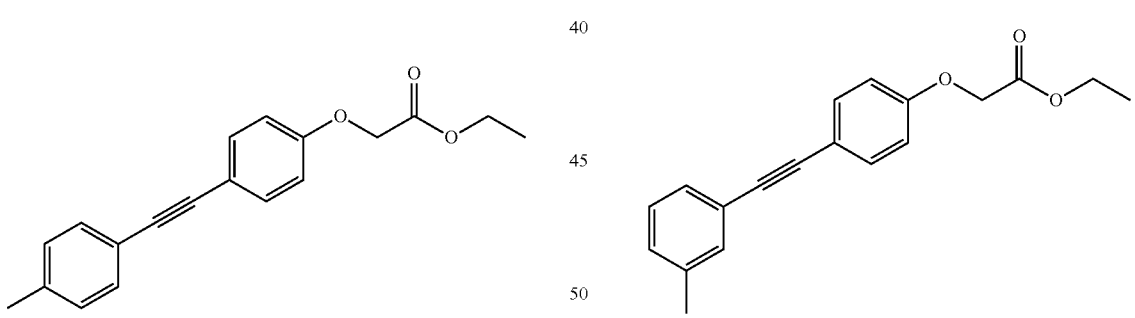

Example E4

Ethyl 2-(4-(p-tolylethynyl)phenoxy)acetate. The title compound was prepared from ethyl (4-ethynylphenoxy)acetate (41 mg, 0.20 mmol) and iodo-4-methylbenzene (46 mg, 0.21 mmol) according to the general procedure ID to give 47 mg (79%) of an orange oil after purification by flash chromatography (SiO$_2$, EtOAc/hexanes, 1:10). $R_f$: 0.14 (EtOAc:hexanes, 1:10); $^1$HNMR (CDCl$_3$) δ 7.49-7.37 (m, 4H), 7.17-7.11 (m, 2H), 6.91-6.84 (m, 2H), 4.63 (s, 2H), 4.29-4.26 (dq, 2H, J=7.2 Hz, 2.1 Hz), 2.36 (s, 3H), 1.32-1.27 (tt, 3H, J=7.2 Hz, 1.5 Hz); $^{13}$CNMR (CDCl$_3$) δ 168.6, 157.6, 138.1, 133.0, 131.4, 129.1, 120.3, 116.8, 114.7, 88.6, 88.3, 65.4, 61.5, 21.5, 14.1; EI-MS m/z 294 ($M^+$).

Ethyl 2-(4-(m-tolylethynyl)phenoxy)acetate. The title compound was prepared from ethyl (4-ethynylphenoxy)acetate (42 mg, 0.21 mmol) and iodo-3-methylbenzene (0.04 mL, 0.31 mmol) according to the general procedure ID to give 56 mg (93%) of an orange oil after purification by flash chromatography (SiO$_2$, EtOAc/hexanes, 1:10). $R_f$: 0.44 (EtOAc:hexanes, 1:5); $^1$HNMR (CDCl$_3$) δ 7.61-7.56 (m, 2H), 7.51-7.31 (m, 4H), 7.03-6.88 (m, 2H), 4.75 (s, 2H), 4.43-4.36 (dq, 2H, J=7.2 Hz, 2.1 Hz), 2.47 (s, 3H), 1.44-1.38 (tt, 3H, J=7.2 Hz, 1.5 Hz); $^{13}$CNMR (CDCl$_3$) δ 168.6, 157.7, 138.0, 133.1, 132.0, 128.9, 128.5, 128.2, 123.2, 116.2, 114.7, 88.6, 88.6, 65.4, 61.5, 21.2, 14.1; EI-MS m/z 294 ($M^+$).

Example A4

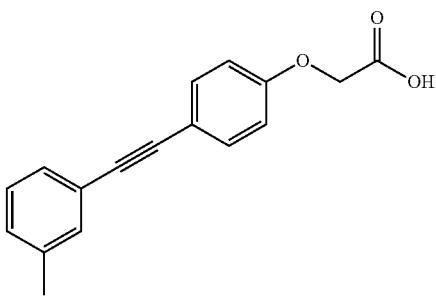 [SMILES: Cc1cccc(C#Cc2ccc(OCC(=O)O)cc2)c1]

2-(4-(m-Tolylethynyl)phenoxy)acetic acid. The title compound was prepared from ethyl 2-(4-(m-tolylethynyl)phenoxy)acetate (40 mg, 0.14 mmol) according to the general procedure II to give 15 mg (41%) of the pure title compound as an white solid. $R_f$: 0.14 ([EtOAc with 1.25% AcOH]:hexanes, 1:1); $^1$HNMR (DMSO-$d_6$) δ 7.49-7.46 (m, 2H), 7.36-7.34 (m, 1H), 7.31-7.29 (m, 2H), 7.21-7.19 (m, 1H), 6.97-6.94 (m, 2H), 4.73 (s, 2H), 2.32 (s, 3H); $^{13}$CNMR (DMSO-$d_6$) δ 158.0, 138.0, 132.8, 131.6, 129.2, 128.6, 122.5, 114.9, 114.8, 89.0, 88.2, 20.7; MALDI-HRMS calcd for $C_{17}H_{14}O_3$ ($M^+$): 266.0938. found: 266.0939.

Intermediate-1

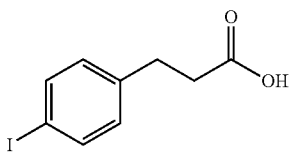 [SMILES: O=C(O)CCc1ccc(I)cc1]

3-(4-Iodophenyl)propanoic acid. A mixture of $H_2SO_4$ (1.25 mL), water (12.5 mL) and AcOH (25 mL) in a 250 mL flask and 3-phenylpropanoic acid (3.00 g, 20.0 mmol), iodine (1.40 g, 5.5 mmol) and $KIO_3$ (0.98 g, 4.6 mmol) was added. The reaction was heated to reflux and a solution of iodine (1.40 g, 5.5 mmol) in AcOH (25 mL) was added in portions of 5 mL as the colour of the reaction faded from purple to orange. After 3 hours when no further colour changes appeared the reaction was cooled to room temperature. before quenching with 1M $NaHSO_3$. The reaction was added water and extracted with EtOAc. The organic phases were combined, washed with brine, dried over $MgSO_4$ and concentrated under vacuum. The product (4.15 g, 75%), containing minor impurites of starting material and the ortho-iodinated product, was recrystallised from PE to provide 1.83 g (33%) of the pure and white crystalline product. $R_f$: 0.10 (EtOAc:hexanes, 1:4); $^1$HNMR (CDCl$_3$) δ 7.62-7.59 (m, 2H), 6.97-6.95 (m, 2H), 2.92-2.87 (t, 2H, J=7.5 Hz), 2.68-2.63 (t, 2H, J=7.5 Hz); $^{13}$CNMR (CDCl$_3$) δ 178.5, 139.7, 137.6, 130.4, 91.6, 35.2, 30.0.

Intermediate-2

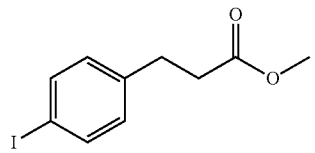

Methyl 3-(4-iodophenyl)propanoate. Methanol (5 mL) under nitrogen at 0° C. was added AcCl (0.4 mL, 5.63 mmol). The reaction was stirred for 10 min before slow addition of 3-(4-iodophenyl)propanoic acid (498 mg, 1.80 mmol). The reaction was stirred for additional 1½ hour at room temperature. before the mixture was concentrated under vacuum, re-dissolved in MeOH and concentrated to give 512 mg (98%) of a pure white solid. $R_f$: 0.39 (EtOAc:hexanes, 1:4); $^1$HNMR (CDCl$_3$) δ 7.61-7.59 (m, 2H), 6.97-6.94 (m, 2H), 3.66 (s, 3H), 2.92-2.87 (t, 2H, J=7.5 Hz), 2.63-2.58 (t, 2H, J=7.5 Hz); $^{13}$CNMR (CDCl$_3$) δ 173.0, 140.1, 137.5, 130.4, 91.4, 51.7, 35.4, 30.4; EI-MS m/z 290.0 ($MH^+$).

Example E5

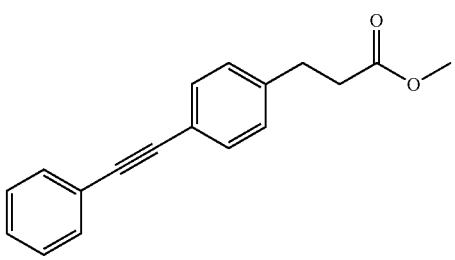 [SMILES: COC(=O)CCc1ccc(C#Cc2ccccc2)cc1]

Methyl 3-(4-(phenylethynyl)phenyl)propanoate. The title compound was prepared from methyl 3-(4-iodophenyl)propanoate (100 mg, 0.34 mmol) and phenylacetylene (0.04 mL, 0.36 mmol) according to the general procedure IA to give 66 mg (72%) of a brown oil after purification by flash chromatography (SiO$_2$, EtOAc/hexanes, 1:10). $R_f$: 0.31 (EtOAc:hexanes, 1:5); $^1$HNMR (CDCl$_3$) δ 7.53-7.50 (m, 2H), 7.47-7.44 (m, 2H), 7.34-7.32 (m, 3H), 7.19-7.16 (m, 2H), 3.66 (s, 3H), 2.98-2.93 (t, 2H, J=7.5 Hz), 2.66-2.61 (t, 2H, J=7.5 Hz); $^{13}$CNMR (CDCl$_3$) δ 173.1, 140.8, 131.7, 131.5, 128.3, 128.3, 128.1, 123.3, 121.2, 89.3, 89.1, 51.6, 35.4, 30.8; ESI-MS m/z 287.1 ($MNa^+$).

Example A5

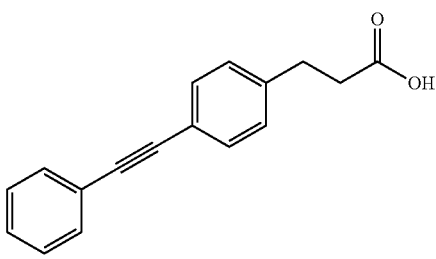 [SMILES: O=C(O)CCc1ccc(C#Cc2ccccc2)cc1]

3-(4-(Phenylethynyl)phenyl)propanoic acid. The title compound was prepared from methyl 3-(4-(phenylethynyl)phenyl)propanoate (52 mg, 0.20 mmol) according to the general procedure II to give 41 mg (78%) of the pure title compound as an yellow solid. $R_f$: 0.35 ([EtOAc with 1.25% AcOH]:hexanes, 1:1); $^1$HNMR (CDCl$_3$) δ 7.54-7.45 (m, 4H), 7.37-7.31 (m, 3H), 7.20-7.18 (m, 2H), 3.00-2.95 (t, 2H, J=7.5 Hz), 2.72-2.66 (t, 2H, J=7.5 Hz); $^{13}$CNMR (CDCl$_3$) δ 178.7, 140.4, 131.8, 131.6, 128.3, 128.3, 128.2, 123.3, 121.3, 89.2, 89.2, 35.2, 30.4; MALDI-HRMS calcd for $C_{17}H_{14}O_2$ ($MNa^+$): 273.0887. found: 273.0883.

Intermediate-3

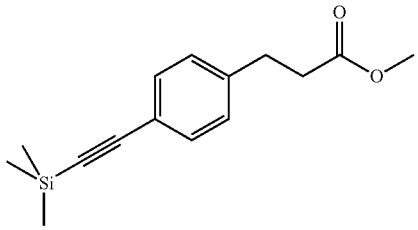

Methyl 3-(4-((trimethylsilyl)ethynyl)phenyl)propanoate. The title compound was prepared from methyl 3-(4-iodophenyl)propanoate (250 mg, 0.86 mmol) and trimethylsilylacetylene (0.22 mL, 1.70 mmol) according to the general procedure IA. After filtration through Celite, the product was obtained as a brown oil and used without purification in the next step. $R_f$: 0.38 (EtOAc:hexanes, 1:5); $^1$HNMR (CDCl$_3$) δ 7.39-7.37 (m, 2H), 7.13-7.11 (m, 2H), 3.65 (s, 3H), 2.96-2.91 (t, 2H, J=7.6 Hz), 2.63-2.58 (t, 2H, J=7.8 Hz), 0.24 (s, 9H); $^{13}$CNMR (CDCl$_3$) δ 173.1, 141.1, 132.1, 128.2, 121.1, 105.0, 93.8, 51.6, 35.6, 30.8, 0.0.

Intermediate-4

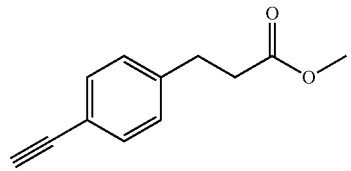

Methyl 3-(4-ethynylphenyl)propanoate. Methyl 3-(4-((trimethylsilyl)ethynyl)phenyl)propanoate (225 mg, 0.86 mmol) and potassium carbonate (234 mg, 1.69 mmol) was dissolved in MeOH (9 mL) and stirred vigorously for 2½ hours at room temperature. The reaction was added water and extracted with EtOAc. The organic phases were combined, washed with brine, dried over MgSO$_4$ before concentrated under vacuum to give 138 mg (90%) of a brown, oily product. $R_f$: 0.31 (EtOAc:hexanes, 1:5); $^1$HNMR (CDCl$_3$) δ 7.43-7.40 (m, 2H), 7.17-7.14 (m, 2H), 3.66 (s, 3H), 3.04 (s, 1H), 2.97-2.92 (t, 2H, J=7.7 Hz), 2.65-2.59 (t, 2H, J=7.8 Hz); $^{13}$CNMR (CDCl$_3$) δ 173.0, 141.4, 132.3, 128.3, 120.2, 83.5, 76.8, 51.6, 35.3, 30.8; ESI-MS m/z 287.1 (MNa$^+$).

Example E6

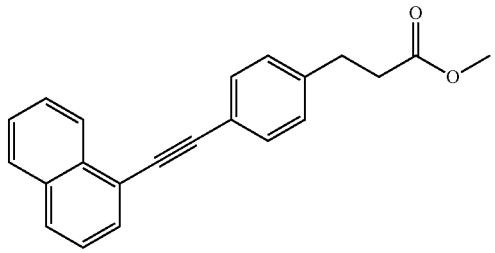 [SMILES: COC(=O)CCc1ccc(C#Cc2cccc3ccccc23)cc1]

Methyl 3-(4-(1-naphthylethynyl)phenyl)propanoate. The title compound was prepared from methyl 3-(4-((2-chloropyridin-4-yl)ethynyl)phenyl)propanoate (80 mg, 0.27 mmol) and 1-bromonaphthalene (53 μL, 0.38 mmol) according to the general procedure IB to give 26 mg (24%) of an orange oil after purification by flash chromatography (SiO$_2$, EtOAc/hexanes, 1:30→1:10). $R_f$: 0.25 (EtOAc:hexanes, 1:5); $^1$HNMR (CDCl$_3$) δ 8.44-8.41 (m, 1H), 7.87-7.73 (m, 3H), 7.58-7.44 (m, 5H), 7.24-7.21 (m, 2H), 3.00-2.96 (t, 2H, J=7.5 Hz), 2.68-2.63 (t, 2H, J=7.5 Hz); $^{13}$CNMR (CDCl$_3$) δ 173.1, 141.0, 133.2, 133.2, 131.8, 130.3, 128.7, 128.4, 128.3, 126.7, 126.4, 126.2, 125.3, 121.3, 121.0, 94.2, 87.2, 51.6, 35.4, 30.8; MALDI-MS m/z 314.1 (M$^+$).

Example A6

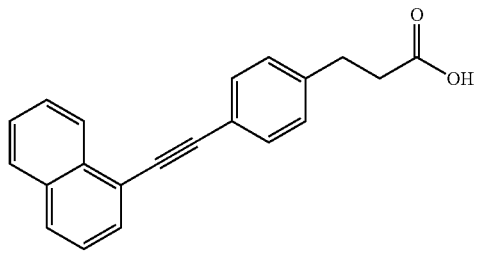 [SMILES: O=C(O)CCc1ccc(C#Cc2cccc3ccccc23)cc1]

3-(4-(1-Naphthylethynyl)phenyl)propanoic acid. The title compound was prepared from methyl 3-(4-(1-naphthylethynyl)phenyl)propanoate (24 mg, 0.08 mmol) according to the general procedure II to give 18 mg (80%) of the pure title compound as a pale yellow solid. $R_f$: 0.32 ([EtOAc with 1.25% AcOH]:hexanes, 1:1); $^1$HNMR ((CD$_3$)$_2$CO-d$_6$) δ 10.60-10.30 (s, 1H), 8.44-8.41 (m, 1H), 7.95-7.91 (m, 2H), 7.77-7.74 (m, 1H), 7.65-7.50 (m, 5H), 7.35-7.33 (m, 2H), 2.97-2.92 (t, 2H, J=7.5 Hz), 2.67-2.61 (t, 2H, J=7.5 Hz); $^{13}$CNMR ((CD$_3$)$_2$CO-d$_6$) δ 173.6, 142.9, 134.1, 133.8, 132.3, 131.0, 129.6, 129.5, 129.2, 127.7, 127.3, 126.6, 126.2, 121.6, 121.5, 95.1, 87.5, 35.4, 31.2; MALDI-HRMS calcd for C$_{21}$H$_{16}$O$_2$ (M$^+$): 300.1145. found: 300.1137.

Example E7

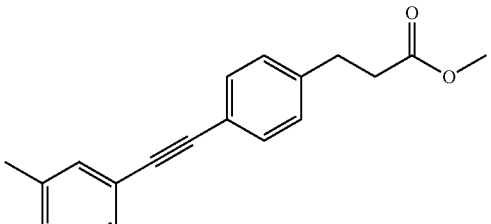

Methyl 3-(4-(m-tolylethynyl)phenyl)propanoate. The title compound was prepared from methyl 3-(4-ethynylphenyl)propanoate (90 mg, 0.48 mmol) and iodo-3-methylbenzene (0.07 mL, 0.55 mmol) according to the general procedure IB to give 42 mg (36%) of an orange oil after purification by flash chromatography (SiO$_2$, EtOAc/hexanes, 1:30→1:10). $R_f$: 0.29 (EtOAc:hexanes, 1:5); $^1$HNMR (CDCl$_3$) δ 7.46-7.43 (m, 2H), 7.35-7.31 (m, 2H), 7.22-7.12 (m, 4H), 3.67 (s, 3H), 2.99-2.93 (t, 2H, J=7.8 Hz), 2.66-2.61 (t, 2H, J=7.8 Hz), 2.35 (s, 3H); $^{13}$CNMR (CDCl$_3$) δ 173.1, 140.8, 138.0, 132.1, 131.7, 129.1, 128.6, 128.3, 128.2, 123.1, 121.3, 89.3, 88.9, 51.6, 35.4, 30.8, 21.2; ESI-MS m/z 301.1 (MNa$^+$).

Example A7

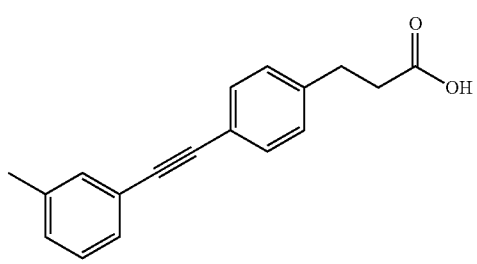 [SMILES: Cc1cccc(C#Cc2ccc(CCC(=O)O)cc2)c1]

3-(4-(m-Tolylethynyl)phenyl)propanoic acid. The title compound was prepared from methyl 3-(4-(m-tolylethynyl)phenyl)propanoate (39 mg, 0.14 mmol) according to the general procedure II to give 35 mg (95%) of the pure title compound as a yellow solid. $R_f$: 0.11 ([EtOAc with 1.25% AcOH]:hexanes, 1:4); $^1$HNMR (CDCl$_3$) δ 7.47-7.44 (m, 2H), 7.35-7.31 (m, 2H), 7.25-7.14 (m, 4H), 2.99-2.94 (t, 2H, J=7.8 Hz), 2.71-2.66 (t, 2H, J=7.8 Hz), 2.34 (s, 3H); $^{13}$CNMR (CDCl$_3$) δ 178.6, 140.4, 138.0, 132.1, 131.8, 129.1, 128.6, 128.3, 128.2, 123.1, 121.4, 89.4, 88.9, 35.2, 30.5, 21.2; MALDI-HRMS calcd for C$_{18}$H$_{16}$O$_2$ (M$^+$): 264.1145. found: 264.1145.

Example E8

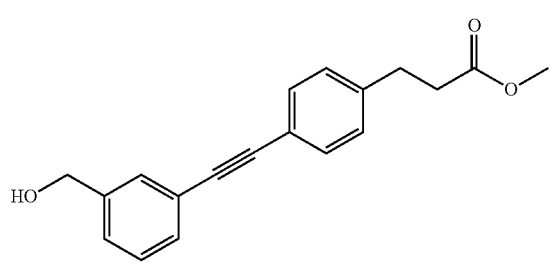 [SMILES: COC(=O)CCc1ccc(C#Cc2cccc(CO)c2)cc1]

Methyl 3-(4-((3-(hydroxymethyl)phenyl)ethynyl)phenyl)propanoate. The title compound was prepared from methyl 3-(4-ethynylphenyl)propanoate (90 mg, 0.48 mmol) and (3-iodophenyl)methanol (0.07 mL, 0.55 mmol) according to the general procedure IB to give 40 mg (32%) of an orange oil after purification by flash chromatography (SiO$_2$, EtOAc/hexanes, 1:30→1:10). $R_f$: 0.24 (EtOAc:hexanes, 1:5); $^1$HNMR (CDCl$_3$) δ 7.53 (s, 1H), 7.46-7.43 (m, 3H), 7.34-7.32 (m, 2H), 7.19-7.16 (m, 2H), 4.69 (s, 2H), 3.66 (s, 3H), 2.98-2.93 (t, 2H, J=7.8 Hz), 2.66-2.61 (t, 2H, J=7.8 Hz), 1.83 (s, 1H); $^{13}$CNMR (CDCl$_3$) δ 173.1, 141.1, 140.9, 131.7, 130.7, 130.0, 128.6, 128.3, 126.7, 123.6, 121.1, 89.4, 88.9, 64.9, 51.6, 35.4, 30.8; ESI-MS m/z 317.1 (MNa$^+$).

Example A8

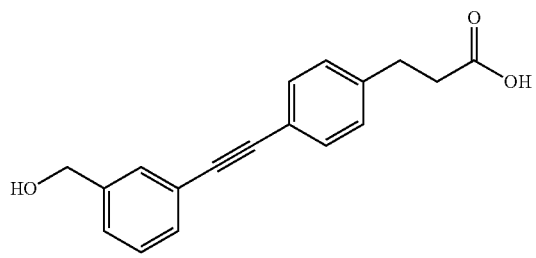 [SMILES: O=C(O)CCc1ccc(C#Cc2cccc(CO)c2)cc1]

3-(4-((3-(Hydroxymethyl)phenyl)ethynyl)phenyl)propanoic acid. The title compound was prepared from methyl 3-(4-((3-(hydroxymethyl)phenyl)ethynyl)phenyl)propanoate (38 mg, 0.13 mmol) according to the general procedure II to give 34 mg (93%) of the pure title compound as a yellow solid. $R_f$: 0.29 ([EtOAc with 1.25% AcOH]:hexanes, 1:1); $^1$HNMR ((CD$_3$)$_2$CO-d$_6$) δ 13.15-10.20 (s, 1H), 7.53-7.30 (m, 8H), 4.65 (s, 2H), 2.97-2.92 (t, 2H, J=7.8 Hz), 2.66-2.61 (t, 2H, J=7.8 Hz); $^{13}$CNMR ((CD$_3$)$_2$CO-d$_6$) δ 132.3, 130.6, 130.3, 130.2, 129.5, 129.5, 129.3, 127.4, 89.8, 64.1, 35.5, 31.4; MALDI-HRMS calcd for C$_{18}$H$_{16}$O$_3$ (MNa$^+$): 303.0992. found: 303.0986.

Example E9

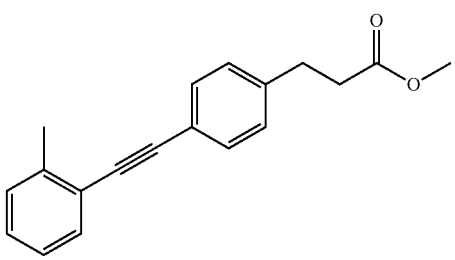 [SMILES: COC(=O)CCc1ccc(C#Cc2ccccc2C)cc1]

Methyl 3-(4-(o-tolylethynyl)phenyl)propanoate. The title compound was prepared from methyl 3-(4-ethynylphenyl)propanoate (90 mg, 0.48 mmol) and iodo-2-methylbenzene (0.07 mL, 0.55 mmol) according to the general procedure IB to give 36 mg (31%) of an orange oil after purification by flash chromatography (SiO$_2$, EtOAc/hexanes, 1:30→1:10). $R_f$: 0.27 (EtOAc:hexanes, 1:5); $^1$HNMR (CDCl$_3$) δ 7.49-7.44 (m, 3H), 7.23-7.17 (m, 5H), 3.67 (s, 3H), 2.99-2.94 (t, 2H, J=7.8 Hz), 2.66-2.61 (t, 2H, J=7.8 Hz), 2.50 (s, 3H); $^{13}$CNMR (CDCl$_3$) δ 173.1, 140.8, 140.1, 131.8, 131.6, 129.4, 128.3, 128.2, 125.5, 123.1, 121.5, 93.2, 88.1, 51.6, 35.4, 30.8, 20.7; ESI-MS m/z 301.1 (MNa$^+$).

Example A9

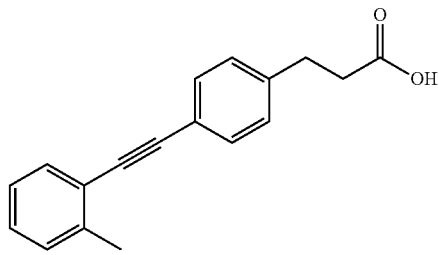 [SMILES: Cc1ccccc1C#Cc1ccc(CCC(=O)O)cc1]

3-(4-(o-Tolylethynyl)phenyl)propanoic acid. The title compound was prepared from methyl 3-(4-(o-tolylethynyl)phenyl)propanoate (31 mg, 0.11 mmol) according to the general procedure II to give 28 mg (96%) of the pure title compound as a yellow solid. $R_f$: 0.08 ([EtOAc with 1.25% AcOH]:hexanes, 1:4); $^1$HNMR (CDCl$_3$) δ 11.75-10.30 (s, 1H), 7.49-7.45 (m, 3H), 7.24-7.18 (m, 5H), 2.99-2.94 (t, 2H, J=7.8 Hz), 2.71-2.66 (t, 2H, J=7.8 Hz), 2.50 (s, 3H); $^{13}$CNMR (CDCl$_3$) δ 178.9, 140.4, 140.1, 131.8, 131.7, 129.4, 128.3, 128.2, 125.6, 123.0, 121.6, 93.2, 88.1, 35.3, 30.4, 20.7; MALDI-HRMS calcd for C$_{18}$H$_{16}$O$_2$ (MNa$^+$): 287.1043. found: 287.1047.

Example A10

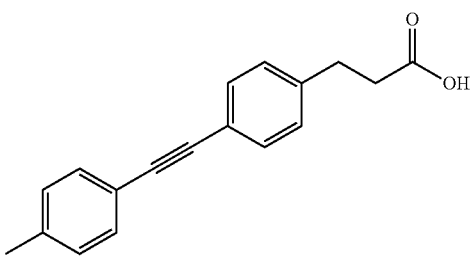

3-(4-(m-Tolylethynyl)phenyl)propanoic acid. The title compound was prepared from methyl 3-(4-(m-tolylethynyl)phenyl)propanoate (16 mg, 0.06 mmol) according to the general procedure II to give 12 mg (80%) of the pure title compound as a yellow solid. $R_f$: 0.35 ([EtOAc with 1.25% AcOH]:hexanes, 1:1); $^1$HNMR (CDCl$_3$) δ 12.10-10.10 (s, 1H), 7.46-7.40 (m, 4H), 7.20-7.13 (m, 4H), 2.99-2.94 (t, 2H, J=7.8 Hz), 2.71-2.66 (t, 2H, J=7.8 Hz), 2.36 (s, 3H); $^{13}$CNMR (CDCl$_3$) δ 178.3, 140.4, 138.5, 131.9, 131.6, 129.3, 128.5, 121.7, 120.4, 89.5, 88.7, 35.3, 30.6, 21.7; MALDI-HRMS calcd for C$_{18}$H$_{16}$O$_2$ (M$^+$): 264.1145. found: 264.1141.

Example E10

Example E11

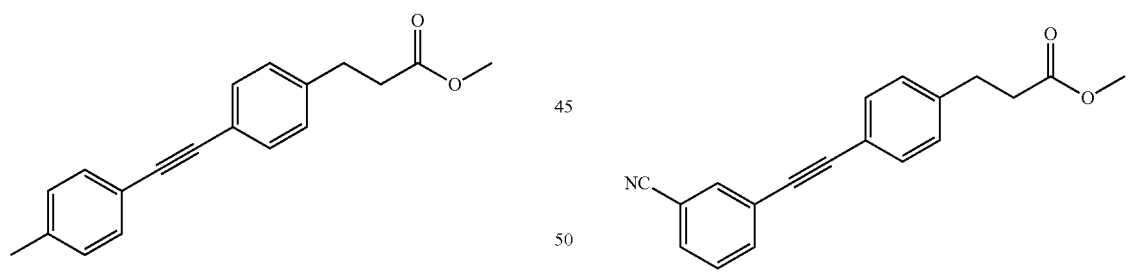

Methyl 3-(4-(p-tolylethynyl)phenyl)propanoate. The title compound was prepared from methyl 3-(4-ethynylphenyl)propanoate (90 mg, 0.48 mmol) and iodo-4-methylbenzene (0.07 mL, 0.55 mmol) according to the general procedure IB to give 18 mg (15%) of an orange oil after purification by flash chromatography (SiO$_2$, EtOAc/hexanes, 1:30→1:10). $R_f$: 0.42 (EtOAc:hexanes, 1:5); $^1$HNMR (CDCl$_3$) δ 7.45-7.39 (m, 4H), 7.18-7.13 (m, 4H), 3.67 (s, 3H), 2.98-2.93 (t, 2H, J=7.8 Hz), 2.66-2.60 (t, 2H, J=7.8 Hz), 2.36 (s, 3H); $^{13}$CNMR (CDCl$_3$) δ 173.1, 140.6, 138.3, 131.7, 131.4, 129.1, 128.3, 121.4, 120.2, 89.3, 88.6, 51.6, 35.4, 30.8, 21.5; EI-MS m/z 278 (M$^+$).

Methyl 3-(4-((3-cyanophenyl)ethynyl)phenyl)propanoate. The title compound was prepared from methyl 3-(4-ethynylphenyl)propanoate (103 mg, 0.55 mmol) and 3-iodobenzonitrile (134 mg, 0.59 mmol) according to the general procedure IC to give 68 mg (58%) of an orange-brown solid after purification by flash chromatography (SiO$_2$, EtOAc/hexanes, 1:5). $R_f$: 0.26 (EtOAc:hexanes, 1:5); $^1$HNMR (CDCl$_3$) δ 7.79-7.78 (m, 1H), 7.73-7.70 (m, 1H), 7.61-7.57 (m, 1H), 7.48-7.43 (m, 3H), 7.22-7.18 (m, 2H), 3.67 (s, 3H), 3.00-2.95 (t, 2H, J=7.8 Hz), 2.67-2.62 (t, 2H, J=7.8 Hz); $^{13}$CNMR (CDCl$_3$) δ 173.0, 141.7, 135.5, 134.8, 131.9, 131.3, 129.2, 128.5, 125.0, 120.2, 118.1, 116.7, 112.8, 91.7, 86.6, 51.7, 35.3, 30.8; EI-MS m/z 289 (M$^+$).

Example A11

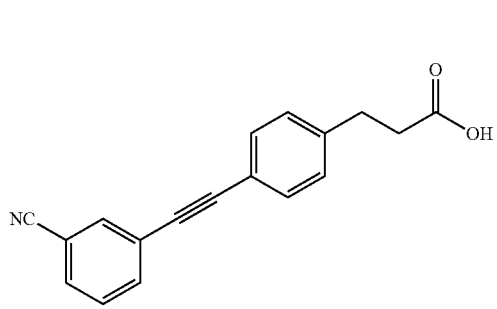 [SMILES: N#Cc1cccc(C#Cc2ccc(CCC(=O)O)cc2)c1]

3-(4-((3-Cyanophenyl)ethynyl)phenyl)propanoic acid. The title compound was prepared from methyl 3-(4-((3-cyanophenyl)ethynyl)phenyl)propanoate (58 mg, 0.20 mmol) according to the general procedure II to give 53 mg (96%) of the pure title compound as a light brown solid. $R_f$: 0.35 ([EtOAc with 1.25% AcOH]:hexanes, 1:1); $^1$HNMR (DMSO-$d_6$) δ 12.30-12.10 (s, 1H), 8.07-8.03 (m, 1H), 7.91-7.85 (m, 2H), 7.70-7.60 (m, 1H), 7.53-7.48 (m, 2H), 7.33-7.29 (m, 2H), 2.89-2.84 (t, 2H, J=7.8 Hz), 2.59-2.54 (t, 2H, J=7.8 Hz); $^{13}$CNMR (DMSO-$d_6$) δ 173.5, 142.5, 135.8, 134.5, 132.0, 131.4, 131.3, 130.0, 128.7, 128.7, 123.7, 119.1, 112.1, 91.3, 86.8, 34.7, 30.1; ESI-MS calcd for $C_{18}H_{13}NO_2$ (MNa$^+$): 298.0839. found: 298.0852.

Example A12

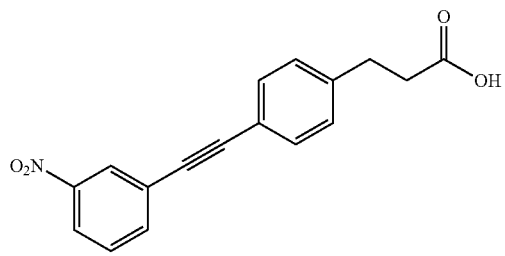

3-(4-((3-Nitrophenyl)ethynyl)phenyl)propanoic acid. The title compound was prepared from methyl 3-(4-((3-nitrophenyl)ethynyl)phenyl)propanoate (84 mg, 0.27 mmol) according to the general procedure II to give 74 mg (92%) of the pure title compound as a pale yellow solid. $R_f$: 0.15 (EtOAc:hexanes, 1:1); $^1$HNMR (DMSO-$d_6$) δ 12.17 (s, 1H), 8.32-8.31 (m, 1H), 8.26-8.22 (m, 1H), 8.00-7.96 (m, 1H), 7.75-7.69 (m, 1H), 7.55-7.52 (m, 2H), 7.34-7.31 (m, 2H), 3.00-2.85 (t, 2H, J=7.8 Hz), 2.60-2.55 (t, 2H, J=7.8 Hz); $^{13}$CNMR (DMSO-$d_6$) δ 173.5, 147.8, 142.6, 137.4, 131.5, 130.3, 128.7, 125.7, 123.9, 123.3, 119.0, 91.5, 86.6, 34.7, 30.2; MALDI-HRMS calcd for $C_{17}H_{13}NO_4$ (MNa$^+$): 318.0737. found: 318.0731.

Example E12

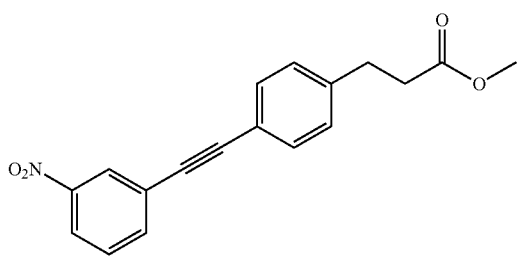 [SMILES: COC(=O)CCc1ccc(C#Cc2cccc([N+](=O)[O-])c2)cc1]

Methyl 3-(4-((3-nitrophenyl)ethynyl)phenyl)propanoate. The title compound was prepared from methyl 3-(4-ethynylphenyl)propanoate (102 mg, 0.54 mmol) and 1-iodo-3-nitrobenzene (146 mg, 0.58 mmol) according to the general procedure IC to give 113 mg (67%) of a pale orange solid after purification by flash chromatography (SiO$_2$, EtOAc/hexanes, 1:5). $R_f$: 0.30 (EtOAc:hexanes, 1:5); $^1$HNMR (CDCl$_3$) δ 8.36-8.35 (m, 1H), 8.18-8.14 (m, 1H), 7.82-7.79 (m, 1H), 7.55-7.46 (m, 3H), 7.23-7.20 (m, 2H), 3.68 (s, 3H), 3.01-2.96 (t, 2H, J=7.8 Hz), 2.68-2.62 (t, 2H, J=7.8 Hz); $^{13}$CNMR (CDCl$_3$): δ 173.0, 148.2, 141.8, 137.1, 131.9, 129.3, 128.5, 126.3, 125.2, 122.8, 120.1, 91.9, 86.6, 51.7, 35.3, 30.8; EI-MS m/z 309 (M$^+$).

Example E13

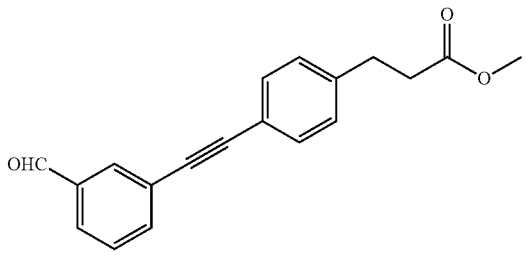 [SMILES: COC(=O)CCc1ccc(C#Cc2cccc(C=O)c2)cc1]

Methyl 3-(4-((3-formylphenyl)ethynyl)phenyl)propanoate. The title compound was prepared from methyl 3-(4-ethynylphenyl)propanoate (102 mg, 0.54 mmol) and 3-bromobenzaldehyde (0.09 mL, 0.62 mmol) according to the general procedure IC to give 93 mg (59%) of an orange solid after purification by flash chromatography (SiO$_2$, EtOAc/hexanes, 1:3). $R_f$: 0.16 (EtOAc:hexanes, 1:5); $^1$HNMR (CDCl$_3$) δ 10.01 (s, 1H), 8.02 (s, 1H), 7.84-7.74 (m, 2H), 7.54-7.46 (m, 3H), 7.26-7.19 (m, 2H), 3.67 (s, 3H), 3.00-2.95 (t, 2H, J=7.8 Hz), 2.67-2.62 (t, 2H, J=7.8 Hz); $^{13}$CNMR (CDCl$_3$) δ 191.6, 173.0, 141.4, 137.0, 136.5, 132.9, 131.8, 129.1, 128.8, 128.4, 124.6, 120.6, 90.9, 87.6, 51.6, 35.3, 30.8; EI-MS m/z 292 (M$^+$).

Example A13

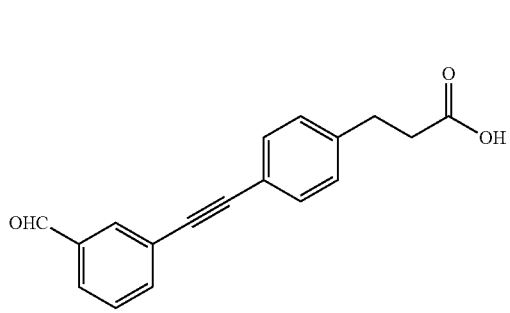 [SMILES: O=Cc1cccc(C#Cc2ccc(CCC(=O)O)cc2)c1]

3-(4-((3-Formylphenyl)ethynyl)phenyl)propanoic acid. The title compound was prepared from methyl 3-(4-((3-formylphenyl)ethynyl)phenyl)propanoate (70 mg, 0.24 mmol) according to the general procedure II to give 57 mg (85%) of the pure title compound as a pale yellow solid. $R_f$: 0.13 (EtOAc:hexanes, 1:1); $^1$HNMR (DMSO-$d_6$) δ 12.28 (s, 1H), 10.04 (s, 1H), 8.06-8.04 (m, 1H), 7.97-7.91 (m, 1H), 7.88-7.84 (m, 1H), 7.68-7.63 (m, 1H), 7.56-7.48 (m, 2H), 7.39-7.28 (m, 2H), 2.90-2.85 (t, 2H, J=7.8 Hz), 2.60-2.55 (t, 2H, J=7.8 Hz); $^{13}$CNMR (DMSO-$d_6$) δ 192.6, 173.5, 142.2, 136.7, 136.4, 132.4, 131.4, 129.6, 128.8, 128.7, 123.3, 119.3, 90.6, 87.5, 34.7, 30.1; MALDI-HRMS calcd for $C_{18}H_{14}O_3$ (MNa$^+$): 301.0836. found: 301.0842.

Example A14

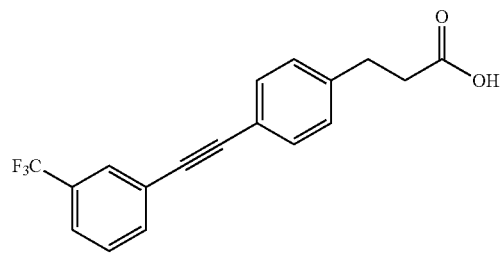

3-(4-((3-(Trifluoromethyl)phenyl)ethynyl)phenyl)propanoic acid. The title compound was prepared from methyl 3-(4-((3-(trifluoromethyl)phenyl)ethynyl)phenyl)propanoate (101 mg, 0.30 mmol) according to the general procedure II to give 84 mg (87%) of the pure title compound as a pale yellow solid. $R_f$: 0.24 ([EtOAc with 1.25% AcOH]:hexanes, 1:1); $^1$HNMR (CDCl$_3$) δ 10.80-9.40 (s, 1H), 7.78 (m, 1H), 7.69-7.66 (m, 1H), 7.58-7.55 (m, 1H), 7.49-7.46 (m, 3H), 7.22-7.20 (m, 2H), 3.01-2.96 (t, 2H, J=7.8 Hz), 2.72-2.67 (t, 2H, J=7.8 Hz); $^{13}$CNMR (CDCl$_3$) δ 178.7, 141.0, 134.6, 131.9, 128.8, 128.4, 128.4, 128.3, 124.7, 124.7, 124.3, 120.7, 90.8, 87.6, 35.2, 30.4; MALDI-HRMS calcd for $C_{18}H_{13}F_3O_2$ (MNa$^+$): 341.0761. found: 341.0754.

Example E14

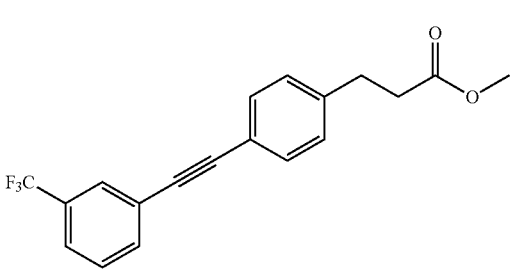 [SMILES: COC(=O)CCc1ccc(C#Cc2cccc(C(F)(F)F)c2)cc1]

Methyl 3-(4-((3-(trifluoromethyl)phenyl)ethynyl)phenyl)propanoate. The title compound was prepared from methyl 3-(4-ethynylphenyl)propanoate (101 mg, 0.54 mmol) and 1-iodo-3-(trifluoromethyl)benzene (0.09 mL, 0.62 mmol) according to the general procedure IC to give 119 mg (67%) of an yellow oil after purification by flash chromatography (SiO$_2$, EtOAc/hexanes, 1:5). $R_f$: 0.58 (EtOAc:hexanes, 2:5); $^1$HNMR (CDCl$_3$) δ 7.77 (s, 1H), 7.68-7.66 (m, 1H), 7.57-7.55 (m, 1H), 7.48-7.43 (m, 3H), 7.21-7.18 (m, 2H), 3.67 (s, 3H), 3.00-2.94 (t, 2H, J=7.8 Hz), 2.67-2.61 (t, 2H, J=7.8 Hz); $^{13}$CNMR (CDCl$_3$) δ 173.0, 141.4, 134.6, 131.8, 128.8, 128.4, 128.3, 128.3, 124.7, 124.6, 124.6, 124.3, 120.5, 90.8, 87.5, 51.6, 35.3, 30.8; ESI-MS m/z 355.1 (MNa$^+$).

Example E15

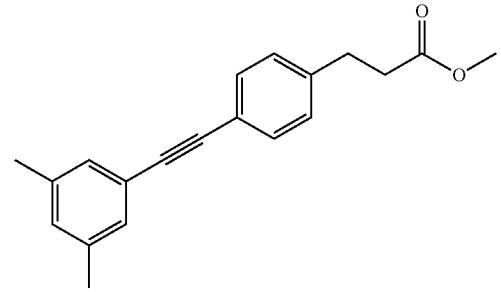

Methyl 3-(4-((3,5-dimethylphenyl)ethynyl)phenyl)propanoate. The title compound was prepared from methyl 3-(4-ethynylphenyl)propanoate (99 mg, 0.53 mmol) and 1-iodo-3,5-dimethylbenzene (0.08 mL, 0.55 mmol) according to the general procedure IC to give 128 mg (83%) of an orange solid after purification by flash chromatography (SiO$_2$, EtOAc/hexanes, 1:5). $R_f$: 0.59 (EtOAc:hexanes, 2:5); $^1$HNMR (CDCl$_3$) δ 7.21-7.19 (m, 2H), 7.07-7.05 (m, 2H), 6.90-6.89 (m, 2H), 6.78-6.77 (m, 1H), 2.72-2.67 (t, 2H, J=7.8 Hz), 2.42-2.37 (t, 2H, J=7.8 Hz), 2.05 (s, 6H); $^{13}$CNMR (CDCl$_3$) δ 173.1, 140.7, 137.8, 131.7, 130.1, 129.2, 128.3, 122.9, 121.4, 89.4, 88.6, 51.6, 35.4, 30.8, 21.1; ESI-MS m/z 315.1 (MNa$^+$).

Example A15

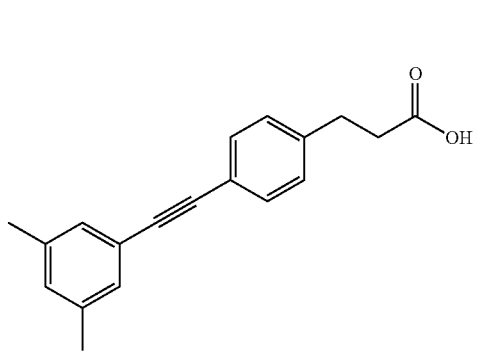 [SMILES: Cc1cc(C)cc(C#Cc2ccc(CCC(=O)O)cc2)c1]

3-(4-((3,5-Dimethylphenyl)ethynyl)phenyl)propanoic acid. The title compound was prepared from methyl 3-(4-((3,5-dimethylphenyl)ethynyl)phenyl)propanoate (100 mg, 0.34 mmol) according to the general procedure II to give 67 mg (70%) of the pure title compound as an yellow solid. $R_f$: 0.24 ([EtOAc with 1.25% AcOH]:hexanes, 1:1); $^1$HNMR ((CD$_3$)$_2$CO-d$_6$) δ 12.00-9.50 (s, 1H), 7.25-7.18 (m, 2H), 7.10-7.04 (m, 2H), 6.94-6.88 (m, 2H), 6.82-6.76 (m, 1H), 2.72-2.67 (t, 2H, J=7.8 Hz), 2.42-2.37 (t, 2H, J=7.8 Hz); $^{13}$CNMR ((CD$_3$)$_2$CO-d$_6$) δ 173.7, 142.7, 138.9, 132.3, 131.0, 129.9, 129.5, 123.9, 121.9, 90.0, 89.4, 35.5, 31.4, 21.1; MALDI-HRMS calcd for C$_{16}$H$_{18}$O$_2$(MNa$^+$): 301.1200. found: 301.1196.

Example A16

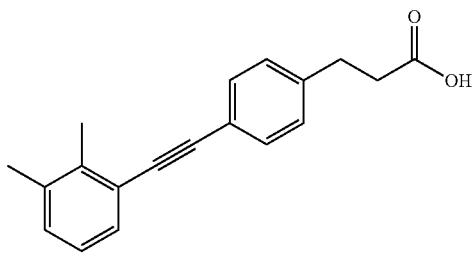

3-(4-((2,3-Dimethylphenyl)ethynyl)phenyl)propanoic acid. The title compound was prepared from methyl 3-(4-((2,3-dimethylphenyl)ethynyl)phenyl)propanoate (22 mg, 0.07 mmol) according to the general procedure II to give 14 mg (67%) of the pure title compound as an orange solid. $R_f$: 0.24 ([EtOAc with 1.25% AcOH]:hexanes, 1:1); $^1$HNMR (CDCl$_3$) δ 11.00-9.90 (s, 1H), 7.38-7.36 (m, 2H), 7.33-7.17 (m, 3H), 7.04-6.96 (m, 2H), 2.84-2.79 (t, 2H, J=7.8 Hz), 2.54-2.49 (t, 2H, J=7.8 Hz); $^{13}$CNMR (CDCl$_3$) δ 173.8, 142.7, 137.8, 132.2, 130.8, 130.5, 129.6, 126.4, 124.0, 122.1, 93.5, 89.2, 35.6, 31.4, 20.3, 17.6; MALDI-HRMS calcd for C$_{19}$H$_{18}$O$_2$ (MNa$^+$): 301.1200. found: 301.1193.

Example E16

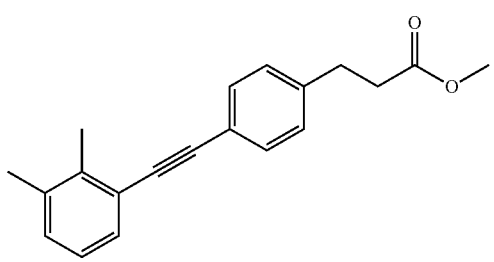

Methyl 3-(4-((2,3-dimethylphenyl)ethynyl)phenyl)propanoate. The title compound was prepared from methyl 3-(4-ethynylphenyl)propanoate (99 mg, 0.53 mmol) and 1-bromo-2,3-dimethylbenzene (0.08 mL, 0.59 mmol) according to the general procedure IC to give 22 mg (14%) of an orange oil after purification by flash chromatography (SiO$_2$, EtOAc/hexanes, 1:5). $R_f$: 0.42 (EtOAc:hexanes, 2:5); $^1$HNMR (CDCl$_3$) δ 7.47-7.44 (m, 2H), 7.37-7.34 (m, 1H), 7.19-7.17 (m, 2H), 7.12-7.03 (m, 2H), 3.67 (s, 3H), 2.99-2.94 (t, 2H, J=7.8 Hz), 2.66-2.61 (t, 2H, J=7.8 Hz), 2.45 (s, 3H), 2.29 (s, 3H); $^{13}$CNMR (CDCl$_3$) δ 173.7, 142.7, 137.8, 132.2, 130.8, 130.5, 129.6, 126.4, 124.0, 122.1, 93.5, 89.2, 35.6, 31.4, 20.3, 17.6; ESI-MS m/z 315.1 (MNa$^+$).

Example E17

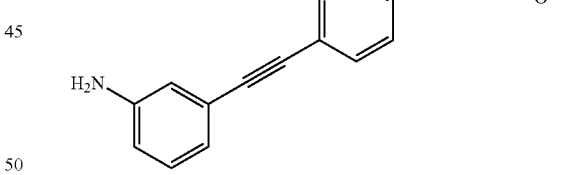

Methyl 3-(4-((3-aminophenyl)ethynyl)phenyl)propanoate. The title compound was prepared from methyl 3-(4-iodophenyl)propanoate (100 mg, 0.34 mmol) and 3-ethynylaniline (0.04 mL, 0.38 mmol) according to the general procedure IC to give 89 mg (93%) of an orange solid after purification by flash chromatography (SiO$_2$, EtOAc/hexanes, 1:3). $R_f$: 0.35 (EtOAc:hexanes, 1:1); $^1$HNMR (CDCl$_3$) δ 7.44-7.42 (m, 2H), 7.18-7.09 (m, 3H), 6.93-6.91 (m, 1H), 6.83 (s, 1H), 6.66-6.63 (m, 1H), 3.66 (s, 3H), 2.98-2.93 (t, 2H, J=7.8 Hz), 2.65-2.60 (t, 2H, J=7.8 Hz); $^{13}$CNMR (CDCl$_3$) δ 173.1, 146.3, 140.7, 131.7, 129.2, 128.3, 124.0, 122.0, 121.3, 117.7, 115.2, 89.3, 88.6, 51.6, 35.4, 30.8; EI-MS m/z 279 (M$^+$).

Example A17

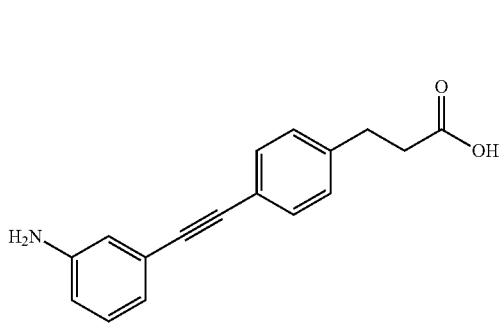

3-(4-((3-Aminophenyl)ethynyl)phenyl)propanoic acid. The title compound was prepared from methyl 3-(4-((3-aminophenyl)ethynyl)phenyl)propanoate (19 mg, 0.07 mmol) according to the general procedure II to give 13 mg (73%) of the pure title compound as a brown solid. $R_f$: 0.09 ([EtOAc with 1.25% AcOH]:hexanes, 1:2); $^1$HNMR (CDCl$_3$) δ 13.10-11.20 (s, 1H), 7.50-7.42 (m, 2H), 7.38-7.28 (m, 3H), 7.24-7.05 (m, 1H), 6.87-6.68 (m, 2H), 2.97-2.92 (m, 2H), 2.66-2.62 (m, 2H); ESI-HRMS calcd for $C_{17}H_{15}NO_2$ (MH$^+$): 266.1176. found: 266.1163.

Example E18

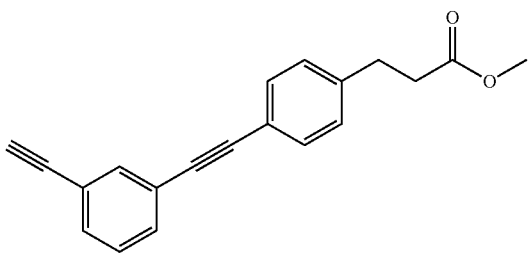 [SMILES: C#Cc1cccc(C#Cc2ccc(CCC(=O)OC)cc2)c1]

Methyl 3-(4-((3-ethynylphenyl)ethynyl)phenyl)propanoate. The title compound was prepared from methyl 3-(4-iodophenyl)propanoate (120 mg, 0.41 mmol) and 1,3-diethynylbenzene (0.06 mL, 0.45 mmol) according to the general procedure IC, with the exception that the reaction was performed at room temperature, to give 52 mg (43%) of an yellow-brown gummy oil after purification by flash chromatography (SiO$_2$, EtOAc/hexanes, 1:3). $R_f$: 0.41 (EtOAc:hexanes, 1:2); $^1$HNMR (CDCl$_3$) δ 7.65 (s, 1H), 7.49-7.42 (m, 4H), 6.31-7.29 (m, 1H), 7.19-7.17 (m, 2H), 3.67 (s, 3H), 3.09 (s, 1H), 2.99-2.93 (t, 2H, J=7.8 Hz), 2.66-2.61 (t, 2H, J=7.8 Hz); $^{13}$CNMR (CDCl$_3$) δ 173.0, 141.1, 135.0, 131.8, 131.7, 128.4, 123.7, 122.4, 120.8, 90.0, 88.0, 82.8, 77.7, 51.6, 35.3, 30.8; EI-MS m/z 288 (M$^+$).

Example A18

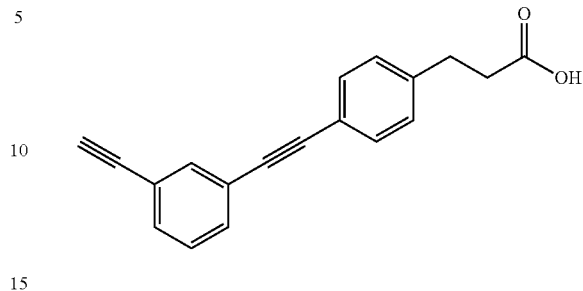

3-(4-((3-Ethynylphenyl)ethynyl)phenyl)propanoic acid. The title compound was prepared from methyl 3-(4-((3-ethynylphenyl)ethynyl)phenyl)propanoate (52 mg, 0.18 mmol) according to the general procedure II to give 38 mg (76%) of the pure title compound as an yellow solid. $R_f$: 0.16 ([EtOAc with 1.25% AcOH]:hexanes, 1:2); $^1$HNMR (CDCl$_3$) δ 12.10-9.00 (s, 1H), 7.62-7.31 (m, 8H), 3.72 (s, 1H), 2.97-2.93 (t, 2H, J=7.8 Hz), 2.67-2.62 (t, 2H, J=7.8 Hz); $^{13}$CNMR (CDCl$_3$) δ 173.8, 143.1, 135.3, 132.6, 132.5, 130.1, 129.9, 129.6, 124.7, 123.7, 121.3, 90.9, 88.4, 83.2, 80.0, 35.5, 31.4; ESI-HRMS calcd for $C_{19}H_{14}O_2$(MNa$^+$): 297.0887. found: 297.0878.

Example E19

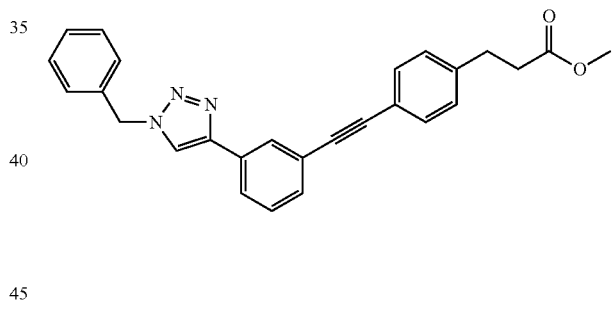

Methyl 3-(4-((3-(1-benzyl-1H-1,2,3-triazol-4-yl)phenyl)ethynyl)phenyl)propanoate. A 10 mL round bottomed flask was added H$_2$O (1 mL), NaN$_3$ (52 mg, 0.80 mmol), sodium ascorbate (11 mg, 0.05 mmol) and CuSO$_4$ (3 mg, 0.02 mmol) and stirred to dissolution before addition of DMF (1 mL) followed by benzyl bromide (0.03 mL, 0.25 mmol) and methyl 3-(4-((3-ethynylphenyl)ethynyl)phenyl)propanoate (76 mg, 0.26 mmol). The reaction was heated to 70° C. for one day, cooled to room temperature. before separation between DCM and H$_2$O. The water phase was extracted further with DCM twice. The organic phases were combined, washed with H$_2$O, dried over MgSO$_4$ and concentrated under vacuum before purification by flash chromatography (SiO$_2$, EtOAc/hexanes, 1:3→1:1) to give 58 mg (53%) of a pale yellow solid. $R_f$: 0.22 (EtOAc:hexanes, 1:2); $^1$HNMR (CDCl$_3$) δ 7.93-7.92 (m, 1H), 7.81-7.78 (m, 1H), 7.67 (s, 1H), 7.47-7.29 (m, 9H), 7.19-7.16 (m, 2H), 5.57 (s, 2H), 3.67 (s, 3H), 2.99-2.93 (t, 2H, J=7.8 Hz), 2.66-2.60 (t, 2H, J=7.8 Hz); $^{13}$CNMR (CDCl$_3$) δ 173.1, 147.4, 141.0, 134.5, 131.7, 131.1, 130.8, 129.2, 128.8, 128.3, 128.1, 125.4, 123.9, 121.0, 119.7, 89.7, 88.7, 54.3, 51.6, 35.3, 30.8; EI-MS m/z 421 (M$^+$).

Example A19

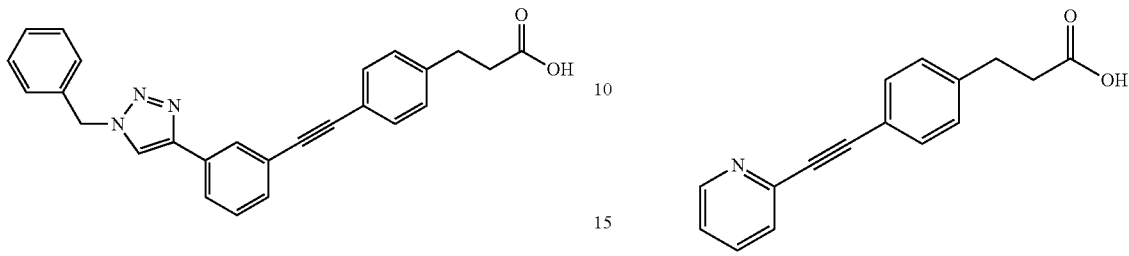

3-(4-((3-(1-Benzyl-1H-1,2,3-triazol-4-yl)phenyl)ethynyl)phenyl)propanoic acid. The title compound was prepared from methyl 3-(4-((3-(1-benzyl-1H-1,2,3-triazol-4-yl)phenyl)ethynyl)phenyl)propanoate (52 mg, 0.12 mmol) according to the general procedure II to give 50 mg (100%) of the pure title compound as an white solid. $R_f$: 0.70 (MeOH); $^1$HNMR (CDCl$_3$) δ 7.92-7.91 (m, 1H), 7.81-7.78 (m, 1H), 7.68 (s, 1H), 7.47-7.30 (m, 9H), 7.20-7.18 (m, 2H), 5.57 (s, 2H), 3.00-2.95 (t, 2H, J=7.8 Hz), 2.71-2.66 (t, 2H, J=7.8 Hz); $^{13}$CNMR (CDCl$_3$) δ 177.7, 147.4, 140.7, 134.5, 131.8, 131.1, 130.6, 129.2, 128.9, 128.8, 128.4, 128.1, 125.4, 123.9, 121.1, 119.7, 89.7, 88.8, 54.3, 35.2, 30.5; ESI-HRMS calcd for C$_{26}$H$_{21}$N$_3$O$_2$ (MNa$^+$): 430.1527. found: 430.1517.

Example A20

3-(4-(Pyridin-2-ylethynyl)phenyl)propanoic acid. The title compound was prepared from methyl 3-(4-(pyridin-2-ylethynyl)phenyl)propanoate (54 mg, 0.20 mmol) according to the general procedure II to give 39 mg (77%) of the pure title compound as an yellow solid. $R_f$: 0.16 ([EtOAc with 1.25% AcOH]:hexanes, 1:1); $^1$HNMR (CDCl$_3$) δ 8.64-8.63 (m, 1H), 7.74-7.68 (m, 1H), 7.63-7.49 (m, 3H), 7.29-7.21 (m, 3H), 3.02-2.97 (t, 2H, J=7.8 Hz), 2.73-2.68 (t, 2H, J=7.8 Hz); $^{13}$CNMR (CDCl$_3$) δ 177.0, 149.4, 142.9, 141.9, 136.8, 132.2, 128.4, 127.2, 122.9, 119.9, 90.3, 87.6, 35.2, 30.9, 30.6; MALDI-MS calcd for C$_{16}$H$_{13}$NO$_2$ (M$^+$): 252.1019. found: 252.1008.

Example E20

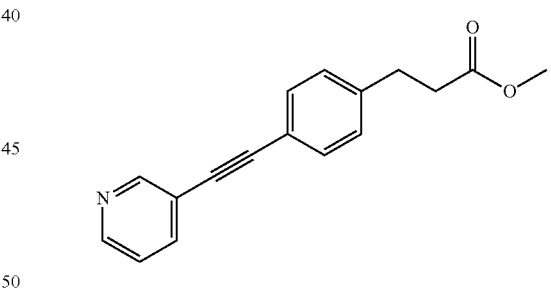

Methyl 3-(4-(pyridin-2-ylethynyl)phenyl)propanoate. The title compound was prepared from methyl 3-(4-ethynylphenyl)propanoate (99 mg, 0.52 mmol) and 2-iodopyridine (0.07 mL, 0.66 mmol) according to the general procedure IC to give 69 mg (50%) of a pale yellow solid after purification by flash chromatography (SiO$_2$, EtOAc/hexanes, 1:3). $R_f$: 0.09 (EtOAc:hexanes, 1:5); $^1$HNMR (CDCl$_3$) δ 8.62-8.60 (m, 1H), 7.70-7.64 (m, 1H), 7.54-7.49 (m, 3H), 7.25-7.18 (m, 3H), 3.67 (s, 3H), 2.99-2.94 (t, 2H, J=7.8 Hz), 2.67-2.61 (t, 2H, J=7.8 Hz); $^{13}$CNMR (CDCl$_3$) δ 173.0, 150.0, 143.5, 141.6, 136.1, 132.2, 128.4, 127.1, 122.6, 120.2, 89.2, 88.4, 51.6, 35.2, 30.8; EI-MS calcd for C$_{17}$H$_{15}$NO$_2$ (M$^+$): 265. found: 265.

Example E21

Methyl 3-(4-(pyridin-3-ylethynyl)phenyl)propanoate. The title compound was prepared from methyl 3-(4-ethynylphenyl)propanoate (102 mg, 0.54 mmol) and 3-iodopyridine (122 mg, 0.60 mmol) according to the general procedure IC to give 27 mg (43% b.r.s.m.) of an orange brown solid after purification by flash chromatography (SiO$_2$, EtOAc/hexanes, 1:3). $R_f$: 0.09 (EtOAc:hexanes, 1:5); $^1$HNMR (CDCl$_3$) δ 8.76-7.75 (m, 1H), 7.54-7.52 (m, 1H), 7.81-7.77 (m, 1H), 7.48-7.45 (m, 2H), 7.29-7.25 (m, 1H), 7.22-7.19 (m, 2H), 3.67 (s, 3H), 3.00-2.95 (t, 2H, J=7.8 Hz), 2.67-2.62 (t, 2H, J=7.8 Hz); $^{13}$CNMR (CDCl$_3$) δ 173.0, 152.2, 148.4, 141.5, 138.3, 131.8, 128.4, 123.0, 120.5, 120.4, 92.5, 85.7, 51.6, 35.3, 30.8; EI-MS calcd for C$_{17}$H$_{15}$NO$_2$ (M$^+$): 265. found: 265.

Example A21

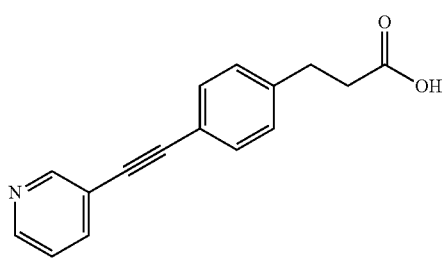 [SMILES: O=C(O)CCc1ccc(C#Cc2cccnc2)cc1]

3-(4-(Pyridin-3-ylethynyl)phenyl)propanoic acid. The title compound was prepared from methyl 3-(4-(pyridin-3-ylethynyl)phenyl)propanoate (24 mg, 0.09 mmol) according to the general procedure II to give 18 mg (79%) of the pure title compound as an orange solid. $R_f$: 0.16 ([EtOAc with 1.25% AcOH]:hexanes, 1:1); $^1$HNMR ((CD$_3$)$_2$CO) δ 12.60-10.70 (s, 1H), 8.73-8.72 (m, 1H), 8.57-8.55 (m, 1H), 7.93-7.89 (m, 1H), 7.52-7.49 (m, 2H), 7.44-7.40 (m, 1H), 7.36-7.33 (m, 2H), 2.98-2.93 (t, 2H, J=7.8 Hz), 2.67-2.62 (t, 2H, J=7.8 Hz); $^{13}$CNMR ((CD$_3$)$_2$CO) δ 173.8, 152.6, 149.6, 143.4, 139.1, 132.5, 129.6, 124.3, 121.0, 93.2, 86.3, 35.5, 31.4; MALDI-MS calcd for C$_{16}$H$_{13}$NO$_2$ (M$^+$): 252.1019. found: 252.1015.

Example A22

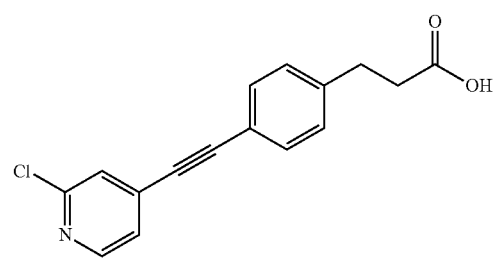

3-(4-((2-Chloropyridin-4-yl)ethynyl)phenyl)propanoic acid. The title compound was prepared from methyl 3-(4-((2-chloropyridin-4-yl)ethynyl)phenyl)propanoate (73 mg, 0.24 mmol) according to the general procedure II to give 62 mg (90%) of the pure title compound as a pale yellow solid. $R_f$: 0.09 (EtOAc:hexanes, 1:1); $^1$HNMR (DMSO) δ 14.50-13.20 (s, 1H), 12.17 (s, 1H), 8.46-8.45 (m, 1H), 7.69-7.68 (m, 1H), 7.55-7.53 (m, 3H), 7.36-7.33 (m, 2H), 2.90-2.85 (t, 2H, J=7.8 Hz), 2.60-2.55 (t, 2H, J=7.8 Hz); $^{13}$CNMR (DMSO) δ 173.5, 150.6, 150.2, 143.3, 133.6, 131.8, 128.8, 125.4, 124.6, 95.3, 85.1, 34.6, 30.2; MALDI-MS calcd for C$_{16}$H$_{12}$ClNO$_2$ (M$^+$): 286.0629. found: 286.0626.

Example E22

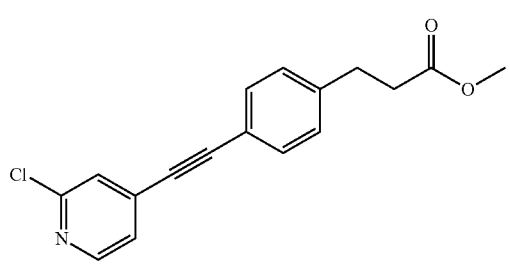 [SMILES: COC(=O)CCc1ccc(C#Cc2ccnc(Cl)c2)cc1]

Methyl 3-(4-((2-chloropyridin-4-yl)ethynyl)phenyl)propanoate. The title compound was prepared from methyl 3-(4-ethynylphenyl)propanoate (104 mg, 0.55 mmol) and 2-chloro-4-iodopyridine (141 mg, 0.59 mmol) according to the general procedure IC to give 96 mg (58%) of a pale yellow solid after purification by flash chromatography (SiO$_2$, EtOAc/hexanes, 1:5). $R_f$: 0.22 (EtOAc:hexanes, 1:5); $^1$HNMR (CDCl$_3$) δ 8.36-8.35 (m, 1H), 7.48-7.45 (m, 2H), 7.42-7.41 (m, 1H), 7.29-7.26 (m, 1H), 7.24-7.21 (m, 2H), 3.67 (s, 3H), 3.01-2.96 (t, 2H, J=7.8 Hz), 2.67-2.62 (t, 2H, J=7.8 Hz); $^{13}$CNMR (CDCl$_3$) δ 172.9, 151.7, 149.5, 142.4, 134.4, 132.1, 128.6, 125.9, 124.1, 95.4, 85.3, 51.8, 35.2, 30.8; EI-MS calcd for C$_{17}$H$_{15}$ClNO$_2$ (M$^+$): 299. found: 299.

Example E23

Methyl 3-(4-((6-methylpyridin-2-yl)ethynyl)phenyl)propanoate. The title compound was prepared from methyl 3-(4-ethynylphenyl)propanoate (99 mg, 0.53 mmol) and 2-bromo-4-methylpyridine (0.07 mL, 0.61 mmol) according to the general procedure IC to give 61 mg (41%) of a beige solid after purification by flash chromatography (SiO$_2$, EtOAc/hexanes, 1:3). $R_f$: 0.07 (EtOAc:hexanes, 1:5); $^1$HNMR (CDCl$_3$) δ 7.58-7.51 (m, 3H), 7.35-7.32 (m, 1H), 7.20-7.17 (m, 2H), 7.11-7.08 (m, 1H), 3.67 (s, 3H), 2.99-2.94 (t, 2H, J=7.8 Hz), 2.66-2.61 (t, 2H, J=7.8 Hz), 2.58 (s, 3H); $^{13}$CNMR (CDCl$_3$) δ 173.0, 158.9, 142.8, 141.5, 136.3, 132.2, 128.3, 124.3, 122.4, 120.3, 88.7, 88.7, 51.6, 35.2, 30.8, 24.6; EI-MS calcd for C$_{18}$H$_{17}$NO$_2$ (M$^+$): 279. found: 279.

Example A23

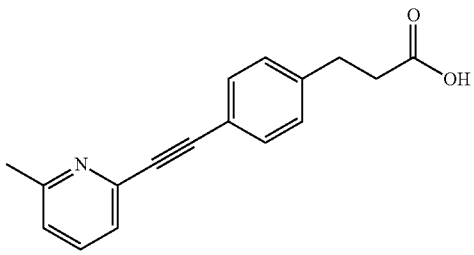 [SMILES: Cc1cccc(C#Cc2ccc(CCC(=O)O)cc2)n1]

3-(4-((6-Methylpyridin-2-yl)ethynyl)phenyl)propanoic acid. The title compound was prepared from methyl 3-(4-((4-methylpyridin-2-yl)ethynyl)phenyl)propanoate (51 mg, 0.18 mmol) according to the general procedure II to give 22 mg (45%) of the pure title compound as a pale yellow solid. $R_f$: 0.06 (EtOAc:hexanes, 1:1); $^1$HNMR (DMSO) δ 7.58-7.51 (m, 3H), 7.35-7.32 (m, 1H), 7.20-7.17 (m, 2H), 7.11-7.08 (m, 1H), 3.67 (s, 3H), 2.99-2.94 (t, 2H, J=7.8 Hz), 2.66-2.61 (t, 2H, J=7.8 Hz), 2.58 (s, 3H); $^{13}$CNMR (DMSO) δ 173.0, 158.9, 142.8, 141.5, 136.3, 132.2, 128.3, 124.3, 122.4, 120.3, 88.7, 88.7, 51.6, 35.2, 30.8, 24.6; MALDI-MS calcd for $C_{17}H_{15}NO_2$ (MH$^+$): 266.1176. found: 266.1168.

Example E24

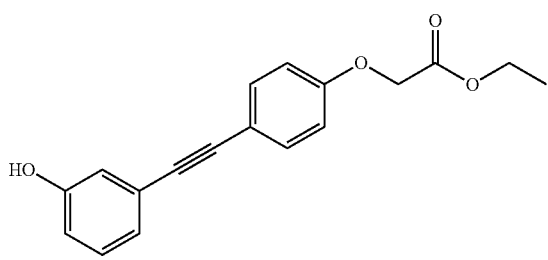 [SMILES: CCOC(=O)COc1ccc(C#Cc2cccc(O)c2)cc1]

Ethyl 2-(4-((3-hydroxyphenyl)ethynyl)phenoxy)acetate. To a dried Schlenk flask filled with nitrogen was added Pd(PPh$_3$)$_4$ (17.3 mg, 0.015 mmol), CuI (6.6 mg, 0.035 mmol), ethyl 2-(4-ethynylphenoxy)acetate (60.6 mg, 0.294 mmol), and 3-iodophenol (78.4 mg, 0.352 mmol) was added. The flask was evacuated, equipped with a septum, and filled with nitrogen. DMF (5 mL) and DIPEA (0.1 mL, 0.6 mmol) were added through the septum. The reaction was stirred overnight and was neutralized with saturated aqueous ammonium chloride (5 mL). Water (5 mL) was added and the mixture was extracted with EtOAc (3×10 mL). The combined EtOAc phases was washed with brine, dried over MgSO$_4$, and concentrated under reduced pressure. The product was purified on a dry silica column (EtOAc:hexanes 1:90→90:1 v/v). The final product was yellow/orange and solid (52 mg, 60%). $R_f$=0.46 (EtOAc:hexanes 1:1 v/v). $^1$H-NMR (DMSO-d$_6$): □ 1.22 (t, 3H, J=7.7 Hz, CH$_2$CH$_3$); 4.18 (q, 2H, J=7.5 Hz, CH$_2$CH$_3$); 4.84 (s, 2H, OCH$_2$); 6.9 (m, 5H, Ph); 7.20 (t, 1H, J=8.0 Hz, Ph); 7.49 (m, 2H, Ph); 9.67 (s, 1H, OH). $^{13}$C-NMR (DMSO-d$_6$): □ 14.0 (CH$_2$CH$_3$); 60.7 (CH$_2$CH$_3$); 64.7 (OCH$_2$); 88.3 (CC); 88.6 (CC); 115.0, 116.0, 117.6, 122.1, 123.4, 128.4, 129.8, 132.9, 157.3, 157.8 (Ph); 168.5 (COO).

Example A24

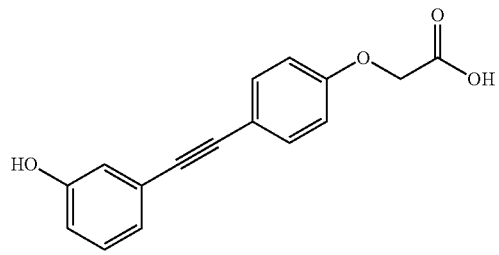

2-(4-((3-Hydroxyphenyl)ethynyl)phenoxy)ethanoic acid. Ethyl 2-(4-((3-hydroxyphenyl)ethynyl)phenoxy)acetate (48.0 mg, 0.162 mmol) was dissolved in THF (1 mL), and LiOH.H2O (20.4 mg, 0.486 mmol) in water (1 mL) was added. The mixture was stirred over night. and 14% HCl (0.2 mL) was added until pH<1. Water (10 mL) was added, and the mixture was extracted with EtOAc (3×10 mL). The combined EtOAc phases was washed with brine (10 mL), dried over MgSO$_4$, and concentrated under reduced pressure. The product was white/yellow and solid (39.5 mg, 92%). $R_f$=0.02 (EtOAc:hexanes 1:1 v/v). $^1$H-NMR (DMSO-d$_6$): □ 4.52 (s, 2H, CH$_2$OH); 7.1 (m, 8H, Ph); 9.71 (s, 1H, OH); 12.94 (s, 1H, COOH). $^{13}$C-NMR (DMSO-d$_6$): □ 64.5 (OCH$_2$); 88.2 (CC); 88.7 (CC); 114.7, 114.9, 116.0, 117.6, 122.0, 123.5, 129.8, 132.9, 157.3, 158.0 (Ph); 169.9 (COO). EI-MS: m/z calculated for $C_{16}H_{12}O_4$ [M]$^+$268; [$C_{14}H_9O_2$]$^+$209; [$C_8H_8O_3$]$^+$ 152. found 268, 207, 152.

Example E25

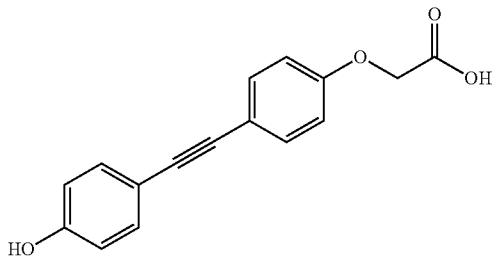

Ethyl 2-(4-((4-hydroxyphenyl)ethynyl)phenoxy)acetate. To a dried Schlenk flask filled with nitrogen was added Pd(PPh$_3$)$_4$ (56.5 mg, 0.049 mmol), CuI (14.2 mg, 0.075 mmol), ethyl 2-(4-ethynylphenoxy)acetate (150.0 mg, 0.734 mmol), and 4-iodophenol (195.3 mg, 0.888 mmol) was added. The flask was evacuated, equipped with a septum, and filled with nitrogen. DMF (10 mL) and DIPEA (0.26 mL, 1.5 mmol) were added through the septum. The reaction was stirred for 3 days and was neutralized with saturated aqueous NH$_4$Cl (5 mL). Water (5 mL) was added and the mixture was extracted with EtOAc (3×10 mL). The combined EtOAc phases was washed with brine, dried over MgSO$_4$, and concentrated under reduced pressure. The product was purified with dry column vacuum chromatography (EtOAc:hexanes 1:90→90:1 v/v). The final product was white and solid (129.6 mg, 60%) $R_f$=0.48 (EtOAc:hexanes 1:1 v/v). $^1$H-NMR (DMSO-$d_6$): □ 1.21 (t, 3H, J=7.2 Hz, CH$_2$CH$_3$); 4.17 (q, 2H, J=7.1 Hz, CH$_2$CH$_3$); 4.82 (s, 2H, OCH$_2$); 6.78 (d, 2H, J=8.7 Hz, Ph); 6.95 (d, 2H, J=9.0 Hz, Ph); 7.34 (d, 2H, J=8.7 Hz, Ph); 7.43 (d, 2H, J=8.7 Hz, Ph); 9.67 (s, 1H, OH). $^{13}$C-NMR (DMSO-$d_6$): □ 14.0 (CH$_2$CH$_3$); 60.7 (CH$_2$CH$_3$); 64.7 (OCH$_2$); 87.1 (CC); 88.6 (CC); 112.8, 114.9, 115.6, 115.7, 132.6, 132.8, 157.5, 157.8 (Ph); 168.5 (COO). MALDI-MS: m/z calculated for $C_{18}H_{16}O_3$ [M]$^+$ 296.1043. found 296.1046.

Example A25

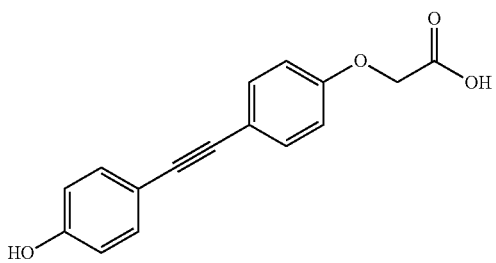 [SMILES: O=C(O)COc1ccc(C#Cc2ccc(O)cc2)cc1]

2-(4-((4-Hydroxyphenyl)ethynyl)phenoxy)ethanoic acid. Ethyl 2-(4-((4-hydroxyphenyl)ethynyl)phenoxy)acetate (39.9 mg, 0.135 mmol) was dissolved in THF (1.5 mL) and LiOH.H2O (17.0 mg, 0.405 mmol) in water (1 mL) was added. The mixture was stirred for 2 h. and 14% HCl (0.2 mL) was added until pH<1. Water (10 mL) was added, and the mixture was extracted with EtOAc (3×10 mL). The combined EtOAc phases was washed with brine (10 mL), dried over MgSO$_4$, and concentrated under reduced pressure. The product was white/yellow and solid (35.7 mg, 97%) $R_f$=0.01 (EtOAc:hexanes 1:1 v/v). $^1$H-NMR (DMSO-$d_6$):□ 4.71 (s, 2H, OCH$_2$); 6.78 (d, 2H, J=8.7 Hz, Ph); 6.93 (d, 2H, J=8.7 Hz, Ph); 7.33 (d, 2H, J=8.1 Hz, Ph); 7.43 (d, 2H, J=8.4 Hz, Ph); 9.87 (s, 1H, OH); 13.00 (s, 1H, COOH). $^{13}$C-NMR (DMSO-$d_6$):□ 64.5 (OCH$_2$); 87.2 (CC); 88.6 (CC); 112.8, 114.8, 115.4, 115.7, 132.5, 132.8, 157.6, 157.8 (Ph); 170.0 (COO). MALDI-MS: m/z calculated for $C_{16}H_{12}O_3$ [M]$^+$ 268.0730. found 268.0739.

Example E26

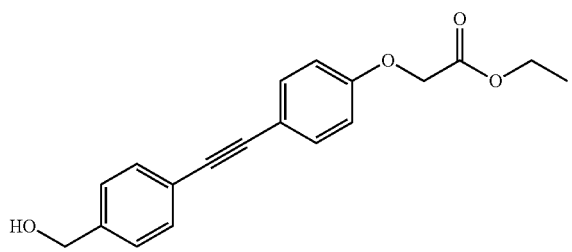 [SMILES: CCOC(=O)COc1ccc(C#Cc2ccc(CO)cc2)cc1]

Ethyl 2-(4-((4-(hydroxymethyl)phenyl)ethynyl)phenoxy) acetate. To a dried Schlenk flask filled with nitrogen was added Pd(PPh$_3$)$_4$ (19.6 mg, 0.017 mmol), CuI (4.6 mg, 0.024 mmol), ethyl 2-(4-ethynylphenoxy)acetate (49.6 mg, 1.50 mmol), and (4-iodophenyl)methanol (68.2 mg, 0.291 mmol) was added. The flask was evacuated, equipped with a septum, and filled with nitrogen. DMF (5 mL) and DIPEA (0.1 mL, 0.486 mmol) were added through the septum. The reaction was stirred over night and was neutralized with saturated aqueous ammonium chloride (5 mL). Water (5 mL) was added and the mixture was extracted with EtOAc (3×15 mL). The combined EtOAc phases was washed with brine, dried over MgSO$_4$, and concentrated under reduced pressure. The product was purified on a dry silica column (EtOAc:hexanes 1:90→90:1 v/v). The final product was white/yellow and solid (58.0 mg, 77%). $R_f$=0.36 (EtOAc:hexanes 1:1 v/v). $^1$H-NMR (CDCl$_3$): □ 1.29 (t, 3H, J=7.2 Hz, CH$_2$CH$_3$); 1.80 (m, 1H, OH); 4.27 (q, 2H, J=7.2 Hz, CH$_2$CH$_3$); 4.63 (s, 2H, OCH$_2$); 4.69 (d, 2H, J=5.4 Hz, CH$_2$OH); 6.82 (m, 2H, Ph); 7.40 (m, 7H, Ph, OH). $^{13}$C-NMR (CDCl$_3$): □ 14.1 (CH$_2$CH$_3$); 61.5 (CH$_2$CH$_3$); 65.0 (CH$_2$OH); 65.3 (OCH$_2$); 88.2 (CC); 89.1 (CC); 114.7, 116.5, 122.7, 126.8, 131.6, 133.1, 140.8, 157.8 (Ph); 168.6 (COO).

Example A26

2-(4-((4-(Hydroxymethyl)phenyl)ethynyl)phenoxy)ethanoic acid. Ethyl 2-(4-((4-(hydroxymethyl)phenyl)ethynyl) phenoxy)acetate (54.0 mg, 0.174 mmol) was dissolved in THF (1 mL), and LiOH.H2O (10.9 mg, 0.261 mmol) in water (0.5 mL) was added. The mixture was stirred for 1.5 h. and 3% HCl (0.5 mL) was added until pH<1. Water (10 mL) was added, and the mixture was extracted with EtOAc (3×10 mL). The combined EtOAc phases was washed with brine (10 mL), dried over MgSO$_4$, and concentrated under reduced pressure. The product was white/yellow and solid (48.0 mg, 98%). $R_f$=0.04 (EtOAc:hexanes 1:1 v/v). $^1$H-NMR (DMSO-$d_6$): □ 4.52 (s, 2H, CH$_2$OH); 4.73 (s, 2H, OCH$_2$); 5.26 (s, 1H, CH$_2$OH); 6.95 (d, 2H, J=8.7 Hz, Ph); 7.35 (d, 2H, J=7.8 Hz, Ph); 7.48 (m, 4H, Ph); 12.99 (s, 1H, COOH). $^{13}$C-NMR (DMSO-$d_6$):□ 62.0 (CH$_2$OH); 64.0 (OCH$_2$); 87.7 (CC); 88.3 (CC); 114.3, 114.4, 120.3, 126.1, 130.5, 132.3, 142.6, 157.5 (Ph); 169.4 (COO). EI-MS: m/z calculated for $C_{17}H_{14}O_4$ [M]$^+$ 282; [$C_{15}H_{11}O_2$]$^+$ 223; [$C_8H_8O_3$]$^+$ 152. found 282, 223, 152.

Example E27

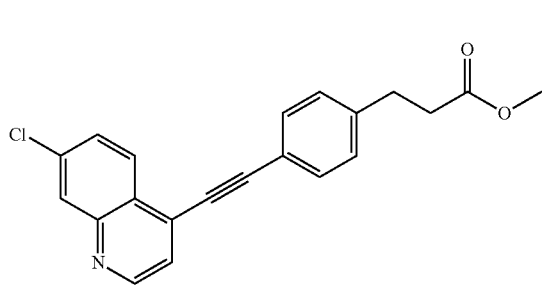 [SMILES: COC(=O)CCc1ccc(C#Cc2ccnc3cc(Cl)ccc23)cc1]

Methyl 3-(4-((7-chloroquinolin-4-yl)ethynyl)phenyl)propanoate. The title compound was prepared from methyl 3-(4-ethynylphenyl)propanoate (54 mg, 0.29 mmol) and 7-chloro-4-iodoquinoline (93 mg, 0.32 mmol) according to the general procedure IC to give 54 mg (54%) of a beige solid after purification by flash chromatography (SiO$_2$, EtOAc:PE, 1:4). R$_f$=0.06 (EtOAc:PE, 1:4); $^1$H NMR (CDCl$_3$) δ 8.88 (d, J=4.8 Hz, 1H), 8.27 (d, J=9.0 Hz, 1H), 8.11 (m, 1H), 7.59-7.52 (m, 4H), 7.28-7.25 (m, 2H), 3.69 (s, 3H), 3.01 (t, J=7.8 Hz, 2H), 2.67 (t, J=7.8 Hz, 2H); $^{13}$C NMR (CDCl$_3$) δ 172.9, 150.8, 148.5, 142.4, 135.8, 132.1, 129.9, 128.8, 128.6, 128.1, 127.4, 126.1, 123.5, 119.9, 99.2, 84.4, 51.7, 35.2, 30.9; ESI-MS m/z 372.1 (M+Na$^+$).

Example A27

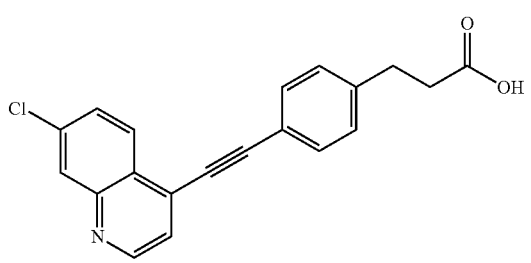 [SMILES: O=C(O)CCc1ccc(C#Cc2ccnc3cc(Cl)ccc23)cc1]

3-(4-((7-Chloroquinolin-4-yl)ethynyl)phenyl)propanoic acid. The title compound was prepared from methyl 3-(4-((7-chloroquinolin-4-yl)ethynyl)phenyl)propanoate (50 mg, 0.14 mmol) according to the general procedure II to give 43 mg (90%) of the pure title compound as a beige solid: R$_f$=0.12 ([EtOAc with 1.25% AcOH]:PE, 1:2); $^1$H NMR (DMSO-d$_6$) δ 12.20 (br s, OH), 8.96 (d, J=4.5 Hz, 1H), 8.37 (d, J=8.7 Hz, 1H), 8.15-8.14 (m, 1H), 7.78-7.74 (m, 2H), 7.68 (d, J=8.1 Hz, 2H), 7.39 (d, J=8.1 Hz, 2H), 2.91 (t, J=7.5 Hz, 2H), 2.60 (t, J=7.7 Hz, 2H); $^{13}$C NMR (DMSO-d$_6$) δ 173.6, 151.5, 147.9, 143.4, 134.8, 132.0, 128.9, 128.6, 128.3, 128.2, 127.8, 125.4, 124.0, 118.6, 99.3, 84.0, 34.7, 30.3; ESI-MS calcd for O$_{20}$H$_{14}$ClNO$_2$ (M+Na$^+$) 336.0786. found 336.0785.

Example E28

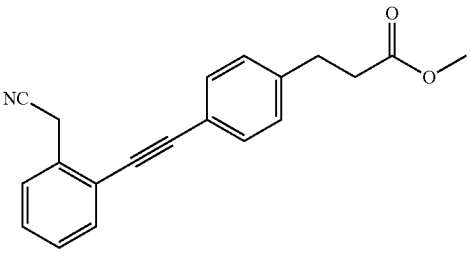 [SMILES: COC(=O)CCc1ccc(C#Cc2ccccc2CC#N)cc1]

Methyl 3-(4-((2-(cyanomethyl)phenyl)ethynyl)phenyl)propanoate. The title compound was prepared from methyl 3-(4-ethynylphenyl)propanoate (74 mg, 0.39 mmol) and 2-(2-iodophenyl)acetonitrile (60 μL, 0.43 mmol) according to the general procedure IC to give 74 mg (62%) of an orange solid after purification by flash chromatography (SiO$_2$, EtOAc:PE, 1:4). R$_f$=0.08 (EtOAc:PE, 1:4); $^1$H NMR (CDCl$_3$) δ 7.55-7.46 (m, 4H), 7.37-7.34 (m, 2H), 7.21 (d, J=8.4 Hz, 2H), 3.96 (s, 2H), 3.67 (s, 3H), 2.97 (t, J=7.7 Hz, 2H), 2.64 (t, J=7.5 Hz, 2H); $^{13}$C NMR (CDCl$_3$) δ 173.0, 141.6, 132.3, 131.7, 131.6, 128.9, 128.5, 128.1, 122.9, 120.4, 117.4, 95.6, 85.7, 51.7, 35.3, 30.8, 22.7; ESI-MS m/z 326.1 (M+Na$^+$).

Example A28

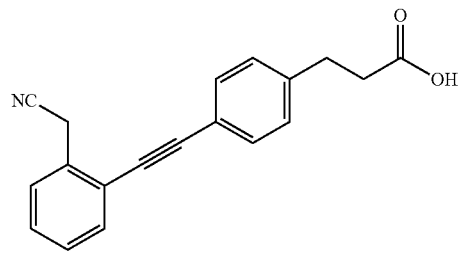 [SMILES: N#CCc1ccccc1C#Cc1ccc(CCC(=O)O)cc1]

3-(4-((2-(Cyanomethyl)phenyl)ethynyl)phenyl)propanoic acid. The title compound was prepared from methyl 3-(4-((2-(cyanomethyl)phenyl)ethynyl)phenyl)propanoate (66 mg, 0.22 mmol) according to the general procedure II to give 48 mg (76%) of the pure title compound as a brown solid: R$_f$=0.28 (SiO$_2$, [EtOAc with 1.25% AcOH]:PE, 1:1); 1H NMR (DMSO-d$_6$) δ 11.87 (br s, OH), 7.31-7.21 (m, 4H), 7.16-7.12 (m, 2H), 7.03-7.00 (m, 2H), 3.87 (s, 2H), 2.57 (t, J=7.5 Hz, 2H), 2.27 (t, J=7.5 Hz, 2H); $^{13}$C NMR (DMSO-d$_6$) δ 173.6, 142.3, 132.8, 132.0, 131.4, 129.3, 128.9, 128.7, 128.3, 122.2, 119.6, 118.4, 95.3, 85.9, 34.8, 30.3, 22.1; ESI-MS calcd for C$_{19}$H$_{15}$NO$_2$ (M+Na$^+$) 312.0995. found 312.1002.

Intermediate-5

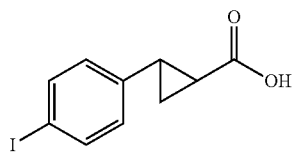 [SMILES: O=C(O)C1CC1c1ccc(I)cc1]

trans-2-(4-Iodophenyl)cyclopropanecarboxylic acid. A solution of H$_2$SO$_4$ (0.1 mL) in water (1 mL) and AcOH (4 mL) in a 25 mL flask was added trans-2-phenylcyclopropanecarboxylic acid (200 mg, 1.23 mmol), iodine (173 mg, 0.68 mmol) and KIO$_3$ (61 mg, 0.28 mmol). The reaction mixture was heated to reflux, and added AcOH (6 mL) in portions of 2 mL to rinse iodine down the condenser. After 4 hours, when no further color changes appeared, the reaction was cooled to room temperature, quenched with 1M Na$_2$S$_2$O$_4$ and added water. The mixture was extracted with EtOAc (3×), and the combined extracts were washed with brine, dried over MgSO$_4$ and concentrated under vacuum. The crude product containing minor impurities of starting material and the ortho-iodinated product, was recrystallized from PE to provide 157 mg (44%) trans-2-(4-iodophenyl)cyclopropanecarboxylic acid as a pure and white crystalline product: R$_t$=11.33 min (HPLC method I); $^1$H NMR (CDCl$_3$) δ 7.62-7.58 (m, 2H), 6.87-6.84 (m, 2H), 2.56-2.51 (m, 1H), 1.89-1.84 (m, 1H), 1.69-1.64 (m, 1H), 1.39-1.34 (m, 1H); $^{13}$C NMR (CDCl$_3$) δ 179.3, 139.2, 137.6, 128.3, 91.7, 26.5, 23.9, 17.4; ESI-MS m/z 311.0 (M+Na$^+$).

Example A29

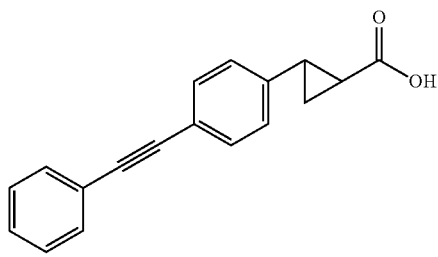 [SMILES: O=C(O)C1CC1c1ccc(C#Cc2ccccc2)cc1]

trans-2-(4-(Phenylethynyl)phenyl)cyclopropanecarboxylic acid. The title compound was prepared from ethynylbenzene (0.05 mL, 0.46 mmol) and trans-2-(4-iodophenyl)cyclopropanecarboxylic acid (100 mg, 0.35 mmol) according to the general procedure IC to give 47 mg (53%) of a white solid after purification by flash chromatography (SiO$_2$, EtOAc:PE, 1:2→1:0): R$_t$=12.54 min (HPLC method I); $^1$H NMR (CDCl$_3$) δ 7.53-7.51 (m, 2H), 7.47-7.44 (m, 2H), 7.36-7.31 (m, 3H), 7.09-7.07 (m, 2H), 2.63-2.58 (m, 1H), 1.95-1.90 (m, 1H), 1.72-1.67 (m, 1H), 1.44-1.39 (m, 1H); $^{13}$C NMR (CDCl$_3$) δ 179.5, 140.0, 131.9, 131.7, 128.5, 128.4, 126.4, 123.4, 121.8, 89.7, 89.2, 27.1, 24.3, 17.8; ESI-MS calcd for C$_{18}$H$_{14}$O$_2$ (M+Na$^+$) 285.0887. found 285.0894.

Example E30

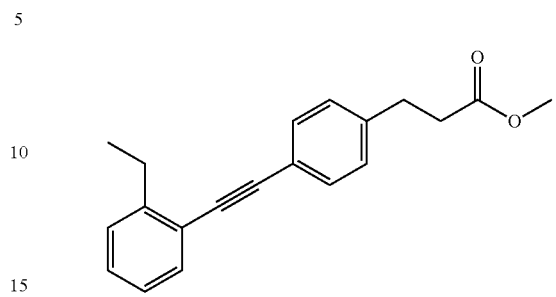

Methyl 3-(4-((2-ethylphenyl)ethynyl)phenyl)propanoate. The title compound was prepared from methyl 3-(4-ethynylphenyl)propanoate (95 mg, 0.51 mmol) and 1-bromo-2-ethylbenzene (0.10 mL, 0.73 mmol) according to the general procedure IF to give 130 mg (87%) of a clear oil after purification by flash chromatography (SiO$_2$, EtOAc:PE, 1:7): R$_f$=0.28 (EtOAc:PE, 1:4); $^1$H NMR (CDCl$_3$) δ 7.50-7.48 (m, 1H), 7.46-7.44 (m, 2H), 7.26-7.22 (m, 2H), 7.20-7.14 (m, 3H), 3.67 (s, 3H), 2.96 (t, J=7.8 Hz, 2H), 2.88 (q, J=7.2 Hz, 2H), 2.63 (t, J=7.6 Hz, 2H), 1.29 (t, J=7.6 Hz, 3H); $^{13}$C NMR (CDCl$_3$) δ 173.2, 146.3, 140.9, 132.2, 131.8, 128.6, 128.5, 128.1, 125.8, 122.5, 121.7, 92.9, 88.0, 51.8, 35.6, 31.0, 27.9, 14.9; ESI-MS m/z 315.1 (M+Na$^+$).

Example A30

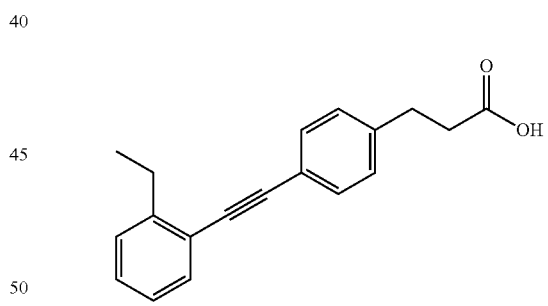

3-(4-((2-Ethylphenyl)ethynyl)phenyl)propanoic acid. The title compound was prepared from methyl 3-(4-((2-ethylphenyl)ethynyl)phenyl)propanoate (73 mg, 0.25 mmol) according to the general procedure II to give 59 mg (84%) of the pure title compound as a white solid: R$_f$=0.49 ([EtOAc with 1.25% AcOH]:PE, 1:1); $^1$H NMR (CDCl$_3$) δ 7.50-7.45 (m, 3H), 7.27-7.14 (m, 5H), 2.97 (t, J=7.6 Hz, 2H), 2.88 (q, J=7.6 Hz, 2H), 2.69 (t, J=7.8 Hz, 2H), 1.29 (t, J=7.4 Hz, 3H); $^{13}$C NMR (CDCl$_3$) δ 178.8, 146.4, 140.5, 132.3, 131.8, 128.6, 128.5, 128.1, 125.8, 122.5, 121.9, 92.8, 88.1, 35.4, 30.6, 28.0, 14.9; ESI-MS calcd for C$_{19}$H$_{18}$O$_2$ (M+Na$^+$) 301.1200. found 301.1196.

Example E31

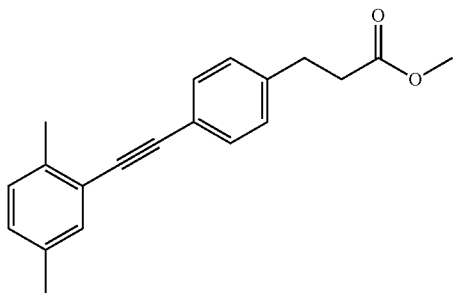 [SMILES: COC(=O)CCc1ccc(C#Cc2cc(C)ccc2C)cc1]

Methyl 3-(4-((2,5-dimethylphenyl)ethynyl)phenyl)propanoate. The title compound was prepared from methyl 3-(4-ethynylphenyl)propanoate (95 mg, 0.50 mmol) and 2-bromo-1,4-dimethylbenzene (0.08 mL, 0.60 mmol) according to the general procedure IF to give 123 mg (84%) of a clear oil after purification by flash chromatography (SiO$_2$, EtOAc:PE, 1:8): R$_f$=0.21 (EtOAc:PE, 1:8); $^1$H NMR (CDCl$_3$) δ 7.46-7.43 (m, 2H), 7.31 (s, 1H), 7.19-7.17 (m, 2H), 7.11-7.10 (m, 1H), 7.04-7.02 (m, 1H), 3.67 (s, 3H), 2.96 (t, J=7.8 Hz, 2H), 2.63 (t, J=7.8 Hz, 2H), 2.45 (s, 3H), 2.30 (s, 3H); $^{13}$C NMR (CDCl$_3$) δ 173.5, 140.8, 137.2, 135.2, 132.4, 131.8, 129.5, 129.3, 128.5, 123.0, 121.7, 93.0, 88.4, 51.8, 35.6, 31.0, 20.9, 20.3; ESI-MS m/z 315.1 (M+Na$^+$).

Example A31

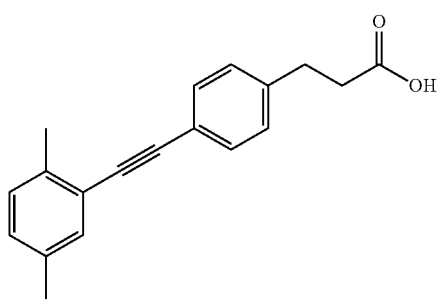 [SMILES: Cc1ccc(C)c(C#Cc2ccc(CCC(=O)O)cc2)c1]

3-(4-((2,5-Dimethylphenyl)ethynyl)phenyl)propanoic acid. The title compound was prepared from methyl 3-(4-((2,5-dimethylphenyl)ethynyl)phenyl)propanoate (65 mg, 0.22 mmol) according to the general procedure II to give 58 mg (95%) of the pure title compound as a white solid: R$_f$=0.49 ([EtOAc with 1.25% AcOH]:PE, 1:1); $^1$H NMR (CDCl$_3$) δ 7.47-7.44 (m, 2H), 7.31 (s, 1H), 7.20-7.17 (m, 2H), 7.11-7.10 (m, 1H), 7.04-7.02 (m, 1H), 2.97 (t, J=7.6 Hz, 2H), 2.69 (t, J=7.6 Hz, 2H), 2.46 (s, 3H), 2.30 (s, 3H); $^{13}$C NMR (CDCl$_3$) δ 178.8, 140.4, 137.2, 135.2, 132.4, 131.8, 129.5, 129.3, 128.5, 123.0, 121.9, 92.9, 88.5, 35.4, 30.6, 20.9, 30.4; ESI-MS calcd for C$_{19}$H$_{18}$O$_2$ (M+Na$^+$) 301.1200. found 301.1210.

Example E32

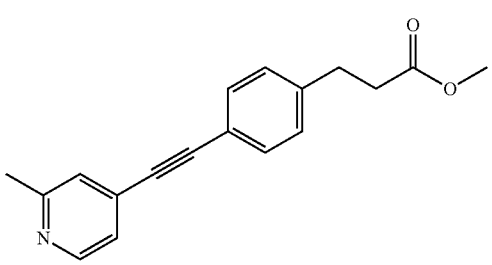

Methyl 3-(4-((2-methylpyridin-4-yl)ethynyl)phenyl)propanoate. The title compound was prepared from methyl 3-(4-ethynylphenyl)propanoate (95 mg, 0.50 mmol) and 4-iodo-2-methylpyridine (0.07 mL, 0.59 mmol) according to the general procedure IF to give 62 mg (44%) of a pale yellow solid after purification by flash chromatography (SiO$_2$, EtOAc:PE, 1:5): R$_f$=0.50 (EtOAc:PE, 1:2); $^1$H NMR (CDCl$_3$) δ 8.48-8.46 (m, 1H), 7.48-7.45 (m, 2H), 7.25-7.20 (m, 4H), 3.67 (s, 3H), 2.98 (t, J=7.8 Hz, 2H), 2.64 (t, J=7.8 Hz, 2H), 2.56 (s, 3H); $^{13}$C NMR (CDCl$_3$) δ 173.1, 158.6, 149.3, 142.0, 132.1, 131.8, 128.6, 125.1, 122.7, 120.3, 93.4, 86.9, 51.8, 35.4, 31.0, 24.5; ESI-MS m/z 302.1 (M+Na$^+$).

Example A32

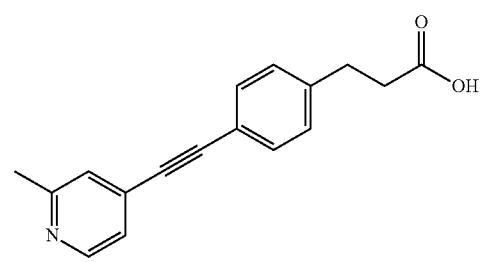 [SMILES: Cc1cc(C#Cc2ccc(CCC(=O)O)cc2)ccn1]

3-(4-((2-Methylpyridin-4-yl)ethynyl)phenyl)propanoic acid. The title compound was prepared from methyl 3-(4-((2-methylpyridin-4-yl)ethynyl)phenyl)propanoate (55 mg, 0.20 mmol) according to the general procedure II to give 58 mg (70%) of the pure title compound as a white solid: R$_f$=0.25 ([EtOAc with 1.25% AcOH]:PE, 1:1); $^1$H NMR (DMSO-d$_6$) δ 8.74 (d, J=7.6 Hz, 1H), 8.01 (s, 1H), 7.90-7.88 (m, 1H), 7.61-7.59 (m, 2H), 7.39-7.37 (m, 2H), 2.89 (t, J=7.4 Hz, 2H), 2.73 (s, 3H), 2.58 (t, J=7.6 Hz, 2H); $^{13}$C NMR (DMSO-d$_6$) δ 173.4, 154.0, 144.3, 141.5, 138.3, 132.2, 129.1, 128.7, 125.5, 117.7, 100.2, 85.5, 34.6, 30.3, 19.3; ESI-MS calcd for C$_{17}$H$_{16}$NO$_2$ (M+Na$^+$) 288.0996. found 288.0989.

Example E33

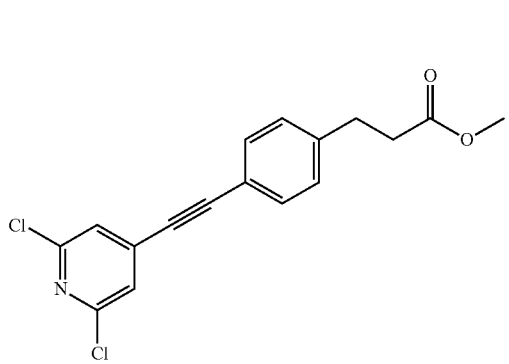 [SMILES: COC(=O)CCc1ccc(C#Cc2cc(Cl)nc(Cl)c2)cc1]

Methyl 3-(4-((2,6-dichloropyridin-4-yl)ethynyl)phenyl)propanoate. The title compound was prepared from methyl 3-(4-ethynylphenyl)propanoate (98 mg, 0.52 mmol) and 2,6-dichloro-4-iodopyridine (152 mg, 0.56 mmol) according to the general procedure IF to give 95 mg (55%) of a pale yellow solid after purification by flash chromatography (SiO$_2$, EtOAc:PE, 1:7): R$_f$=0.11 (EtOAc:PE, 1:7); $^1$H NMR (CDCl$_3$) δ 7.46 (d, J=8.3 Hz, 2H), 7.34 (s, 1H), 7.22 (s, 2H), 3.68 (s, 3H), 2.99 (t, J=7.7 Hz, 2H), 2.65 (t, J=7.7 Hz, 2H); $^{13}$C NMR (CDCl$_3$) δ 173.0, 150.7, 142.0, 132.7, 132.3, 128.7, 128.5, 124.4, 119.8, 81.4, 73.8, 51.7, 35.2, 30.9; ESI-MS m/z 356.0 (M+Na$^+$).

Example A33

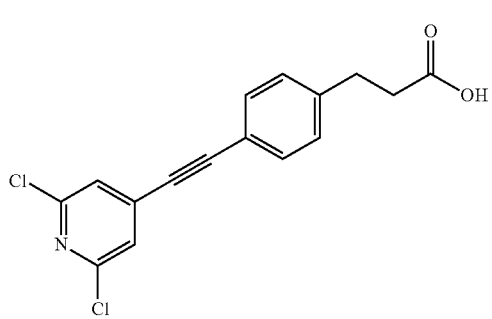 [SMILES: O=C(O)CCc1ccc(C#Cc2cc(Cl)nc(Cl)c2)cc1]

3-(4-((2,6-Dichloropyridin-4-yl)ethynyl)phenyl)propanoic acid. The title compound was prepared from methyl 3-(4-((2,6-dichloropyridin-4-yl)ethynyl)phenyl)propanoate (9 mg, 0.03 mmol) according to the general procedure II to give 7 mg (76%) of the pure title compound as a white solid: R$_f$=0.54 ([EtOAc with 1.25% AcOH]:PE, 1:1); $^1$H NMR (CDCl$_3$) δ 7.50-7.45 (m, 2H), 7.34 (s, 2H), 7.25 (d, J=8.4 Hz, 2H), 3.00 (t, J=7.6 Hz, 2H), 2.71 (t, J=7.6 Hz, 2H); $^{13}$C NMR (CDCl$_3$) δ 177.7, 150.7, 142.4, 136.5, 132.3, 128.7, 124.4, 119.3, 96.8, 84.5, 34.9, 30.5; ESI-MS calcd for C$_{16}$H$_{11}$Cl$_2$NO$_2$ (M+Na$^+$) 342.0060. found 342.0067.

Example E34

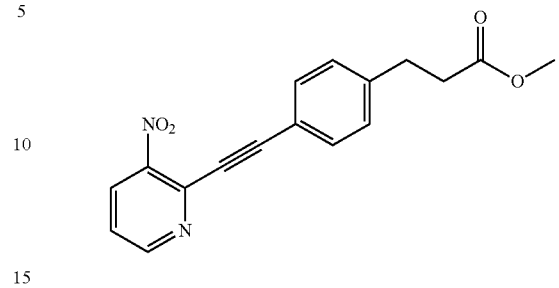

Methyl 3-(4-((3-nitropyridin-2-yl)ethynyl)phenyl)propanoate. The title compound was prepared from methyl 3-(4-ethynylphenyl)propanoate (95 mg, 0.51 mmol) and 2-bromo-3-nitropyridine (113 mg, 0.56 mmol) according to the general procedure IF to give 84 mg (53%) of a red solid after purification by flash chromatography (SiO$_2$, EtOAc:PE, 1:8): R$_f$=0.16 (EtOAc:PE, 1:4); $^1$H NMR (CDCl$_3$) δ 8.84 (dd, J=4.7, 1.6 Hz, 1H), 8.39 (dd, J=8.3, 1.6 Hz, 1H), 7.64-7.59 (m, 2H), 7.44 (dd, J=8.3, 4.7 Hz, 1H), 7.24 (d, J=8.4 Hz, 2H), 3.68 (s, 3H), 2.99 (t, J=7.7 Hz, 2H), 2.65 (t, J=7.7 Hz, 2H); $^{13}$C NMR (CDCl$_3$) δ 173.0, 153.5, 146.8, 143.0, 137.6, 132.8, 132.5, 128.6, 122.5, 119.3, 98.0, 85.0, 51.7, 35.2, 30.9; ESI-MS m/z 333.1 (M+Na$^+$).

Example A34

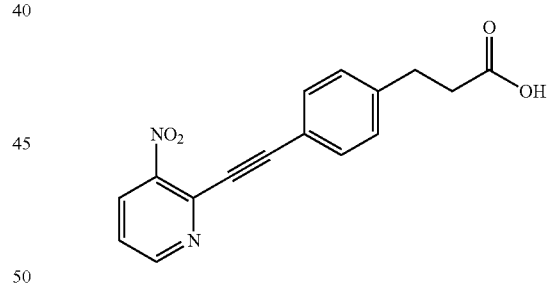

3-(4-((3-Nitropyridin-2-yl)ethynyl)phenyl)propanoic acid. The title compound was prepared from methyl 3-(4-((3-nitropyridin-2-yl)ethynyl)phenyl)propanoate (73 mg, 0.24 mmol) according to the general procedure II to give 67 mg (95%) of the pure title compound as a dark orange solid: R$_f$=0.34 ([EtOAc with 1.25% AcOH]:PE, 1:1); $^1$H NMR (Acetone-d$_6$) δ 8.77 (dd, J=4.6, 1.2 Hz, 1H), 8.39 (dd, J=8.4, 1.2 Hz, 1H), 7.56 (dd, J=8.4, 4.7 Hz, 1H), 7.46 (d, J=8.1 Hz, 2H), 7.28 (d, J=8.0 Hz, 2H), 2.86 (t, J=7.6 Hz, 2H), 2.54 (t, J=7.6 Hz, 2H); $^{13}$C NMR (Acetone-d$_6$) δ 173.7, 154.6, 148.3, 144.8, 137.4, 133.4, 133.1, 129.9, 124.4, 120.1, 97.0, 85.7, 35.4, 31.5; ESI-MS calcd for C$_{16}$H$_{12}$N$_2$O$_4$ (M+Na$^+$) 319.0690. found 319.0677.

Intermediate-6

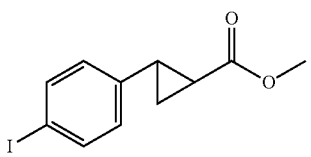

Methyl 2-(4-iodophenyl)cyclopropanecarboxylate. Methanol (16 mL) under argon at 0° C. was added AcCl (1.3 mL, 18.3 mmol). The reaction was stirred for 10 min before slow addition of 2-phenylcyclopropanecarboxylic acid (1.65 g, 5.74 mmol). The reaction was stirred for additional 3 hours at room temperature. before the mixture was concentrated under vacuum, re-dissolved in MeOH and concentrated to give 1.68 g (97%) of a pure white solid: $R_t$: 13.24 min (HPLC method I).

Intermediate-7

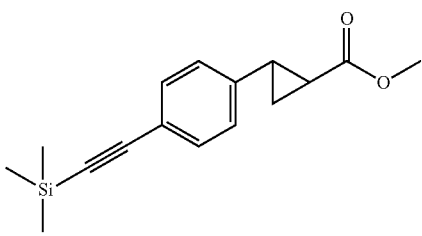

Methyl 2-(4-((trimethylsilyl)ethynyl)phenyl)cyclopropanecarboxylate. The title compound was prepared from and according to the general procedure A dry Schlenk flask was charged with methyl 2-(4-iodophenyl)cyclopropanecarboxylate (1.66 g, 5.49 mmol), $Na_2[PdCl_4]$ (18 mg, 0.06 mmol), 2-(di-tert-butylphosphino)-1-phenylindole (37 mg, 0.11 mmol), CuI (21 mg, 0.11 mmol), and tetramethylethylenediamine (10 mL). The mixture was evacuated and backfilled with Ar (3×), and heated to 70° C. before addition of trimethylsilylacetylene (1.4 mL, 10.8 mmol) through the septum and the temperature was elevated to 80° C. After consumption of the starting material indicated by HPLC, the reaction mixture was cooled to room temperature, quenched with water and extracted with EtOAc (3×). The combined extracts were washed with brine, dried over $MgSO_4$ and concentrated under vacuum and a fraction of the residue was purified by flash chromatography to give 580 mg (40%) after purification by flash chromatography ($SiO_2$, EtOAc:PE, 1:8): $R_t$: 14.56 min (HPLC method I).

Intermediate-8

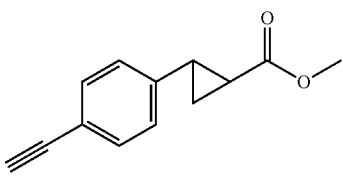

Methyl 2-(4-ethynylphenyl)cyclopropanecarboxylate. Methyl 3-(4-((trimethylsilyl)ethynyl)phenyl)cyclopropanecarboxylate (580 mg, 2.19 mmol) and potassium carbonate (614 mg, 4.44 mmol) was dissolved in MeOH (22 mL) and stirred vigorously for 4 hours at room temperature. The reaction was added water and extracted with EtOAc. The organic phases were combined, washed with brine, dried over $MgSO_4$ before concentrated under vacuum to give 419 mg (95%) of a pale yellow solid: $R_f$: 0.60 (EtOAc:hexanes, 1:1).

Example E35

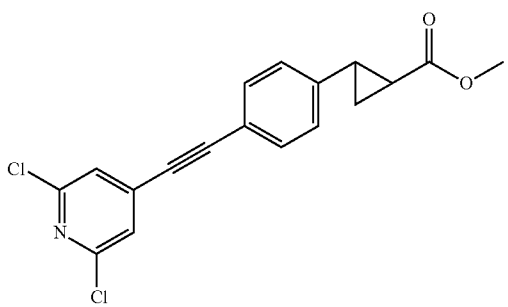 [SMILES: COC(=O)C1CC1c1ccc(C#Cc2cc(Cl)nc(Cl)c2)cc1]

Methyl 2-(4-((2,6-dichloropyridin-4-yl)ethynyl)phenyl)cyclopropanecarboxylate. The title compound was prepared from methyl 2-(4-ethynylphenyl)cyclopropanecarboxylate (80 mg, 0.40 mmol) and 2,6-dichloro-4-iodopyridine (121 mg, 0.44 mmol) according to the general procedure IF to give 19 mg (23%) of a white solid after purification by flash chromatography ($SiO_2$, EtOAc:PE, 1:10): $R_f$=0.36 (EtOAc: PE, 1:4); $^1$H NMR ($CDCl_3$) δ 7.45 (d, J=8.2 Hz, 2H), 7.34 (s, 2H), 7.11 (d, J=8.2 Hz, 2H), 3.73 (s, 3H), 2.61-2.48 (m, 1H), 2.02-1.90 (m, 1H), 1.67 (dt, J=10.0, 5.1 Hz, 1H), 1.35 (ddd, J=8.4, 6.4, 4.8 Hz, 1H); $^{13}$C NMR ($CDCl_3$) δ 173.4, 150.7, 142.5, 136.5, 132.2, 126.4, 124.4, 119.2, 96.7, 84.7, 52.1, 26.1, 24.4, 17.3; ESI-MS m/z 368.1 (M+Na$^+$).

Example A35

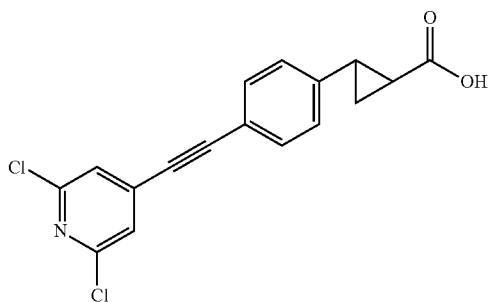 [SMILES: O=C(O)C1CC1c1ccc(C#Cc2cc(Cl)nc(Cl)c2)cc1]

2-(4-((2,6-Dichloropyridin-4-yl)ethynyl)phenyl)cyclopropanecarboxylic acid. The title compound was prepared from methyl 2-(4-((2,6-dichloropyridin-4-yl)ethynyl)phenyl)cyclopropanecarboxylate (16 mg, 0.05 mmol) according to the general procedure II to give 14 mg (88%) of the pure title compound as a white solid: $R_f$=0.37 ([EtOAc with 1.25% AcOH]:PE, 1:1); $^1$H NMR (Acetone-$d_6$) δ $^1$H NMR (Acetone-$d_6$) δ 7.47-7.40 (m, 4H), 7.17 (d, J=8.3 Hz, 2H), 2.43-2.33 (m, 1H), 1.84 (ddd, J=9.3, 5.2, 4.2 Hz, 1H), 1.44 (dt, J=9.6, 4.9 Hz, 1H), 1.35-1.29 (m, 1H); $^{13}$C NMR (Acetone-$d_6$) δ 173.9, 151.2, 144.2, 137.7, 133.1, 127.4, 125.4, 119.9, 97.5, 85.3, 26.5, 25.0, 17.7; ESI-MS calcd for $C_{18}H_{13}Cl_2NO_2$ (M+Na$^+$) 354.0060. found 354.0055.

Example E36

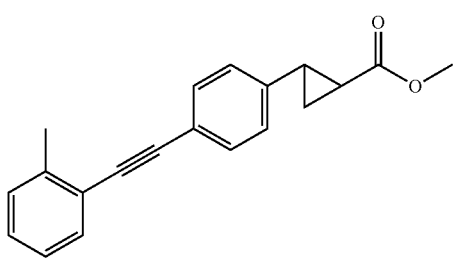 [SMILES: COC(=O)C1CC1c1ccc(C#Cc2ccccc2C)cc1]

Methyl 2-(4-(o-tolylethynyl)phenyl)cyclopropanecarboxylate. The title compound was prepared from methyl 2-(4-ethynylphenyl)cyclopropanecarboxylate (80 mg, 0.40 mmol) and 1-iodo-2-methylbenzene (113 mg, 0.56 mmol) according to the general procedure IF to give 45 mg (39%) of a pale yellow solid after purification by flash chromatography (SiO$_2$, EtOAc:PE, 1:10): $R_f$=0.41 (EtOAc:PE, 1:4); $^1$H NMR (CDCl$_3$) δ 7.52-7.41 (m, 3H), 7.25-7.20 (m, 2H), 7.20-7.12 (m, 1H), 7.07 (d, J=8.2 Hz, 2H), 3.72 (s, 3H), 2.57-2.51 (m, 1H), 2.50 (s, 3H), 1.92 (ddd, J=8.5, 5.3, 4.2 Hz, 1H), 1.63 (dt, J=9.2, 5.0 Hz, 1H), 1.33 (ddd, J=8.4, 6.5, 4.7 Hz, 1H); $^{13}$C NMR (CDCl$_3$) δ 173.6, 140.3, 140.2, 131.8, 131.6, 129.5, 128.3, 126.2, 125.6, 123.0, 121.7, 93.1, 88.5, 52.0, 26.2, 24.2, 20.8, 17.2; ESI-MS m/z 313.1 (M+Na$^+$).

Example A36

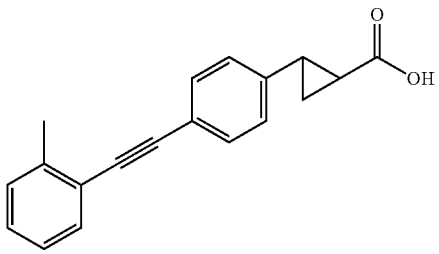 [SMILES: Cc1ccccc1C#Cc1ccc(C2CC2C(=O)O)cc1]

2-(4-(o-Tolylethynyl)phenyl)cyclopropanecarboxylic acid. The title compound was prepared from methyl 2-(4-(o-tolylethynyl)phenyl)cyclopropanecarboxylate (42 mg, 0.14 mmol) according to the general procedure II to give 39 mg (98%) of the pure title compound as a pale yellow solid: $R_f$=0.37 ([EtOAc with 1.25% AcOH]:PE, 1:1); $^1$H NMR (Acetone-d$_6$) δ 7.35-7.29 (m, 3H), 7.15-7.01 (m, 5H), 2.39-2.30 (m, 4H), 1.82-1.74 (m, 1H), 1.39 (dt, J=9.6, 4.9 Hz, 1H), 1.25 (ddd, J=8.4, 6.4, 4.5 Hz, 1H); $^{13}$C NMR (Acetone-d$_6$) δ 174.0, 142.1, 140.7, 132.5, 132.4, 130.4, 129.4, 127.2, 126.7, 123.8, 122.2, 94.1, 88.9, 67.6, 26.5, 24.8, 20.8, 17.5; ESI-MS calcd for $C_{19}H_{16}O_2$ (M+Na$^+$) 299.1043. found 299.1042.

Example E37

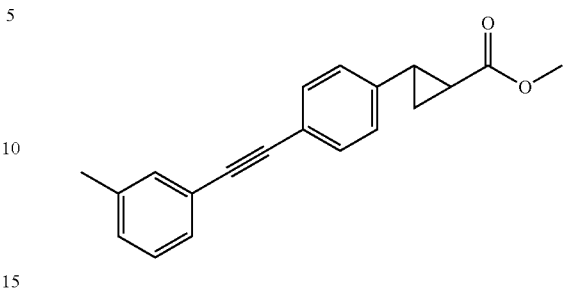

Methyl 2-(4-(m-tolylethynyl)phenyl)cyclopropanecarboxylate. The title compound was prepared from methyl 2-(4-ethynylphenyl)cyclopropanecarboxylate (80 mg, 0.40 mmol) and 1-iodo-3-methylbenzene (60 μL, 0.47 mmol) according to the general procedure IF to give 42 mg (36%) of a pale yellow solid after purification by flash chromatography (SiO$_2$, EtOAc:PE, 1:9): $R_f$=0.43 (EtOAc:PE, 1:4); $^1$H NMR (CDCl$_3$) δ 7.43 (d, J=8.3 Hz, 2H), 7.37-7.30 (m, 2H), 7.23 (t, J=7.6 Hz, 1H), 7.14 (d, J=7.6 Hz, 1H), 7.06 (d, J=8.2 Hz, 2H), 3.72 (s, 3H), 2.61-2.45 (m, 1H), 2.35 (s, 3H), 1.92 (ddd, J=8.5, 5.3, 4.3 Hz, 1H), 1.63 (dt, J=9.9, 5.0 Hz, 1H), 1.33 (ddd, J=8.4, 6.5, 4.7 Hz, 1H); $^{13}$C NMR (CDCl$_3$) δ 173.6, 140.3, 138.0, 132.2, 131.7, 129.1, 128.6, 128.2, 126.2, 123.1, 121.5, 89.7, 88.8, 52.0, 26.2, 24.2, 21.2, 17.2; ESI-MS m/z 313.1 (M+Na$^+$).

Example A37

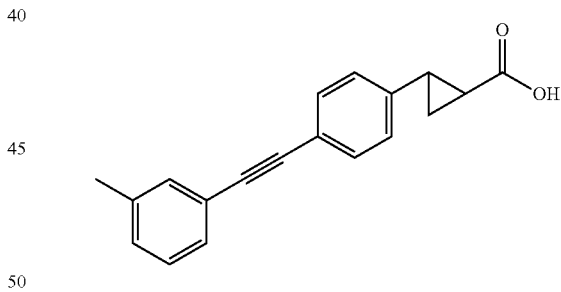

2-(4-(m-Tolylethynyl)phenyl)cyclopropanecarboxylic acid. The title compound was prepared from methyl 2-(4-(m-tolylethynyl)phenyl)cyclopropanecarboxylate (37 mg, 0.13 mmol) according to the general procedure II to give 35 mg (99%) of the pure title compound as a white solid: $R_f$=0.33 ([EtOAc with 1.25% AcOH]:PE, 1:1); $^1$H NMR (Acetone-d$_6$) δ 7.33 (d, J=8.2 Hz, 2H), 7.25-7.05 (m, 6H), 2.40-2.32 (m, 1H), 2.21 (s, 3H), 1.81 (dt, J=9.2, 4.7 Hz, 1H), 1.42 (dt, J=9.4, 4.9 Hz, 1H), 1.28 (ddd, J=8.3, 6.4, 4.6 Hz, 1H); $^{13}$C NMR (Acetone-d$_6$) δ 174.0, 142.1, 139.1, 132.8, 132.4, 130.1, 129.4, 127.2, 124.0, 122.0, 90.2, 89.6, 26.5, 24.8, 21.2, 17.5; ESI-MS calcd for $O_{19}H_{16}O_2$ (M+Na$^+$) 299.1043. found 299.1057.

Example E38

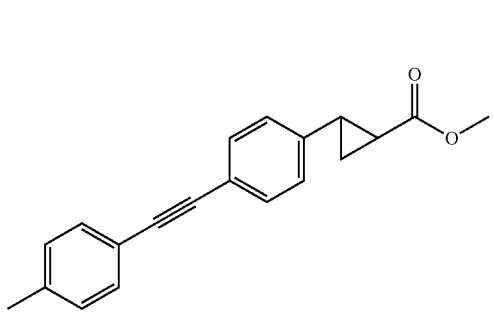

Methyl 2-(4-(p-tolylethynyl)phenyl)cyclopropanecarboxylate. The title compound was prepared from methyl 2-(4-ethynylphenyl)cyclopropanecarboxylate (80 mg, 0.40 mmol) and 1-iodo-3-methylbenzene (97 mg, 0.44 mmol) according to the general procedure IF to give 57 mg (49%) of a white after purification by flash chromatography (SiO$_2$, EtOAc:PE, 1:9): R$_f$=0.43 (EtOAc:PE, 1:4); $^1$H NMR (CDCl$_3$) δ 7.46-7.38 (m, 4H), 7.14 (d, J=7.9 Hz, 2H), 7.06 (d, J=8.2 Hz, 2H), 3.72 (s, 3H), 2.59-2.47 (m, 1H), 2.36 (s, 3H), 1.92 (ddd, J=8.5, 5.3, 4.2 Hz, 1H), 1.63 (dt, J=9.9, 5.0 Hz, 1H), 1.33 (ddd, J=8.4, 6.5, 4.7 Hz, 1H); $^{13}$C NMR (CDCl$_3$) δ 173.6, 140.2, 138.4, 131.6, 131.5, 129.1, 126.1, 121.6, 120.2, 89.6, 88.5, 52.0, 26.2, 24.2, 21.5, 17.2; ESI-MS m/z 313.1 (M+Na$^+$).

Example A38

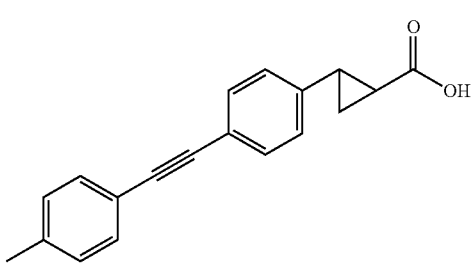 [SMILES: Cc1ccc(C#Cc2ccc(C3CC3C(=O)O)cc2)cc1]

2-(4-(p-Tolylethynyl)phenyl)cyclopropanecarboxylic acid. The title compound was prepared from methyl 2-(4-(p-tolylethynyl)phenyl)cyclopropanecarboxylate (53 mg, 0.18 mmol) according to the general procedure II to give 49 mg (97%) of the pure title compound as a white solid: R$_f$=0.33 ([EtOAc with 1.25% AcOH]:PE, 1:1); $^1$H NMR (DMSO-d$_6$) δ 12.35 (s, 1H), 7.43 (dd, J=8.2, 3.1 Hz, 4H), 7.29-7.18 (m, 4H), 2.48-2.39 (m, 1H), 2.34 (s, 3H), 1.90-1.82 (m, 1H), 1.47 (dt, J=9.4, 4.8 Hz, 1H), 1.39-1.35 (m, 1H); $^{13}$C NMR (DMSO-d$_6$) δ 173.6, 141.1, 138.4, 131.2, 131.1, 129.3, 126.2, 120.1, 119.3, 89.3, 88.6, 26.2, 25.1, 24.4, 20.9, 16.8; ESI-MS calcd for O$_{19}$H$_{16}$O$_2$ (M+Na$^+$) 299.1043. found 299.1056.

Example E39

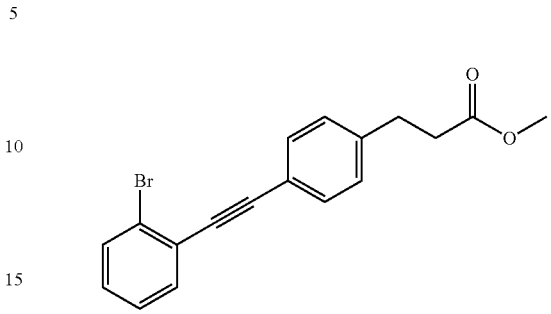

Methyl 3-(4-((2-bromophenyl)ethynyl)phenyl)propanoate. The title compound was prepared from methyl 3-(4-ethynylphenyl)propanoate (300 mg, 1.59 mmol) and 1-bromo-2-iodobenzene (0.3 mL, 2.34 mmol) according to the general procedure ID to give 340 mg (62%) of an yellow oily product after purification by flash chromatography (SiO$_2$, EtOAc:PE, 1:5). R$_f$=0.27 (EtOAc:PE, 1:5); $^1$H NMR (CDCl$_3$) δ 7.61 (dd, J=8.0, 1.1 Hz, 1H), 7.54 (dd, J=7.7, 1.7 Hz, 1H), 7.52-7.48 (m, 2H), 7.28 (td, J=7.6, 1.2 Hz, 1H), 7.22-7.14 (m, 3H), 3.67 (s, 3H), 2.97 (t, J=7.7 Hz, 2H), 2.64 (t, J=7.7 Hz, 2H); $^{13}$C NMR (CDCl$_3$) δ 173.1, 141.3, 133.2, 132.4, 131.8, 129.3, 128.4, 127.0, 125.6, 125.5, 120.9, 93.9, 87.8, 51.7, 35.4, 30.9; ESI-MS m/z 365.0 (M+Na$^+$).

Example A39

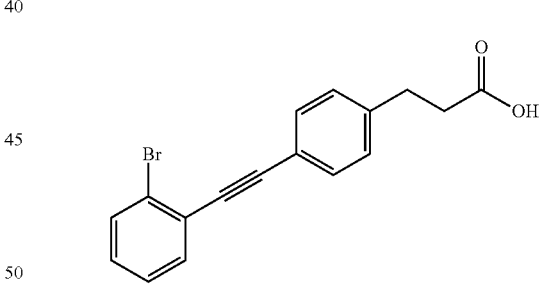

3-(4-((2-Bromophenyl)ethynyl)phenyl)propanoic acid. The title compound was prepared from methyl 3-(4-((2-bromophenyl)ethynyl)phenyl)propanoate (71 mg, 0.21 mmol) according to the general procedure II to give 64 mg (92%) of the pure title compound as a white solid: R$_f$=0.20 ([EtOAc with 1.25% AcOH]:PE, 1:2); $^1$H NMR (Acetone-d$_6$) δ 7.53 (dd, J=8.1, 1.1 Hz, 1H), 7.45 (dd, J=7.7, 1.7 Hz, 1H), 7.37-7.32 (m, 2H), 7.24 (td, J=7.6, 1.2 Hz, 1H), 7.20-7.11 (m, 3H), 2.78 (t, J=7.6 Hz, 2H), 2.48 (t, J=7.6 Hz, 2H); $^{13}$C NMR (Acetone-d$_6$) δ 173.7, 143.4, 134.2, 133.4, 132.4, 130.8, 129.7, 128.5, 126.2, 125.8, 121.3, 94.8, 88.2, 35.5, 31.4; ESI-MS calcd for C$_{17}$H$_{13}$BrO$_2$ (M+Na$^+$) 350.9992. found 350.9976.

Example E40

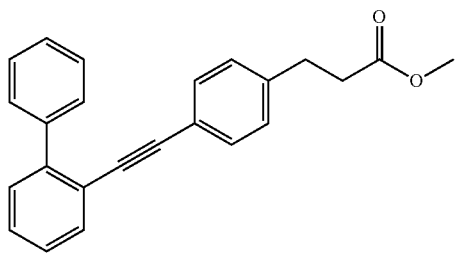 [SMILES: COC(=O)CCc1ccc(C#Cc2ccccc2-c2ccccc2)cc1]

Methyl 3-(4-(biphenyl-2-ylethynyl)phenyl)propanoate. The title compound was prepared from methyl 3-(4-((2-bromophenyl)ethynyl)phenyl)propanoate (67 mg, 0.20 mmol) and acid (36 mg, 0.29 mmol) according to the general procedure III to give 50 mg (74%) of an yellow solid after purification by flash chromatography (SiO$_2$, EtOAc:PE, 1:8): R$_f$=0.40 (EtOAc:PE, 1:4); $^1$H NMR (CDCl$_3$) δ 7.68-7.60 (m, 3H), 7.48-7.35 (m, 5H), 7.35-7.29 (m, 1H), 7.27-7.22 (m, 2H), 7.14-7.08 (m, J=8.3 Hz, 2H), 3.65 (s, 3H), 2.92 (t, J=7.7 Hz, 2H), 2.60 (t, J=7.8 Hz, 2H); $^{13}$C NMR (CDCl$_3$) δ 173.1, 143.9, 140.7, 140.6, 132.8, 131.5, 129.5, 129.4, 128.4, 128.3, 127.9, 127.4, 127.0, 121.7, 121.4, 92.1, 89.1, 51.7, 35.4, 30.8; ESI-MS m/z 363.2 (M+Na$^+$).

Example A40

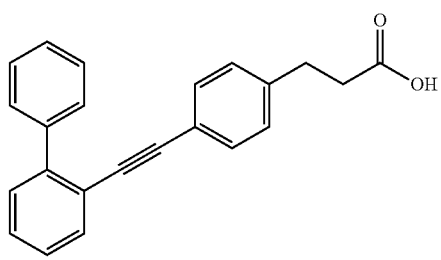 [SMILES: O=C(O)CCc1ccc(C#Cc2ccccc2-c2ccccc2)cc1]

3-(4-(Biphenyl-2-ylethynyl)phenyl)propanoic acid. The title compound was prepared from methyl 3-(4-(biphenyl-2-ylethynyl)phenyl)propanoate (41 mg, 0.12 mmol) according to the general procedure II to give 37 mg (94%) of the pure title compound as a yellow solid: R$_f$=0.35 ([EtOAc with 1.25% AcOH]:PE, 1:1); NMR (Acetone-d$_6$) δ 7.58-7.49 (m, 3H), 7.41-7.23 (m, 6H), 7.17-7.09 (m, 4H), 2.78 (t, J=7.6 Hz, 2H), 2.48 (t, J=7.6 Hz, 2H); $^{13}$C NMR (Acetone-d$_6$) δ 173.7, 144.6, 142.7, 141.4, 133.6, 132.1, 130.4, 130.1, 129.6, 129.5, 128.9, 128.4, 128.2, 122.3, 121.9, 92.9, 89.6, 35.5, 31.4; ESI-MS calcd for C$_{23}$H$_{18}$O$_2$ (M+Na$^+$) 349.1200. found 349.1199.

Example E41

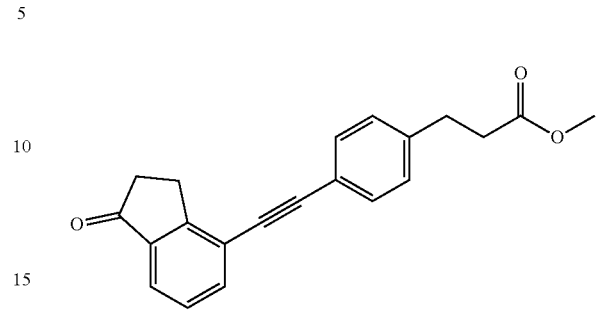

Methyl 3-(4-((1-oxo-2,3-dihydro-1H-inden-4-yl)ethynyl)phenyl)propanoate. The title compound was prepared from methyl 3-(4-ethynylphenyl)propanoate (94 mg, 0.50 mmol) and 4-bromo-2,3-dihydro-1H-inden-1-one (116 mg, 0.55 mmol) according to the general procedure IF to give 110 mg (69%) of an yellow solid after purification by flash chromatography (SiO$_2$, EtOAc:PE, 1:5): R$_f$=0.34 (EtOAc:PE, 1:2); $^1$H NMR (CDCl$_3$) δ 7.76-7.68 (m, 2H), 7.55-7.43 (m, 2H), 7.38 (t, J=7.6 Hz, 1H), 7.22 (d, J=8.3 Hz, 2H), 3.68 (s, 1H), 3.29-3.21 (m, 2H), 2.98 (t, J=7.7 Hz, 3H), 2.77-2.71 (m, 2H), 2.65 (t, J=7.7 Hz, 2H); $^{13}$C NMR (CDCl$_3$) δ 206.6, 173.0, 157.1, 141.5, 137.3, 136.8, 131.8 128.5, 127.5, 123.3, 122.3, 120.7, 94.8, 85.3, 51.7, 36.1, 35.3, 30.8, 25.5; ESI-MS m/z 341.1 (M+Na$^+$).

Example A41

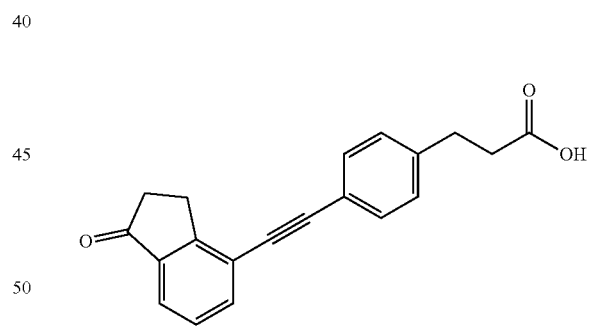

3-(4-((1-oxo-2,3-dihydro-1H-inden-4-yl)ethynyl)phenyl)propanoic acid. The title compound was prepared from methyl 3-(4-((1-oxo-2,3-dihydro-1H-inden-4-yl)ethynyl)phenyl)propanoate (50 mg, 0.16 mmol) according to the general procedure II to give 40 mg (85%) of the pure title compound as a pale yellow solid: R$_f$=0.14 ([EtOAc with 1.25% AcOH]:PE, 1:2); $^1$H NMR (Acetone-d$_6$) δ 7.64 (dd, J=7.5, 1.1 Hz, 1H), 7.56-7.50 (m, 1H), 7.43-7.37 (m, 2H), 7.34 (t, J=7.6 Hz, 1H), 7.26-7.20 (m, 2H), 3.18-3.09 (m, 2H), 2.83 (t, J=7.6 Hz, 2H), 2.62-2.48 (m, 4H); $^{13}$C NMR (Acetone-d$_6$) δ 173.7, 157.9, 143.4, 138.4, 137.3, 132.5, 129.7, 128.5, 123.7, 123.1, 121.4, 95.6, 86.0, 36.5, 35.5, 31.4, 26.2.

Example E42

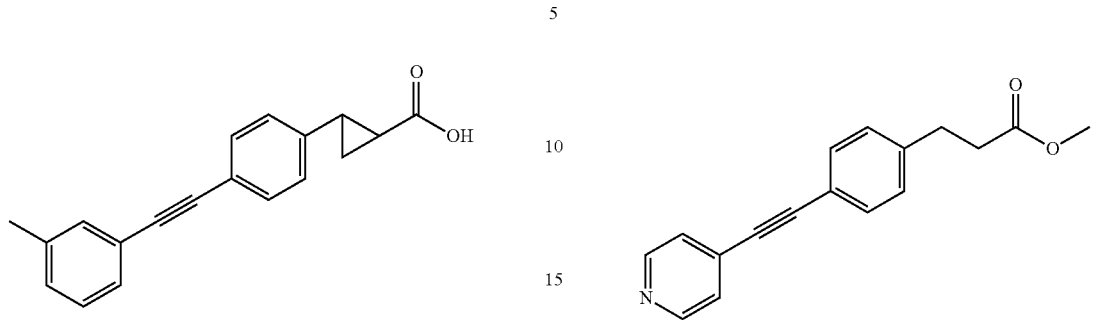

Methyl 3-(4-((3-(isocyanomethyl)phenyl)ethynyl)phenyl)propanoate. The title compound was prepared from methyl 3-(4-ethynylphenyl)propanoate (95 mg, 0.50 mmol) and 1-bromo-3-(isocyanomethyl)benzene (117 mg, 0.60 mmol) according to the general procedure IC to give 109 mg (71%) of a pale yellow oily product after purification by flash chromatography (SiO$_2$, EtOAc:PE, 1:5). R$_f$=0.27 (EtOAc:PE, 1:2); $^1$H NMR (CDCl$_3$) δ 7.51-7.44 (m, 4H), 7.36 (t, J=7.7 Hz, 1H), 7.31-7.27 (m, 1H), 7.19 (d, J=8.3 Hz, 2H), 3.73 (s, 2H), 3.67 (s, 3H), 2.97 (t, J=7.7 Hz, 2H), 2.64 (t, J=7.7 Hz, 2H); $^{13}$C NMR (CDCl$_3$) δ 173.1, 141.2, 131.8, 131.2, 131.0, 130.2, 129.2, 128.4, 127.6, 124.5, 120.8, 117.5, 90.3, 88.1, 51.7, 35.4, 30.8, 23.4; ESI-MS m/z 326.1 (M+Na$^+$).

Example A42

3-(4-((3-(Isocyanomethyl)phenyl)ethynyl)phenyl)propanoic acid. The title compound was prepared from methyl 3-(4-((3-(isocyanomethyl)phenyl)ethynyl)phenyl)propanoate (90 mg, 0.30 mmol) according to the general procedure II to give 82 mg (95%) of the pure title compound as a white solid: R$_f$=0.13 ([EtOAc with 1.25% AcOH]:PE, 1:2); $^1$H NMR (Acetone-d$_6$) δ 7.45-7.42 (m, 1H), 7.40-7.27 (m, 5H), 7.22-7.17 (m, 2H), 3.87 (s, 2H), 2.82 (t, J=7.6 Hz, 2H), 2.52 (t, J=7.6 Hz, 2H); $^{13}$C NMR (Acetone-d$_6$) δ 173.7, 143.1, 133.0, 132.5, 131.8, 131.5, 130.2, 129.6, 129.0, 124.9, 121.5, 118.9, 90.8, 88.9, 35.5, 31.4, 23.2; ESI-MS calcd for O$_{16}$H$_{16}$NO$_2$ (M+Na$^+$) 312.0996. found 312.0998.

Example E43

Methyl 3-(4-(pyridin-4-ylethynyl)phenyl)propanoate. The title compound was prepared from methyl 3-(4-ethynylphenyl)propanoate (94 mg, 0.50 mmol) and 4-bromopyridine hydrochloride (108 mg, 0.55 mmol) according to the general procedure IC to give 72 mg (54%) of a white solid after purification by flash chromatography (SiO$_2$, EtOAc:PE, 1:5). R$_f$=0.26 (EtOAc:PE, 1:1); $^1$H NMR (CDCl$_3$) δ 8.52 (dd, J=4.5, 1.5 Hz, 2H), 7.45-7.39 (m, 2H), 7.29 (dd, J=4.5, 1.6 Hz, 2H), 7.14 (d, J=8.3 Hz, 2H), 3.60 (s, 3H), 2.90 (t, J=7.7 Hz, 2H), 2.57 (t, J=7.7 Hz, 2H); $^{13}$C NMR (CDCl$_3$) δ 172.0, 148.8, 141.0, 131.0, 130.5, 127.5, 124.5, 119.0, 92.9, 85.5, 50.7, 34.3, 29.8; ESI-MS m/z 288.1 (M+Na$^+$).

Example A43

3-(4-(Pyridin-4-ylethynyl)phenyl)propanoic acid. The title compound was prepared from methyl 3-(4-(pyridin-4-ylethynyl)phenyl)propanoate (63 mg, 0.24 mmol) according to the general procedure II to give 18 mg (30%) of the pure title compound as a white solid: R$_f$=0.04 (EtOAc:PE, 1:1); $^1$H NMR (DMSO-d$_6$) δ 12.15 (s, 1H), 8.62 (dd, J=4.6, 1.3 Hz, 2H), 7.58-7.46 (m, 4H), 7.33 (d, J=8.1 Hz, 2H), 2.87 (t, J=7.5 Hz, 2H), 2.57 (t, J=7.6 Hz, 2H); $^{13}$C NMR (DMSO-d$_6$) δ 173.6 149.9, 142.9, 131.7, 130.3, 128.8, 125.3, 118.8, 93.7, 86.3, 34.7, 30.2; ESI-MS calcd for C$_{16}$H$_{13}$NO$_2$ (M+H$^+$) 252.1019. found 252.1016.

Example E44

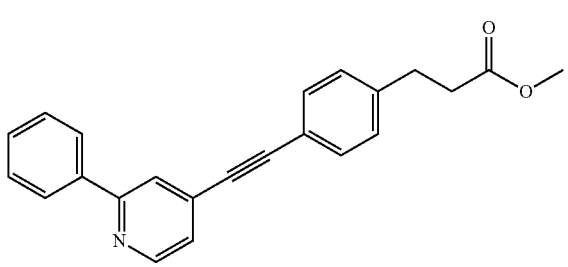 [SMILES: COC(=O)CCc1ccc(C#Cc2ccnc(-c3ccccc3)c2)cc1]

Methyl 3-(4-((2-phenylpyridin-4-yl)ethynyl)phenyl)propanoate. The title compound was prepared from methyl 3-(4-ethynylphenyl)propanoate (80 mg, 0.27 mmol) and phenylboronic acid (49 mg, 0.40 mmol) according to the general procedure III to give 56 mg (62%) of a pale yellow solid after purification by flash chromatography (SiO$_2$, EtOAc:PE, 1:5): R$_f$=0.16 (EtOAc:PE, 1:4); $^1$H NMR (CDCl$_3$) δ 8.59 (dd, J=5.1, 0.8 Hz, 1H), 7.97-7.90 (m, 2H), 7.74 (dd, J=5.8, 4.7 Hz, 1H), 7.45-7.33 (m, 5H), 7.27-7.21 (m, 2H), 7.15 (d, J=8.3 Hz, 2H), 3.60 (s, 3H), 2.91 (t, J=7.7 Hz, 2H), 2.58 (dd, J=10.2, 5.2 Hz, 2H); $^{13}$C NMR (CDCl$_3$) δ 172.0, 156.6, 148.6, 141.0, 137.8, 131.2, 131.1, 128.2, 127.8, 127.5, 125.9, 122.7, 121.5, 119.1, 92.7, 85.8, 50.7, 34.6, 29.8.

Example E45

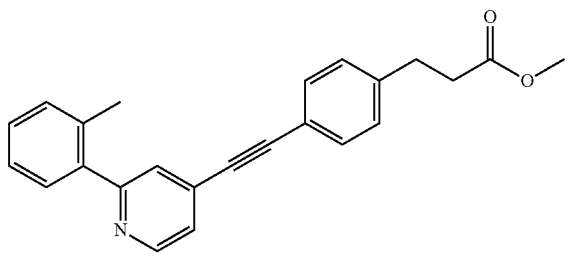

Methyl 3-(4-((2-o-tolylpyridin-4-yl)ethynyl)phenyl)propanoate. The title compound was prepared from methyl 3-(4-ethynylphenyl)propanoate (80 mg, 0.27 mmol) and o-tolyl-boronic acid (56 mg, 0.41 mmol) according to the general procedure III to give 30 mg (32%) of a pale oily compound after purification by flash chromatography (SiO$_2$, EtOAc:PE, 1:5): R$_f$=0.17 (EtOAc:PE, 1:5); $^1$H NMR (CDCl$_3$) δ 8.14 (d, J=5.2 Hz, 1H), 7.28-7.15 (m, 3H), 7.12-6.98 (m, 5H), 6.89-6.82 (m, 1H), 6.44 (s, 1H), 3.66 (s, 3H), 2.94 (t, J=7.8 Hz, 2H), 2.62 (t, J=7.8 Hz, 2H), 2.08 (s, 3H); $^{13}$C NMR (CDCl$_3$) δ 173.1, 151.6, 149.6, 149.3, 148.8, 148.4, 142.7, 140.9, 136.8, 136.1, 132.2, 130.7, 129.8, 129.7, 128.6, 128.5, 128.2, 125.8, 124.2, 122.5, 51.6, 35.5, 30.7, 20.4.

Example A44

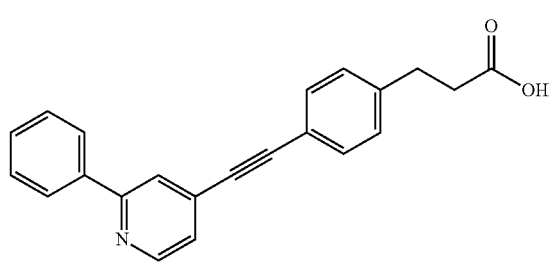 [SMILES: O=C(O)CCc1ccc(C#Cc2ccnc(-c3ccccc3)c2)cc1]

3-(4-((2-Phenylpyridin-4-yl)ethynyl)phenyl)propanoic acid. The title compound was prepared from methyl 3-(4-((2-phenylpyridin-4-yl)ethynyl)phenyl)propanoate (35 mg, 0.10 mmol) according to the general procedure II to give 33 mg (99%) of the pure title compound as a white solid: R$_f$=0.53 (EtOAc with 1.25% AcOH); $^1$H NMR (DMSO-d$_6$) δ 12.17 (s, 1H), 8.71 (d, J=5.0 Hz, 1H), 8.15 (d, J=7.3 Hz, 2H), 8.10 (s, 1H), 7.58-7.45 (m, 6H), 7.35 (d, J=8.0 Hz, 2H), 2.88 (t, J=7.4 Hz, 2H), 2.58 (t, J=7.5 Hz, 2H); $^{13}$C NMR (DMSO-d$_6$) δ 173.6, 156.4, 149.9, 142.9, 137.9, 131.7, 131.4, 129.4, 128.8, 128.8, 126.6, 123.9, 121.7, 118.9, 93.7, 86.7, 34.7, 30.2.

Example A45

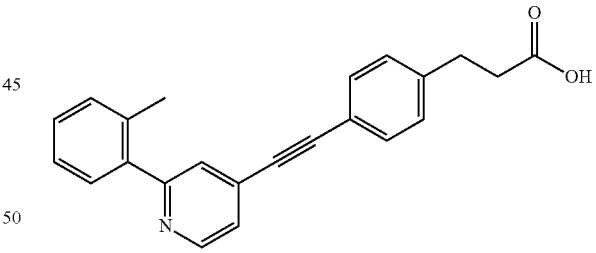

3-(4-((2-o-Tolylpyridin-4-yl)ethynyl)phenyl)propanoic acid. The title compound was prepared from methyl 3-(4-((2-o-tolylpyridin-4-yl)ethynyl)phenyl)propanoate (15 mg, 0.04 mmol) according to the general procedure II to give 14 mg (94%) of the pure title compound as a pale yellow solid: R$_f$=0.53 (EtOAc with 1.25% AcOH); $^1$H NMR (Methanol-d$_4$) δ 7.99 (d, J=5.3 Hz, 1H), 7.17-7.04 (m, 5H), 7.01-6.99 (m, 1H), 6.95-6.86 (m, 3H), 6.43 (s, 1H), 2.81 (t, J=7.6 Hz, 2H), 2.49 (t, J=7.6 Hz, 2H), 1.97 (s, 3H); $^{13}$C NMR (Methanol-d$_4$) δ 176.6, 152.3, 151.0, 150.8, 150.1, 144.1, 142.9, 138.3, 137.3, 131.7, 130.9, 130.9, 129.8, 129.3, 126.9, 126.8, 125.6, 124.2, 36.6, 31.8, 20.6.

Example A46

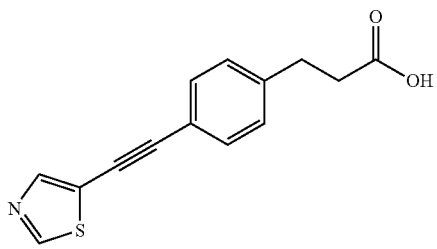 [SMILES: O=C(O)CCc1ccc(C#Cc2cncs2)cc1]

3-(4-(Thiazol-5-ylethynyl)phenyl)propanoic acid. The title compound was prepared from methyl 3-(4-ethynylphenyl)propanoate (95 mg, 0.50 mmol) and 5-bromothiazole (50 μL, 0.56 mmol) according to the general procedure IF. After concentration the residue was hydrolyzed according to the general procedure II to give 28 mg (21%) of a white solid after purification by flash chromatography (SiO$_2$, EtOAc [with 1.25% AcOH]:PE, 1:2): R$_f$=0.12 ([EtOAc with 1.25% AcOH]:PE, 1:2); $^1$H NMR (DMSO-d$_6$) δ 12.14 (s, 1H), 9.16 (d, J=0.6 Hz, 1H), 8.20 (d, J=0.6 Hz, 1H), 7.49 (d, J=8.2 Hz, 3H), 7.31 (d, J=8.3 Hz, 3H), 2.86 (t, J=7.5 Hz, 3H), 2.56 (t, J=7.6 Hz, 3H); $^{13}$C NMR (DMSO-d$_6$) δ 173.5, 155.7, 147.2, 142.6, 131.2, 128.7, 118.8, 118.0, 96.0, 78.4, 34.6, 30.1; ESI-MS calcd for C$_{14}$H$_{11}$NO$_2$S (M+Na$^+$) 280.0403. found 280.0400.

Example E47

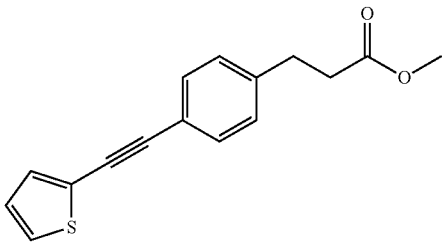 [SMILES: COC(=O)CCc1ccc(C#Cc2cccs2)cc1]

Methyl 3-(4-(thiophen-2-ylethynyl)phenyl)propanoate. The title compound was prepared from methyl 3-(4-ethynylphenyl)propanoate (95 mg, 0.50 mmol) and 2-bromothiophene (60 μL, 0.62 mmol) according to the general procedure IF to give 97 mg (71%) of a white solid after purification by flash chromatography (SiO$_2$, EtOAc:PE, 1:5): R$_f$=0.44 (EtOAc:PE, 1:2); $^1$H NMR (CDCl$_3$) δ 7.50-7.39 (m, 2H), 7.31-7.23 (m, 2H), 7.18 (d, J=8.4 Hz, 2H), 7.00 (dd, J=5.1, 3.7 Hz, 1H), 3.67 (s, 3H), 2.96 (t, J=7.7 Hz, 2H), 2.63 (t, J=7.7 Hz, 2H); $^{13}$C NMR (CDCl$_3$) δ 173.1, 141.1, 131.8, 131.6, 128.4, 127.1, 127.1, 123.4, 120.9, 92.9, 82.3, 51.6, 35.3, 30.8; ESI-MS m/z 293.1 (M+Na$^+$).

Example A47

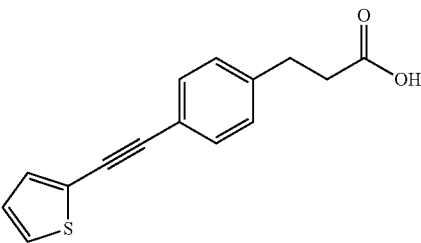 [SMILES: O=C(O)CCc1ccc(C#Cc2cccs2)cc1]

3-(4-(Thiophen-2-ylethynyl)phenyl)propanoic acid. The title compound was prepared from methyl 3-(4-(thiophen-2-ylethynyl)phenyl)propanoate (61 mg, 0.22 mmol) according to the general procedure II to give 18 mg (73%) of a white solid after purification by flash chromatography (SiO$_2$, EtOAc:PE, 1:1): R$_f$=0.16 (EtOAc:PE, 1:2); $^1$H NMR (Acetone-d$_6$) δ 7.39 (dd, J=5.2, 1.2 Hz, 1H), 7.36-7.29 (m, 2H), 7.23-7.15 (m, 3H), 6.96 (dd, J=5.2, 3.6 Hz, 1H), 2.82 (t, J=7.6 Hz, 2H), 2.51 (t, J=7.6 Hz, 2H); $^{13}$C NMR (Acetone-d$_6$) δ 173.78, 143.1, 132.9, 132.2, 129.6, 128.7, 128.3, 123.9, 121.3, 93.6, 82.7, 35.5, 31.4; ESI-MS calcd for C$_{15}$H$_{12}$O$_2$S (M+Na$^+$) 279.0451. found 279.0451.

Example E48

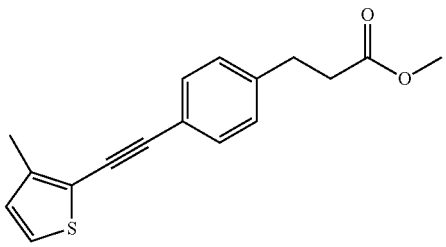 [SMILES: COC(=O)CCc1ccc(C#Cc2sccc2C)cc1]

Methyl 3-(4-((3-methylthiophen-2-yl)ethynyl)phenyl)propanoate. The title compound was prepared from methyl 3-(4-ethynylphenyl)propanoate (95 mg, 0.50 mmol) and 2-bromo-3-methylthiophene (70 μL, 0.62 mmol) according to the general procedure IF to give 75 mg (53%) of a pale yellow solid after purification by flash chromatography (SiO$_2$, EtOAc:PE, 1:5): R$_f$=0.57 (EtOAc:PE, 1:2); $^1$H NMR (CDCl$_3$) δ 7.47-7.40 (m, 2H), 7.17 (dd, J=8.4, 6.7 Hz, 3H), 6.85 (d, J=5.1 Hz, 1H), 3.67 (s, 3H), 2.96 (t, J=7.7 Hz, 2H), 2.63 (t, J=7.7 Hz, 2H), 2.37 (s, 3H); $^{13}$C NMR (CDCl$_3$) δ 173.1, 142.4, 140.8, 131.5, 129.2, 128.3, 125.7, 121.2, 118.7, 95.2, 82.0, 51.6, 35.4, 30.8, 15.0; ESI-MS m/z 307.1 (M+Na$^+$).

Example A48

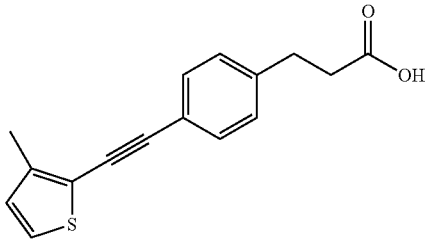 [SMILES: Cc1ccsc1C#Cc1ccc(CCC(=O)O)cc1]

3-(4-((3-Methylthiophen-2-yl)ethynyl)phenyl)propanoic acid. The title compound was prepared from methyl 3-(4-((3-methylthiophen-2-yl)ethynyl)phenyl)propanoate propanoate (55 mg, 0.19 mmol) according to the general procedure II to give 49 mg (95%) of the pure title compound as a white solid: $R_f$=0.45 (EtOAc); $^1$H NMR (Acetone-$d_6$) δ 7.37-7.30 (m, 2H), 7.26 (d, J=5.1 Hz, 1H), 7.19 (d, J=8.3 Hz, 2H), 6.82 (d, J=5.1 Hz, 1H), 2.82 (t, J=7.6 Hz, 2H), 2.51 (t, J=7.6 Hz, 2H), 2.22 (s, 3H); $^{13}$C NMR (Acetone-$d_6$) δ 173.7, 143.3, 142.9, 132.1, 130.4, 129.6, 127.2, 121.7, 119.1, 96.1, 82.4, 35.5, 31.4, 15.0; ESI-MS calcd for $C_{16}H_{14}O_2S$ (M+Na$^+$) 293.0607. found 293.0594.

Example A49

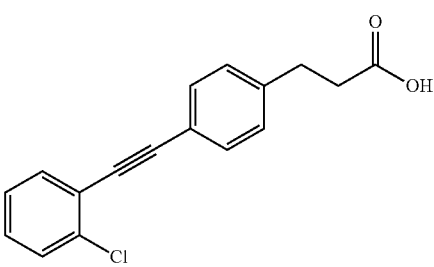

3-(4-((2-Chlorophenyl)etnynyl)phenyl)propanoic acid. The title compound was prepared from methyl 3-(4-((2-chlorophenyl)ethynyl)phenyl)propanoate (8 mg, 0.03 mmol) according to the general procedure II to give 7 mg (95%) of the pure title compound as a pale yellow solid: $R_f$=0.56 (EtOAc with 1.25% AcOH); $^1$HNMR (CDCl$_3$) δ 7.51-7.49 (m, 3H), 7.26-7.24 (m, 1H), 7.22-7.20 (m, 5H), 2.98-2.96 (t, 2H, J=7.7 Hz), 2.70-2.68 (t, 2H, J=7.8 Hz); $^{13}$CNMR (CDCl$_3$) δ 177.3, 141.0, 135.9, 133.2, 131.9, 129.3, 129.3, 129.0, 128.5, 126.5, 123.3, 121.0, 94.4, 86.0, 35.0, 30.6.

Example E49

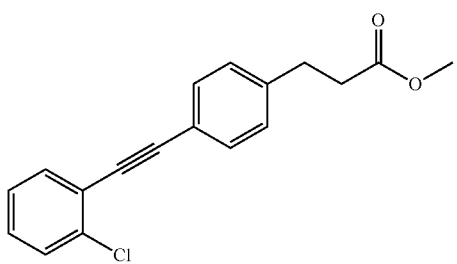 [SMILES: COC(=O)CCc1ccc(C#Cc2ccccc2Cl)cc1]

Methyl 3-(4-((2-chlorophenyl)ethynyl)phenyl)propanoate. The title compound was prepared from 3-(4-ethynyl)phenyl)propanoate (93 mg, 0.49 mmol) and 1-chloro-2-iodobenzene (117 mg, 0.49 mmol) according to the general procedure IC to give 8 mg (6%) of an yellow solid after purification by flash chromatography (SiO$_2$, EtOAc:PE, 1:5): $R_f$=0.38 (EtOAc:PE, 1:5); $^1$HNMR (CDCl$_3$) δ 7.50-7.47 (m, 3H), 7.27-7.22 (m, 1H), 7.22-7.20 (m, 4H), 3.66 (s, 3H), 2.98-2.96 (t, 2H, J=7.7 Hz), 2.66-2.63 (t, 2H, J=7.8 Hz); $^{13}$CNMR (CDCl$_3$) δ 173.2, 141.4, 135.9, 133.3, 131.9, 129.4, 129.3, 128.5, 126.3, 123.4, 120.9, 96.6, 86.0, 51.7, 35.5, 30.9.

Example E50

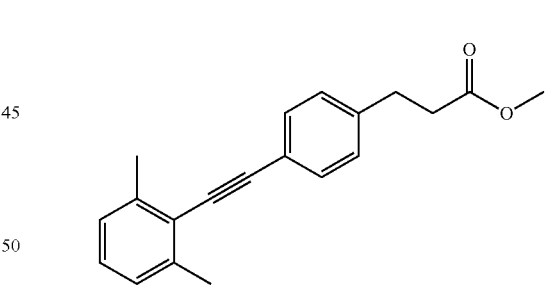

Methyl 3-(4-((2,6-dimethylphenyl)ethynyl)phenyl)propanoate. The title compound was prepared from 3-(4-ethynyl)phenyl)propanoate (80 mg, 0.43 mmol) and 2-iodo-1,3-dimethylbenzene (99 mg, 0.43 mmol) according to the general procedure IC to give 33 mg (27%) of an yellow solid after purification by flash chromatography (SiO$_2$, EtOAc:PE, 1:5): $R_f$=0.31 (EtOAc:PE, 1:5); $^1$HNMR (CDCl$_3$) δ 7.48-7.45 (dd, 2H), 7.30 (t, 1H), 7.20-7.17 (m, 2H), 7.09-7.03 (d, 2H), 3.66 (s, 3H), 2.98-2.96 (t, 2H, J=7.7 Hz), 2.66-2.63 (t, 2H, J=7.8 Hz); $^{13}$CNMR (CDCl$_3$) δ 173.3, 140.8, 140.3, 131.7, 128.5, 127.8, 126.8, 121.9, 97.9, 86.9, 51.8, 35.7, 30.9, 21.3.

Example A50

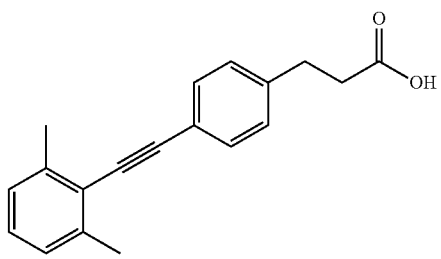 [SMILES: Cc1cccc(C)c1C#Cc1ccc(CCC(=O)O)cc1]

3-(4-((2,6-Dimethylphenyl)etnynyl)phenyl)propanoic acid. The title compound was prepared from methyl 3-(4-((2,6-dimethylphenyl)ethynyl)phenyl)propanoate (33 mg, 0.12 mmol) according to the general procedure II to give 34 mg (100%) of the pure title compound as a pale yellow solid: $R_f$=0.59 (EtOAc with 1.25% AcOH); $^1$HNMR (CDCl$_3$) δ 7.49-7.47 (m, 2H), 7.22-7.22 (m, 3H), 7.10-7.08 (m, 2H), 2.98 (t, 2H, J=7.7 Hz), 2.70 (t, 2H, J=7.8 Hz); $^{13}$CNMR (CDCl$_3$) δ 178.8, 140.4, 131.6, 128.4, 126.8, 123.0, 121.9, 97.7, 86.9, 35.4, 30.5, 21.1.

Example A51

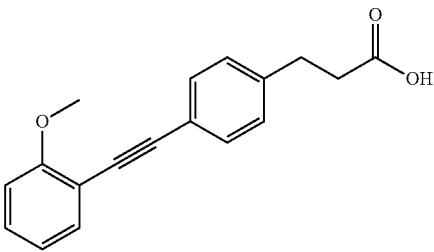

3-(4-((2-Methoxyphenyl)ethynyl)phenyl) acid. The title compound was prepared from methyl 3-(4-((2-methoxyphenyl)ethynyl)phenyl)propanoate (82 mg, 0.28 mmol) according to the general procedure II to give a brown solid. $R_f$=0.08 (EtOAc:PE); $^1$H NMR ((CD$_3$)$_2$CO): δ 7.48-7.44 (m, 3H) 7.36-7.30 (m, 3H) 7.07-7.04 (m, 1H) 6.96-6.95 (m, 1H) 3.90 (s, 3H) 2.95 (t, J=7.7 Hz, 2H) 2.65 (t, J=7.8 Hz, 2H); $^{13}$C NMR ((CD$_3$)$_2$CO): δ 173.8, 161.0, 142.5, 134.0, 132.2, 131.9, 130.8, 129.5, 122.3, 121.2, 112.0, 93.8, 86.4, 56.1, 35.6, 31.4; ESI-MS calcd for C$_{18}$H$_{16}$O$_3$ (M+Na$^+$).

Example E51

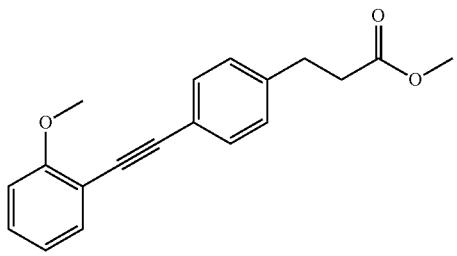 [SMILES: COC(=O)CCc1ccc(C#Cc2ccccc2OC)cc1]

Methyl 3-(4-((2-methoxyphenyl)ethynyl)phenyl)propanoate. The title compound was prepared from methyl 3-(4-iodophenyl)propanoate (90 mg, 0.31 mmol) and 1-ethynyl-2-methoxybenzen (40 μL, 0.31 mmol) according to the general procedure IC to give 86 mg (94%) of a pure orange-brown oil. $R_f$=0.44 (EtOAc:PE; 1:2); $^1$H NMR (CDCl$_3$): δ 7.48 (d, J=8.1 Hz, 3H) 7.29-7.22 (m, 1H) 7.16 (d, J=8.2 Hz, 2H) 6.95-6.88 (m, 2H) 3.90 (s, 3H) 3.66 (s, 3H) 2.95 (t, J=7.6 Hz, 2H) 2.63 (t, J=7.6 Hz, 2H); $^{13}$C NMR (CDCl$_3$): δ 173.3, 160.1, 140.8, 133.7, 132.0, 129.8, 128.4, 121.7, 120.6, 112.7, 110.9, 93.5, 85.6, 56.0, 51.8, 35.6, 31.0; ESI-MS m/z 317.0 (M+Na$^+$).

Example E52

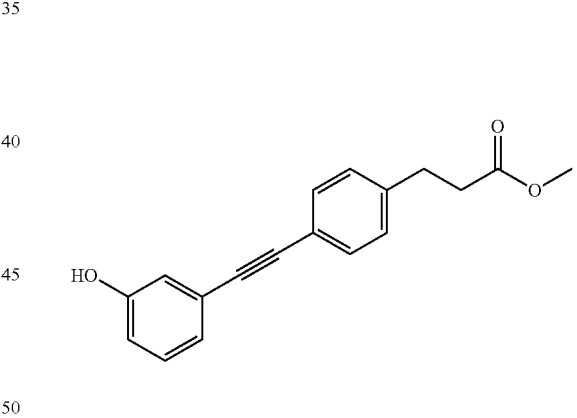

Methyl 3-(4-((3-hydroxyphenyl)ethynyl)phenyl)propanoate. The title compound was prepared from methyl 3-(4-iodophenyl)propanoate (100 mg, 0.34 mmol) and 3-ethynylphenol (0.025 mL, 0.38 mmol) according to the general procedure IC to give 66 mg (69%) of a light brown solid after purification by flash chromatography (SiO$_2$, EtOAc:PE, 1:6→1:0). $R_f$=0.24 (EtOAc:PE; 1:2); $^1$H NMR (CDCl$_3$): δ 7.43 (d, J=8.0 Hz, 2H), 7.20-7.15 (m, 3H), 7.10-7.08 (m, 1H), 7.00-6.99 (m, 1H), 6.84-6.80 (m, 1H), 5.50 (br, 1H), 3.68 (s, 3H), 2.96 (t, J=8.0 Hz, 2H), 2.64 (t, J=8.1 Hz, 2H); $^{13}$C NMR (CDCl$_3$): δ 173.7, 155.7, 141.0, 132.0, 129.8, 128.5, 124.7, 124.4, 121.3, 118.4, 115.9, 89.4, 89.0, 52.0, 35.6, 31.0; ESI-MS m/z 303.0 (M+Na$^+$).

Example A52

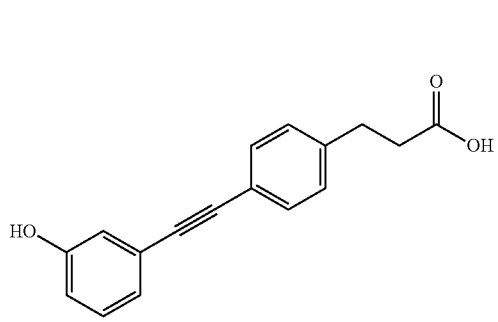 [SMILES: O=C(O)CCc1ccc(C#Cc2cccc(O)c2)cc1]

3-(4-((3-Hydroxyphenyl)ethynyl)phenyl)propanoic acid. The title compound was prepared from methyl 3-(4-((3-hydroxyphenyl)ethynyl)phenyl)propanoate (54 mg, 0.19 mmol) according to the general procedure II to a white solid. $R_f$=0.02 (EtOAc:PE); $^1$H NMR ((CD$_3$)$_2$CO): δ 7.45 (d, J=7.4 Hz, 2H) 7.31 (d, J=7.6 Hz, 2H) 7.25-7.20 (m, 1H) 7.00 (s, 2H) 6.89-6.86 (m, 1H) 2.95 (t, J=7.7 Hz, 2H) 2.64 (t, J=7.3 Hz, 2H); $^{13}$C NMR ((CD$_3$)$_2$CO): δ 173.8, 158.3, 142.8, 132.4, 130.6, 129.5, 125.1, 123.7, 121.8, 118.8, 116.8, 89.7, 89.6, 35.5, 31.4.

Example E53

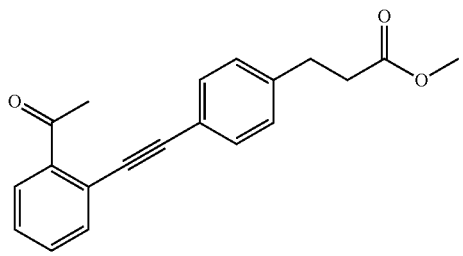 [SMILES: COC(=O)CCc1ccc(C#Cc2ccccc2C(C)=O)cc1]

Methyl 3-(4-((2-acetylphenyl)ethylnyl)phenyl)propanoate. The title compound was prepared from methyl 3-(4-ethynylphenyl)propanoate (100 mg, 0.53 mmol) and 1-(2-iodophenyl)ethanone (144 mg, 0.58 mmol) according to the general procedure IF to give 42 mg (26%) of a brown oil after purification by flash chromatography (SiO$_2$, EtOAc:PE, 1:8→1:2). $R_f$=0.45 (EtOAc:PE, 1:1); $^1$H NMR (CDCl$_3$): δ 7.75 (dd, J=7.8 Hz, 1.0 Hz, 1H), 7.62 (dd, J=7.8 Hz, 1.0 Hz, 1H), 7.48 (t, J=2.3 Hz, 1H), 7.47-7.45 (m, 2H), 7.39 (td, J=7.5 Hz, 1.5 Hz, 1H), 7.21 (d, J=8.5 Hz, 1H), 3.67 (s, 3H), 2.97 (t, J=7.5 Hz, 2H), 2.79 (s, 3H), 2.66-2.61 (m, 2H); $^{13}$C NMR (CDCl$_3$): δ 200.3, 173.0, 141.5, 140.7, 133.8, 131.7, 131.3, 128.6, 128.5, 128.2, 121.8, 120.8, 95.0, 88.2, 51.6, 35.3, 30.8, 30.0; ESI-MS m/z 329.1 (M+Na$^+$).

Example A53

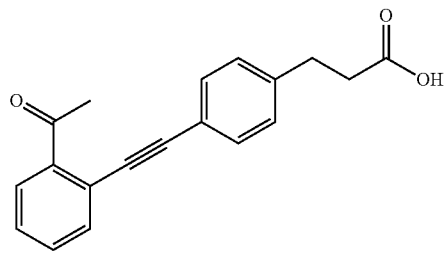 [SMILES: CC(=O)c1ccccc1C#Cc1ccc(CCC(=O)O)cc1]

3-(4-((2-Acetylphenyl)ethynyl)phenyl)propanoic acid. The title compound was prepared from methyl 3-(4-((2-acetylphenyl)ethylnyl)phenyl)propanoate (33 mg, 0.11 mmol) according to the general procedure II to give 7 mg (21%) of a yellow solid after purification by flash chromatography (SiO$_2$, EtOAc:PE, 1:4→EtOAc with 1.25% AcOH). $R_f$=0.50 (EtOAc with 1.25% AcOH); $^1$H NMR (Acetone-d$_6$): δ 7.79 (dd, J=7.8 Hz, 1.0 Hz, 1H), 7.67 (dd, J=7.8 Hz, 1.0 Hz, 1H), 7.57 (td, J=7.5 Hz, 1.5 Hz, 1H), 7.53-7.49 (m, 3H), 7.35 (d, J=8.3 Hz, 2H), 2.73 (s, 3H), 2.67 (t, J=6.9 Hz, 2H); $^{13}$CNMR (Acetone-d$_6$): δ 199.8, 173.7, 143.3, 142.0, 134.5, 132.4, 132.2, 129.6, 129.5, 129.3, 122.2, 121.6, 95.3, 88.9, 35.5, 31.4, 30.3; ESI-MS calcd for C$_{19}$H$_{16}$O$_3$(MNa$^+$): 315.0992. found: 315.0984.

Example E54

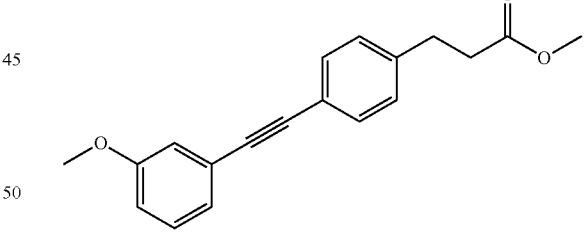

Methyl 3-(4-((3-methoxyphenyl)ethynyl)phenyl)propanoate. The title compound was prepared from methyl 3-(4-((3-hydroxyphenyl)ethynyl)phenyl)propanoate (41 mg, 0.20 mol) and iodomethane (60 μL, 0.97 mmol) according to the general procedure IV to give 38 mg (69%) of a pure yellow oil. $R_f$=0.37 (EtOAc:PE, 1:3); $^1$H NMR (CDCl$_3$): δ 7.45 (dt, J=8.3 Hz, 2.0 Hz, 2H), 7.27-7.23 (m, 1H), 7.18 (d, J=8.3 Hz, 2H), 7.12 (dt, J=7.5 Hz, 1.3 Hz, 1H), 7.05 (dd, J=2.8 Hz, 1.5 Hz, 1H), 6.88 (ddd, J=8.4 Hz, 2.4 Hz, 1.0 Hz, 1H), 3.82 (s, 3H), 3.76 (s, 3H), 2.63 (t, J=7.8 Hz, 2H); $^{13}$C NMR (CDCl$_3$): δ 173.1, 159.3, 140.9, 131.8, 129.4, 128.3, 124.3, 124.1, 121.1, 116.3, 114.8, 89.1, 89.0, 55.3, 51.6, 35.4, 30.8.

Example A54

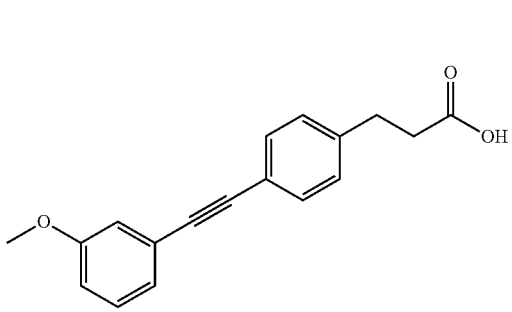 [SMILES: COc1cccc(C#Cc2ccc(CCC(=O)O)cc2)c1]

3-(4-((3-Methoxyphenyl)ethynyl)phenyl)propanoic acid. The title compound was prepared from methyl 3-(4-((3-methoxyphenyl)ethynyl)phenyl)-propanoate (38 mg, 0.13 mmol) following the general procedure II to give 34 mg (94%) of a pure white solid. $R_f$=0.53 (EtOAc with 1.25% AcOH); $^1$H NMR (DMSO-$d_6$): δ 11.99 (s, 1H), 7.46 (d, J=6.5 Hz, 2H), 7.35-7.28 (m, 3H), 7.12-7.08 (m, 2H), 6.98 (ddd, J=8.3 Hz, 2.5 Hz, 0.8 Hz, 1H), 3.79 (s, 3H), 2.85 (t, J=7.5 Hz, 2H), 2.55 (t, J=7.5 Hz, 2H); $^{13}$C NMR (DMSO-$d_6$): δ 173.9, 159.2, 142.0, 131.3, 129.9, 128.7, 123.7, 123.5, 119.8, 116.0, 115.2, 89.2, 88.8, 55.2, 34.9, 30.2; ESI-MS calced for $C_{18}H_{16}O_3$ (MNa$^+$): 303.0992. found: 303.0992.

Example A55

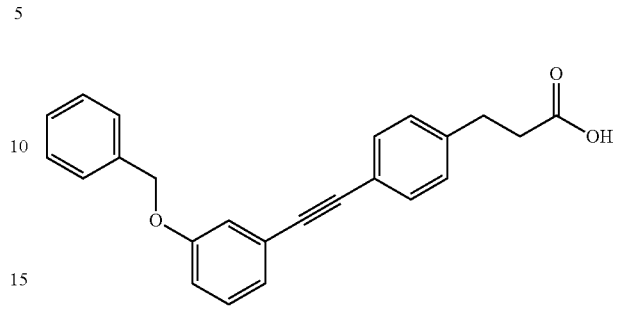

3-(4-((3-(Benzyloxy)phenyl)ethynyl)phenyl)propanoic acid. The title compound was prepared from methyl 3-(4-((3-(benzyloxy)phenyl)ethynyl)phenyl)propanoate (85 mg, 0.23 mmol) following the general procedure II to give 74 mg (90%) of a pure pale yellow solid. $R_f$=0.56 (EtOAc with 1.25% AcOH); $^1$H NMR (DMSO-$d_6$): δ 12.15 (s, 1H), 7.47-7.45 (m, 4H), 7.42-7.38 (m, 2H), 7.36-7.28 (m, 4H), 7.18-7.17 (m, 1H), 7.12 (dt, J=7.8 Hz, 1.0 Hz, 1H), 7.06 (ddd, J=8.3 Hz, 2.5 Hz, 1.0 Hz, 1H), 5.15 (s, 2H), 2.85 (t, J=7.5 Hz, 2H), 2.55 (t, J=7.5 Hz, 2H); $^{13}$C NMR (DMSO-$d_6$): δ 173.7, 158.3, 142.0, 136.9, 131.4, 129.9, 128.7, 128.4, 127.9, 127.7, 124.0, 123.5, 119.8, 116.9, 116.0, 89.3, 88.8, 69.3, 34.8, 30.2; ESI-MS calced for $C_{24}H_{20}O_3$(MNa$^+$): 379.1305. found: 379.1291.

Example E55

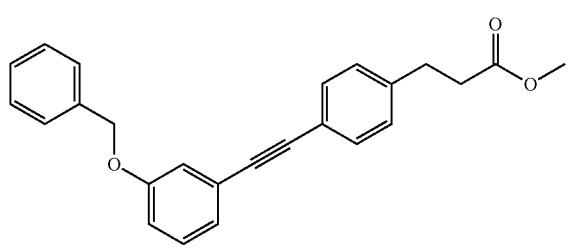 [SMILES: COC(=O)CCc1ccc(C#Cc2cccc(OCc3ccccc3)c2)cc1]

Methyl 3-(4-((3-(benzyloxy)phenyl)ethynyl)phenyl)propanoate. The title compound was prepared from methyl 3-(4-((3-hydroxyphenyl)ethynyl)phenyl)propanoate (98 mg, 0.45 mmol) and (bromomethyl)benzene (142 mg, 1.03 mmol) according to the general procedure IV to give 112 mg (68%) of a pure pale yellow solid. $R_f$=0.60 (EtOAc:PE, 1:1); $^1$H NMR (CDCl$_3$): δ 7.46-7.32 (m, 7H), 7.46-7.22 (m, 1H), 7.17 (d, J=8.5 Hz, 2H), 7.14-7.12 (m, 2H), 6.95 (ddd, J=8.3 Hz, 2.8 Hz, 1.0 Hz, 1H), 5.07 (s, 2H), 3.66 (s, 3H), 2.95 (t, J=7.8 Hz, 2H), 2.63 (t, J=7.8 Hz, 2H); $^{13}$C NMR (CDCl$_3$): δ 173.8, 158.6, 140.9, 136.7, 131.8, 129.4, 128.6, 128.3, 128.0, 127.5, 124.4, 124.4, 121.1, 117.3, 115.6, 89.2, 89.0, 70.0, 51.6, 35.4, 30.8; MALDI-MS m/z 393.4 (M+Na$^+$).

Example E56

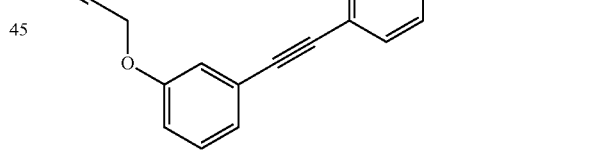

Methyl 3-(4-((3-(prop-2-ynyloxy)phenyl)ethynyl)phenyl) propanoate. The title compound was prepared from methyl 3-(4-((3-hydroxyphenyl)ethynyl)phenyl)propanoate (100 mg, 0.45 mmol) and 3-bromoprop-1-yne (129 mg, 0.93 mmol) according to the general procedure IV to give 105 mg (72%) of a pure light brown oily product. $R_f$=0.56 (EtOAc: PE, 1:1); $^1$H NMR (CDCl$_3$): δ 7.46 (dt, J=6.3 Hz, 1.8 Hz, 2H), 7.28-7.25 (m, 1H), 7.19, 7.15 (m, 3H), 7.12 (dd, J=2.5 Hz, 1.3 Hz, 1H), 6.96 (ddd, J=8.3 Hz, 2.8 Hz, 1.0 Hz, 1H), 4.70 (d, J=2.5 Hz, 2H), 3.67 (s, 3H), 2.96 (t, J=7.7 Hz, 2H), 2.64 (t, J=7.8 Hz, 2H), 2.54 (t, J=2.4 Hz, 1H); $^{13}$C NMR (CDCl$_3$): δ 173.1, 157.3, 141.0, 131.8, 129.4, 128.3, 125.0, 124.4, 121.0, 117.4, 115.6, 89.3, 88.8, 78.3, 75.7, 55.9, 51.6, 35.4, 30.8; MALDI-MS m/z 341.4 (M+Na$^+$).

Example A56

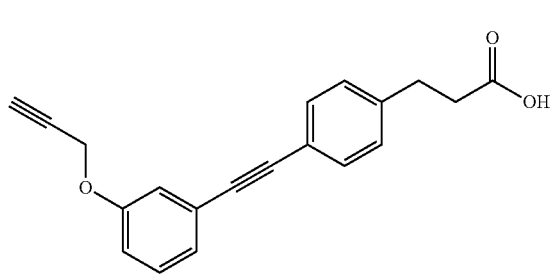 [SMILES: C#CCOc1cccc(C#Cc2ccc(CCC(=O)O)cc2)c1]

3-(4-((3-(Prop-2-ynyloxy)phenyl)ethynyl)phenyl)propanoic acid. The title compound was prepared from methyl 3-(4-((3-(prop-2-ynyloxy)phenyl)ethynyl)phenyl)propanoate (71 mg, 0.22 mmol) following the general procedure II to give 49 mg (73%) of a white solid after purification by flash chromatography (SiO$_2$, cyclohexane:[EtOAc with 1.25% AcOH], 1:1). R$_f$=0.61 (EtOAc with 1.25% AcOH); $^1$H NMR (Acetone-d$_6$): δ 10.56 (s, 1H), 7.47 (dd, J=8.3 Hz, 2H), 7.37-7.13 (m, 3H), 7.17-7.15 (m, 2H), 7.04 (ddd, J=8.5 Hz, 2.8 Hz, 1.0 Hz, 1H), 4.84 (d, J=2.3 Hz, 2H), 3.11 (t, J=2.4 Hz, 1H), 2.95 (t, J=7.7 Hz, 2H), 2.65 (t, J=7.5 Hz, 2H); $^{13}$C NMR (Acetone-d$_6$): δ 173.8, 158.6, 42.9, 132.4, 132.4, 130.6, 129.6, 125.5, 125.2, 121.6, 118.1, 116.6, 90.1, 89.4, 79.5, 77.3, 56.4, 35.5, 31.4; ESI-MS calced for O$_{20}$H$_{16}$O$_3$(MNa$^+$): 327.0993. found: 327.0986.

Example A57

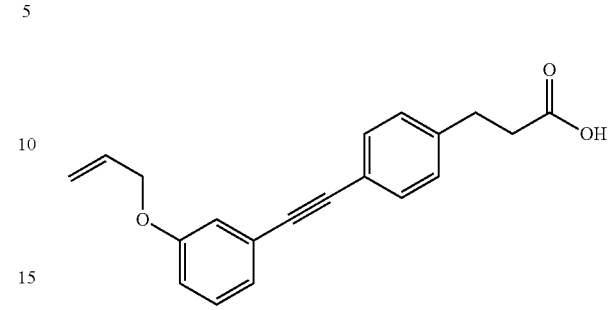

3-(4-((3-(Allyloxy)phenyl)ethynyl)phenyl)propanoic acid. The title compound was prepared from methyl 3-(4-((3-(allyloxy)phenyl)ethynyl)phenyl)propanoate (72 mg, 0.23 mmol) following the general procedure II to give 49 mg (73%) of a pure white solid. R$_f$=0.70 (EtOAc with 1.25% AcOH); $^1$H NMR (DMSO-d$_6$): δ 12.12 (s 1H), 7.46 (d, J=8.3 Hz, 2H), 7.32-7.28 (m, 3H), 7.12-7.09 (m, 2H), 7.06 (ddd, J=8.3 Hz, 2.8 Hz, 1.0 Hz, 1H), 6.09-6.00 (m, 1H), 5.40 (dq, J=17.1 Hz, 1.7 Hz, 1H), 5.27 (dq, J=10.5 Hz, 1.5 Hz, 1H), 4.61 (dt, J=5.3 Hz, 1.5 Hz, 2H), 2.85 (t, J=7.5 Hz, 2H), 2.55 (t, J=7.5 Hz, 2H); $^{13}$C NMR (DMSO-d$_6$): δ 173.7, 158.1, 142.0, 133.5, 131.4, 129.9, 128.7, 123.9, 123.5, 119.8, 117.5, 116.8, 115.9, 89.2, 88.8, 68.2, 34.8, 30.2; ESI-MS calced for C$_{20}$H$_{16}$O$_3$ (MNa$^+$): 329.1149. found: 329.1157.

Example E57

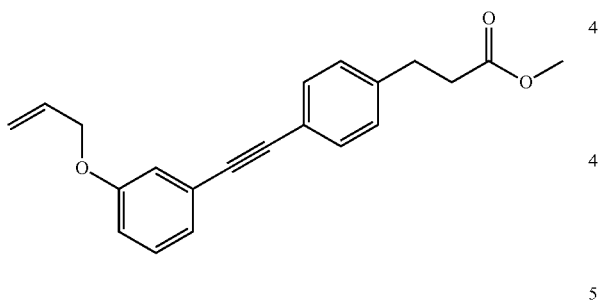

Methyl 3-(4-((3-(allyloxy)phenyl)ethynyl)phenyl)propanoate. The title compound was prepared from methyl 3-(4-((3-hydroxyphenyl)ethynyl)phenyl)propanoate (100 mg, 0.45 mmol) and 3-bromoprop-1-ene (133 mg, 0.96 mmol) according to the general procedure IV to give 101 mg (70%) of a pale yellow oily product. R$_f$=0.55 (EtOAc:PE, 1:1); $^1$H NMR (CDCl$_3$): δ 7.45 (d, J=8.0 Hz, 2H), 7.24 (t, J=1.3 Hz, 1H), 7.18 (d, J=8.0 Hz, 2H), 7.12 (d, J=7.8 Hz, 1H), 7.06 (t, J=1.9 Hz, 1H) 6.90 (dd, J=8.3 Hz, 2.5 Hz, 1H), 6.10-6.00 (m, 1H), 5.42 (dd, J=17.3 Hz, 1.5 Hz, 1H), 5.30 (dd, J=10.5 Hz, 1.3 Hz, 1H), 4.55 (dt, J=5.3 Hz, 1.3 Hz, 2H), 3.67 (s, 3H), 2.96 (t, J=7.8 Hz, 2H), 2.63 (t, J=7.8 Hz, 2H); $^{13}$C NMR (CDCl$_3$): δ 173.1, 158.3, 140.9, 133.0, 131.7, 129.4, 128.3, 124.3, 124.3, 121.1, 117.7, 117.2, 115.6, 89.1, 89.0, 68.8, 51.6, 35.4, 30.8; MALDI-MS m/z 343.4 (M+Na$^+$).

Example E58

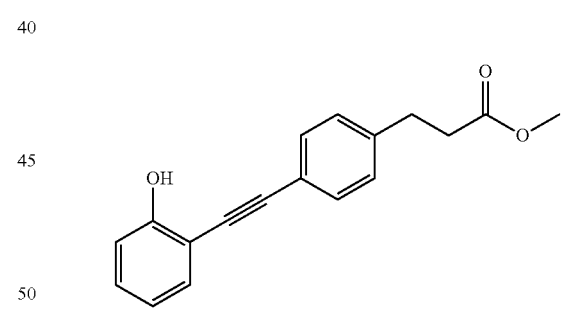

Methyl 3-(4-((2-hydroxyphenyl)ethynyl)phenyl)propanoate. The title compound was prepared from methyl 3-(4-ethynylphenyl)propanoate (102 mg, 0.53 mmol) and 2-iodophenol (130 mg, 0.58 mmol) according to the general procedure IF to give 19 mg (13%) of a white solid after purification by flash chromatography (SiO$_2$, EtOAc:PE, 1:10). R$_f$=0.28 (EtOAc:PE, 1:5); $^1$H NMR (CDCl$_3$): δ 7.79 (dt, J=8.3 Hz, 2.0 Hz, 2H), 7.56 (d, J=1.0 Hz, 1H), 7.50 (d, J=1.0 Hz, 1H), 7.29-7.21 (m, 3H), 6.98 (d, J=1.0 Hz, 1H), 3.68 (s, 3H), 2.99 (t, J=7.8 Hz, 2H), 2.60 (t, J=7.8 Hz, 2H); $^{13}$C NMR (CDCl$_3$): δ 173.2, 155.9, 154.8, 141.1, 129.3, 128.7, 128.8, 125.1, 124.1, 122.9, 120.9, 111.1, 100.9, 51.6, 35.5, 30.7; ESI-MS m/z 303.1 (M+Na$^+$).

Example A58

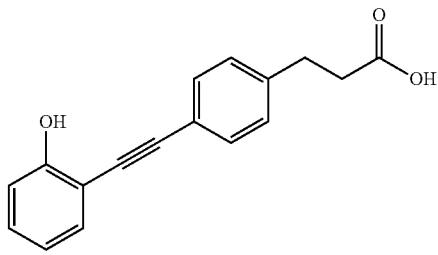 [SMILES: O=C(O)CCc1ccc(C#Cc2ccccc2O)cc1]

3-(4-((2-Hydroxyphenyl)ethynyl)phenyl)propanoic acid. The title compound was prepared from methyl 3-(4-((2-hydroxyphenyl)ethynyl)phenyl)propanoate (18 mg, 0.07 mmol) according to the general procedure II to give 15 mg (83%) of a pure white solid. $R_f$=0.60 (EtOAc with 1.25% AcOH); $^1$H NMR (DMSO-$d_6$): δ 7.83 (d, J=8.0 Hz, 2H), 7.64-7.60 (m, 2H), 7.37 (d, J=8.0 Hz, 3H), 7.33-7.23 (m, 2H), 2.88 (t, J=7.5 Hz, 2H), 2.58 (t, J=7.5 Hz, 2H); $^{13}$C NMR (DMSO-$d_6$): δ 173.8, 155.3, 154.1, 141.9, 129.0, 128.9, 127.6, 124.7, 124.4, 123.2, 121.0, 111.1, 101.4, 35.0, 30.2; ESI-MS calcd for $C_{17}H_{14}O_3$(MNa$^+$): 289.0836. found: 289.0843.

Example A59

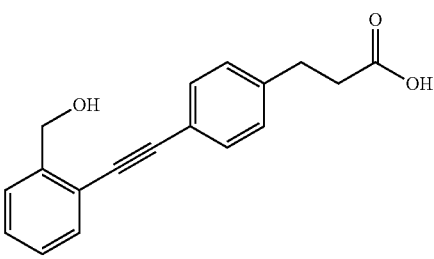

3-(4-((2-Hydroxymethyl)phenyl)ethynyl)phenyl)propanoic acid. The title compound was prepared from methyl 3-(4-((2-hydroxymethyl)phenyl)ethynyl)phenyl)propanoate (26 mg, 0.08 mmol) according to the general procedure II to give 21 mg (83%) of a pure white solid after recrystallization in PE. $R_f$=0.60 (EtOAc:PE, 2:1); $^1$HNMR ((CD$_3$)$_2$CO): δ 7.50 (d, J=6.0 Hz, 1H), 7.36 (d, J=6.0 Hz, 3H), 7.27 (t, J=5.4 Hz, 1H), 7.20 (d, J=6.0 Hz, 2H), 7.15 (t, J=5.4 Hz, 1H) 2.82 (t, J=5.7 Hz, 2H), 2.52 (t, J=5.7 Hz, 2H); $^{13}$CNMR ((CD$_3$)$_2$CO): δ 173.7, 145.0, 142.9, 132.4, 132.3, 129.6, 129.4, 127.5, 127.2, 121.8, 94.8, 87.2, 62.9, 35.6, 31.4.

Example E59

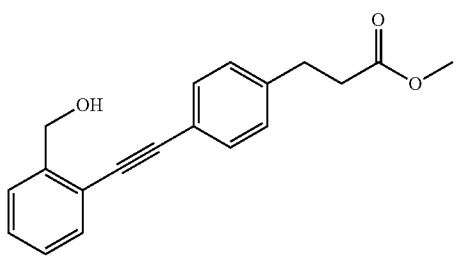 [SMILES: COC(=O)CCc1ccc(C#Cc2ccccc2CO)cc1]

Methyl 3-(4-((2-hydroxymethyl)phenyl)ethynyl)phenyl)propanoate. The title compound was prepared from methyl 3-(4-ethynylphenyl)propanoate (100 mg, 0.53 mmol) and 2-iodobenzyl alcohol (187 mg, 0.80 mmol) according to the general procedure IF to give 27 mg (19%) of a dark orange oil after purification by flash chromatography (SiO$_2$, EtOAc:PE, 1:3). $R_f$=0.25 (EtOAc:PE, 1:3); $^1$HNMR (CDCl$_3$): δ 7.52 (dd, J=5.7 Hz, 0.9 Hz, 1H), 7.48-7.44 (m, 3H), 7.35 (td, J=5.7 Hz, 0.9 Hz, 1H), 7.29 (dd, J=5.7 Hz, 1.2 Hz, 1H), 7.20-7.18 (m, 2H), 4.90 (s, 2H), 3.67 (s, 3H), 2.97 (t, J=6.0 Hz, 2H), 2.64 (t, J=5.7 Hz, 2H); $^{13}$CNMR (CDCl$_3$): δ 173.1, 142.6, 141.3, 132.1, 131.7, 128.7, 128.5, 127.5, 127.3, 121.4, 120.9, 94.2, 86.5, 64.0, 51.7, 35.4, 30.9.

Example E60

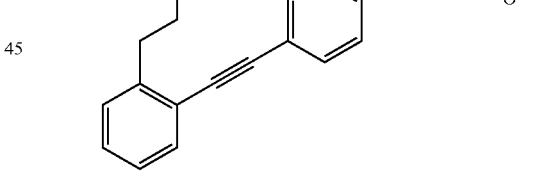

Methyl 3-(4-((2-(2-hydroxyethyl)phenyl)ethynyl)phenyl)propanoate. The title compound was prepared from methyl 3-(4-ethynylphenyl)propanoate (107 mg, 0.57 mmol) and 2-bromophenethyl alcohol (100 μL, 0.74 mmol) according to the general procedure IF to give 83 mg (47%) of a dark orange oil after purification by flash chromatography (SiO$_2$, EtOAc:PE, 1:1). $R_f$=0.19 (EtOAc:PE, 1:1); $^1$HNMR (CDCl$_3$): δ 7.46-7.44 (m, 1H), 7.38-7.36 (m, 2H), 7.21-7.20 (m, 2H), 7.18-7.14 (m, 1H), 7.13-7.10 (m, 2H), 3.91-3.87 (m, 2H), 3.60 (s, 3H), 3.06 (t, J=5.1 Hz, 2H), 2.89 (t, J=5.7 Hz, 2H), 2.56 (t, J=5.4 Hz, 2H); $^{13}$CNMR (CDCl$_3$): δ 173.1, 141.1, 140.4, 132.4, 131.7, 131.7, 129.7, 128.5, 126.6, 123.2, 121.2, 93.2, 87.6, 62.9, 51.7, 38.1, 35.4, 30.9.

Example A60

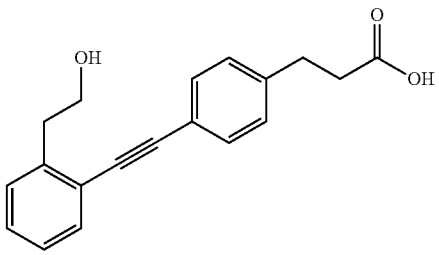 [SMILES: O=C(O)CCc1ccc(C#Cc2ccccc2CCO)cc1]

3-(4-((2-(2-Hydroxyethyl)phenyl)ethynyl)phenyl)propanoic acid. The title compound was prepared from methyl 3-(4-((2-(2-hydroxyethyl)phenyl)ethynyl)phenyl)propanoate (66 mg, 0.21 mmol) according to the general procedure II to give 50 mg (79%) of a pure white solid after recrystallization in PE. $R_f$: 0.44 ([EtOAc with 1.25% AcOH]: PE, 2:1); $^1$HNMR (CDCl$_3$): δ 7.53-7.51 (m, 1H), 7.46-7.44 (m, 2H), 7.28-7.25 (m, 2H), 7.24-7.21 (m, 1H), 7.20-7.18 (m, 2H), 3.96 (t, J=4.8 Hz, 2H), 3.13 (t, J=5.1 Hz, 2H), 2.96 (t, J=5.7 Hz, 2H), 2.67 (t, J=5.7 Hz, 2H); $^{13}$CNMR (CDCl$_3$): δ 178.1, 140.7, 140.3, 132.4, 131.7, 129.7, 128.5, 128.4, 126.6, 123.2 121.3, 93.2 87.6, 62.9, 38.0, 35.2, 30.5.

Example E61

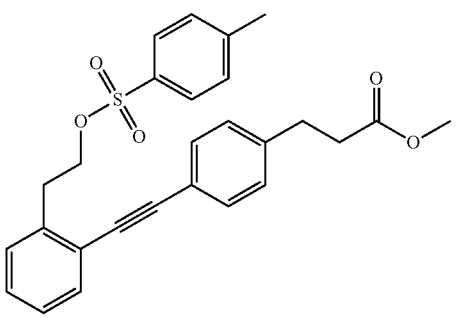 [SMILES: COC(=O)CCc1ccc(C#Cc2ccccc2CCOS(=O)(=O)c2ccc(C)cc2)cc1]

Methyl 3-(4-((2-(2-(tosyloxy)ethyl)phenyl)ethynyl)phenyl)propanoate. Methyl 3-(4-((2-(2-hydroxyethyl)phenyl)ethynyl)phenyl)propanoate (200 mg, 0.65 mmol) in CH$_2$Cl$_2$ (5 ml) was added para-toluenesulfonyl chloride (136 mg, 0.71 mmol). The mixture was cooled to 10° C. and NEt$_3$ (72 mg, 0.71 mmol) in CH$_2$Cl$_2$ (1 ml) was added dropwise. The reaction was allowed to reach room temperature and reacted overnight. The reaction was added 1 M HCl (0.5 ml), water (10 ml) and extracted with CH$_2$Cl$_2$. The organic phases were combined, washed with aq. NaHCO$_3$, dried over MgSO$_4$, concentrated and purified by flash chromatography (SiO$_2$, EtOAc:PE, 1:3) to give 153 mg (51%): $R_f$=0.20 (EtOAc:PE, 1:3); $^1$HNMR (CDCl$_3$): δ 7.66 (d, J=6.3 Hz, 2H), 7.44-7.42 (m, 1H), 7.39 (d, J=6.3 Hz, 2H), 7.26-7.23 (m, 1H), 7.22-7.19 (m, 6H), 4.32 (t, J=5.1 Hz, 2H), 3.68 (s, 3H), 3.21 (t, J=5.7 Hz, 2H), 2.98 (t, J=6.0 Hz, 2H), 2.65 (t, J=5.4 Hz, 2H), 2.38 (s, 3H); $^{13}$CNMR (CDCl$_3$): δ 173.1, 144.5, 141.2, 137.8, 133.0, 132.3, 131.7, 129.9, 129.7, 128.5, 128.5, 127.8, 127.0, 123.1, 120.9, 93.6, 86.8, 51.7, 35.4, 34.4, 30.9, 21.6.

Example A61

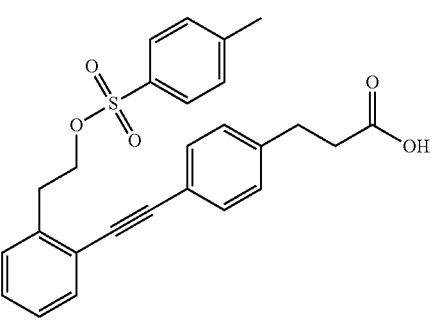 [SMILES: Cc1ccc(S(=O)(=O)OCCc2ccccc2C#Cc2ccc(CCC(=O)O)cc2)cc1]

3-(4-((2-(2-(Tosyloxy)ethyl)phenyl)ethynyl)phenyl)propanoic acid. The title compound was prepared from methyl 3-(4-((2-(2-(tosyloxy)ethyl)phenyl)ethynyl)phenyl)propanoate (52 mg, 0.11 mmol) according to the general procedure II to give 40 mg (82%) of a white solid after recrystallization in PE. $R_f$=0.66 (EtOAc:PE, 2:1); $^1$HNMR (CDCl$_3$): δ 7.66 (d, J=6.3 Hz, 2H) 7.44-7.42 (m, 1H), 7.40 (d, J=6.0 Hz, 2H), 7.24-7.19 (m, 7H), 4.32 (t, J=5.4 Hz, 2H), 3.21 (t, J=5.4 Hz, 2H), 2.99 (t, J=5.7 Hz, 2H), 2.71 (t, J=5.7 Hz, 2H), 2.38 (s, 3H); $^{13}$CNMR (CDCl$_3$): δ 178.3, 144.5, 140.8, 137.8, 133.0, 131.8, 129.9, 129.8, 128.5, 128.5, 127.8, 127.0, 123.1, 121.1, 93.6, 86.9, 69.6, 35.2, 34.4, 30.5, 21.6.

Biological Assays

Materials. Tissue culture media and reagents were purchased from Invitrogen (Karlsruhe, Germany). Sensor microplates and compound source plates were obtained from Corning (Corning, N.Y.). All other laboratory reagents were from Sigma-Aldrich (Taufkirchen, Germany), unless explicitly specified.

Cell Culture and Transfection. 1321N1 cells stably transfected with the human GPR40 were kindly provided by Euroscreen (Gosselies, Belgium). hGPR40-1321N1 cells were grown in Dulbecco's modified Eagle's medium supplemented with 10% (v/v) heat-inactivated fetal calf serum, 1% sodium pyruvate, 100 U/ml penicillin, 100 μg/ml streptomycin, and 400 μg/ml G418. 1321N1, HEK293 cells were grown in Dulbecco's modified Eagle's medium supplemented with 10% (v/v) heat-inactivated fetal calf serum, 1% sodium pyruvate, 100 U/ml penicillin, and 100 μg/ml streptomycin. All cells were kept at 37° C. in a 5% CO2 atmosphere.

For transfection, 4.3×10$^6$ HEK293 cells were seeded into 60 cm$^2$ dishes and incubated overnight at 37° C. and 5% CO$_2$. The transfection was performed by using a calcium phosphate-DNA coprecipitation method. Therefore 20 μg receptor plasmid DNA was diluted in 480 μl of CaCl$_2$ solution (10 mM Tris-HCl, 1 mM EDTA, pH 7.5-8.0, and 250 mM CaCl$_2$) and dropwise added to 500 μl of 2-fold HEPES-buffered saline (2×HBS: 280 mM NaCl, 50 mM HEPES, and 1.5 mM $Na_2HPO_4$; pH 7.1-7.2). After 45 min of incubation at room temperature, the precipitate was added in drops to the cells in 10 ml of fresh culture media. The cells were allowed to express the receptor for 48 hours before performing the functional assays.

Calcium Mobilization Assays. Calcium measurements were performed using a NOVOstar® microplate reader with a built-in pipetor (BMG LabTech, Offenburg, Germany). Cells were seeded in 96-well tissue-culture plates at a density of 30,000 cells per well. On the next day, cells were washed twice in Krebs-HEPES buffer (KHP: 118.6 mM NaCl, 4.7 mM KCl, 1.2 mM KH2PO4, 4.2 mM NaHCO3, 11.7 mM D-glucose, 10 mM HEPES (free acid), 1.3 mM CaCl2 and 1.2 mM MgSO4, pH 7.4) and loaded with 1.5 μM Oregon Green 488 BAPTA-1/AM (Molecular Probes, Eugene, Oreg.) and 0.03% Pluronic F-127 (Invitrogen, Karlsruhe, Germany) for 1 h (37° C., 5% CO2). After addition of KHP buffer, cells were directly transferred to Novostar and kept at 37° C. under exclusion of light for 15 min until the measurement was started. For testing of agonists, 20 μl of a ten-fold concentrated test compound solution was injected sequentially into separate wells and fluorescence was measured at 520 nm (bandwidth 25 nm) for 50 intervals of 0.4 seconds each. The excitation wavelength was 485 nm (bandwidth 25 nm). Concentration-inhibition curves in the presence of the test compounds were obtained by preincubating the cells with the compounds for 30 min at 37° C. prior to injection of agonist.

TABLE 1

Agonistic activity of example compounds on GPR40 in calcium mobilization assay

| Example | GPR40 agonistic activity (pEC$_{50}$) |
|---|---|
| A1 | 5.88 |
| A2 | 5.44 |
| A3 | 4.53 |
| A4 | 6.25 |
| A5 | 7.02 |
| A6 | 7.07 |
| A7 | 7.36 |
| A8 | 6.05 |
| A9 | 7.49 |
| A10 | 6.97 |
| A11 | 7.04 |
| A12 | 7.24 |
| A13 | 6.45 |
| A14 | 7.05 |
| A15 | 7.13 |
| A16 | 7.06 |
| A17 | 5.96 |
| A18 | 6.81 |
| A19 | 5.72 |
| A20 | 5.09 |
| A21 | 5.56 |
| A22 | 6.94 |
| A23 | 5.42 |
| A24 | 5.32 |
| A25 | 3.88 |
| A26 | 3.95 |
| A27 | 7.10 |
| A28 | 7.43 |
| A29 | 6.84 |
| A30 | 7.05 |

TABLE 1-continued

Agonistic activity of example compounds on GPR40 in calcium mobilization assay

| Example | GPR40 agonistic activity (pEC$_{50}$) |
|---|---|
| A31 | 6.91 |
| A32 | 5.95 |
| A33 | 7.25 |
| A34 | 4.96 |
| A35 | 7.37 |
| A36 | 6.86 |
| A37 | 7.03 |
| A38 | 6.51 |
| A40 | 6.00 |
| A49 | 6.82 |
| A50 | 6.38 |
| A51 | 6.66 |
| A52 | 6.35 |
| A53 | 6.73 |
| A54 | 7.15 |
| A55 | 6.28 |
| A56 | 7.11 |
| A57 | 6.84 |
| A58 | 4.79 |
| A59 | 6.24 |
| A60 | 5.69 |
| A61 | 6.50 |

The invention claimed is:
1. A compound of the formula (I)

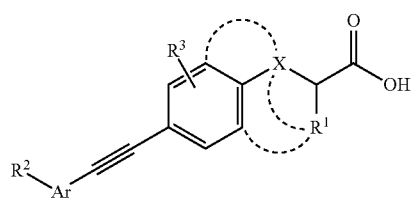

or a salt thereof
wherein
Ar is an optionally substituted monocyclic or fused aromatic or heteroaromatic ring system, wherein said fused aromatic ring system is an aryl fused with another aromatic ring;
X is —C($R^4R^5$)—, —N($R^4$)—, or —S(O)$_n$—;
n is an integer of 0-2;
$R^1$, $R^2$, $R^3$, $R^4$, and $R^6$ are independently selected from the group consisting of hydrogen, ($C_1$-$C_{10}$)alkyl, ($C_2$-$C_{10}$)alkenyl, ($C_2$-$C_{10}$)alkynyl, ($C_1$-$C_{10}$)alkylene, ($C_1$-$C_{10}$)alkoxy, ($C_2$-$C_{10}$)dialkylamino, ($C_1$-$C_{10}$)alkylthio, ($C_2$-$C_{10}$)heteroalkyl, ($C_2$-$C_{10}$)heteroalkylene, ($C_3$-$C_{10}$)cycloalkyl, ($C_3$-$C_{10}$)heterocycloalkyl, ($C_3$-$C_{10}$)cycloalkylene, ($C_3$-$C_{10}$)heterocycloalkylene, halo, ($C_1$-$C_{10}$)haloalkyl, ($C_1$-$C_{10}$)perhaloalkyl, ($C_2$-$C_{10}$)-alkenyloxy, $(C_3-C_{10})$-alkynyloxy, aryloxy, arylalkyloxy, heteroaryloxy, heteroarylalkyloxy, $(C_1-C_6)$alkyloxy-$(C_1-C_4)$alkyl, aryl or substituted aryl, heteroaryl or substituted heteroaryl selected from 1-pyrrolyl, 2-pyrrolyl, 3-pyrrolyl, 1-pyrazolyl, 3-pyrazolyl, 5-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 2-pyrimidinyl, 4-pyrimidinyl, 5-pyrimidinyl, 3-pyridazinyl or 4-pyridazinyl, and arylalkyl or substituted arylalkyl;

$R^2$ may be further substituted by $R^6$;

$R^5$ is selected from hydrogen and optionally substituted $(C_1-C_3)$alkyl;

----, ------, or -------- define that $R^1$ and $R^4$, when not selected from halo, may optionally be connected to the benzene ring in ortho position relative to X, to $R^3$, to X or to each other by a covalent bond, —O—, or —S(O)$_n$—, wherein substituted means one or more substituents selected from the group consisting of —OR', =O, =NR', =N—OR', —NR'R", —SR', halogen, —OC(O)R', —C(O)R', —CO$_2$R', —CONR'R", —OC(O)NR'R", —NR'—C(O)NR"R''', —NR'—SO$_2$NR"R''', —NH—C(NH$_2$)=NH, —NR'C(NH$_2$)=NH, —NH—C(NH$_2$)=NR', —SiR'R"R''', —S(O)R', —SO$_2$R', —SO$_2$NR'R", —NR"SO$_2$R, —CN, —(C$_2$-C$_5$)alkynyl, —(C$_2$-C$_5$)alkenyl, and —NO$_2$, in a number ranging from zero to three, said R', R" and R''' each independently refer to hydrogen, unsubstituted $(C_1-C_6)$alkyl and $(C_2-C_6)$heteroalkyl, unsubstituted aryl, aryl substituted with one to three halogens, unsubstituted $(C_1-C_4)$-alkyl, $(C_1-C_4)$-alkoxy or $(C_1-C_4)$-thioalkoxy groups, halo$(C_1-C_4)$alkyl, or aryl-$(C_1-C_4)$alkyl groups, provided that when R' and R" are attached to the same nitrogen atom, they can be combined with the nitrogen atom to form a 5-, 6- or 7-membered ring;

with the proviso that the following compounds are excluded from protection:

2-[4-[2-(4-methylphenyl)ethynyl]phenoxy]-acetic acid,
4-[2-(1-pyrenyl)ethynyl]-benzenepropanoic acid,
4-[2-[4-(carboxymethoxy)phenyl]ethynyl]-2,6-Pyridinedicarboxylic acid,
N,N'-[[4[[4-(carboxymethoxy)phenyl]ethynyl]-2,6-pyridinediyl]bis(methylene)]bis[N-[2-(1,1-dimethylethoxy)-2-oxoethyl]-glycine,
N,N'-[[4-[[4-(carboxymethoxy)phenyl]ethynyl]-2,6-pyridinediyl]bis(methylene)]bis[N-[2-(1,1-dimethylethoxy)-2-oxoethyl]-glycine 1,1'-bis(1,1-dimethylethyl) ester,
2-[4-(2-phenylethynyl)phenoxy]-acetic acid,
N-[4[[5-[(2,4-diamino-5-pyrimidinyl)methyl]-2,3-dimethoxyphenyl]ethynyl]phenyl]-N-[(trifluoromethyl)sulfonyl]glycine,
4-[[6-amino-9-(N-ethyl-β-D-ribofuranuronamidosyl)-9H-purin-2-yl]ethynyl]-benzenepropanoic acid,
4-[2-[4-amino-7[2-deoxy-5-O-[hydroxy[[hydroxy(phosphonooxy)phosphinyl]oxy]-phosphinyl]-β-D-erythro-pentofuranosyl]-7H-pyrrolo[2,3-d]pyrimidin-5-yl]ethynyl]-L-phenylalanine,
4-[2-[6-amino-9-[2-deoxy-5-O-[hydroxy[[hydroxy(phosphonooxy)phosphinyl]oxy]-phosphinyl]-β-D-erythro-pentofuranosyl]-9H-purin-8-yl]ethynyl]-L-phenylalanine,
4-[2-[4-amino-7-(2-deoxy-β-D-erythro-pentofuranosyl)-7H-pyrrolo[2,3-d]pyrimidin-6-yl]ethynyl]-L-phenylalanine,
[2-[6-amino-9-(2-deoxy-β-D-erythro-pentofuranosyl)-9H-purin-8-yl]ethynyl]-L-phenylalanine, and
2-[4-[2-(4-cyclobutyl-2-thiazol)ethynyl]-2-(2H-tetrazol-5-yl)phenoxy]-acetic acid.

2. The compound of claim 1, wherein X is —C($R^4R^5$)—.

3. The compound of claim 1, wherein $R^1$, $R^4$ and $R^5$ are independently selected from hydrogen and $(C_1-C_3)$alkyl.

4. The compound of claim 1, wherein $R^1$ is hydrogen.

5. The compound of claim 2 wherein $R^4$ and $R^5$ are hydrogen.

6. The compound of claim 1, wherein $R^3$ is selected from hydrogen and halogen.

7. The compound of claim 1, wherein Ar is selected from the group consisting of an optionally substituted phenyl, 2-pyridyl, 3-pyridyl, 4-pyridyl, 2-thienyl, 3-thienyl, 2-thiazolyl, 4-thiazolyl, 5-thiazolyl, 4-thiazolyl, 2-furyl, 3-furyl, 2-oxazolyl, 4-oxazolyl, 5-oxazolyl, 2-pyrrolyl, 3-pyrrolyl, 1-pyrrazolyl, 2-pyrrazolyl, 3-pyrrazolyl, 2-pyrimidyl, 4-pyrimidyl, 5-pyrimidyl, 4-triazolyl, 5-tetrazolyl, 2-naphthyl, 3-naphthyl, 2-quinolyl, 3-quinolyl, 4-quinolyl, 5-quinolyl, 6-quinolyl, 7-quinolyl, 8-quinolyl, 2-benzothiazolyl, 4-benzothiazolyl, 5-benzothiazolyl, 6-benzothiazolyl, 7-benzothiazolyl, 1-indolyl, 2-indolyl, 3-indolyl, 4-indolyl, 5-indolyl, 6-indolyl and 7-indolyl.

8. The compound of claim 1, wherein Ar is phenyl.

9. The compound of claim 1, wherein Ar is 4-pyridyl.

10. The compound of claim 8, with $R^2$ substituted in the ortho or meta position relative to the alkyne, provided that $R^2$ is not H.

11. The compound of claim 10, wherein $R^2$ is $(C_1-C_6)$alkyl.

12. The compound of claim 2, wherein $R^1$ is methylene, $R^4$ is hydrogen, and $R^1$ is connected to X with a covalent bond.

13. A pharmaceutical composition, comprising: a pharmaceutically acceptable carrier, diluent, or excipient, and the compound of claim 1.

14. A therapeutic composition, comprising; the compound of claim 1 and a second therapeutic agent as a combined preparation for simultaneous, separate, or sequential use in the treatment of a disease or condition mediated by GPR40.

15. The compound of claim 1, wherein the number is zero, one, or two substituents.

* * * * *